US012365706B2

(12) United States Patent
Boyer et al.

(10) Patent No.: US 12,365,706 B2
(45) Date of Patent: Jul. 22, 2025

(54) MACROCYCLIC PEPTIDES AS POTENT INHIBITORS OF K-RAS G12D MUTANT

(71) Applicants: Merck Sharp & Dohme LLC, Rahway, NJ (US); MSD International GMBH (Singapore Branch), Singapore (SG); Agency for Science, Technology and Research, Singapore (SG); Nicolas C. Boyer, Somerville, MA (US); Michael B. Garrigou, Newton, MA (US); Sookhee Nicole Ha, Lewisville, TX (US); Chunhui Huang, Arlington, MA (US); Anthony W. Partridge, Cambridge, MA (US); Tomi K. Sawyer, Southborough, MA (US); Pietro Aronica, Singapore (SG); Charles W. Johannes, Singapore (SG); Srinivasaraghavan Kannan, Singapore (SG); Chandra S. Verma, Singapore (SG); Tsz Ying Yuen, Singapore (SG)

(72) Inventors: Nicolas C. Boyer, Somerville, MA (US); Michael B. Garrigou, Newton, MA (US); Sookhee Nicole Ha, Lewisville, TX (US); Chunhui Huang, Arlington, MA (US); Anthony W. Partridge, Cambridge, MA (US); Tomi K. Sawyer, Southborough, MA (US); Pietro Aronica, Singapore (SG); Charles W. Johannes, Singapore (SG); Srinivasaraghavan Kannan, Singapore (SG); Chandra S. Verma, Singapore (SG); Tsz Ying Yuen, Singapore (SG)

(73) Assignees: Merck Sharp & Dohme LLC, Rahway, NJ (US); MSD International GMBH (Singapore Branch), Singapore (SG); Agency for Science, Technology and Research, Singapore (SG)

(*) Notice: Subject to any disclaimer, the term of this patent is extended or adjusted under 35 U.S.C. 154(b) by 425 days.

(21) Appl. No.: 17/783,224

(22) PCT Filed: Dec. 15, 2020

(86) PCT No.: PCT/US2020/065009
§ 371 (c)(1),
(2) Date: Jun. 7, 2022

(87) PCT Pub. No.: WO2021/126799
PCT Pub. Date: Jun. 24, 2021

(65) Prior Publication Data
US 2023/0083431 A1 Mar. 16, 2023

Related U.S. Application Data

(60) Provisional application No. 62/949,705, filed on Dec. 18, 2019.

(51) Int. Cl.
*C07K 7/08* (2006.01)
*A61K 38/00* (2006.01)
*A61P 35/00* (2006.01)

(52) U.S. Cl.
CPC ............. *C07K 7/08* (2013.01); *A61P 35/00* (2018.01); *A61K 38/00* (2013.01)

(58) Field of Classification Search
None
See application file for complete search history.

(56) References Cited

U.S. PATENT DOCUMENTS 6,413,932 B1  7/2002  Cerretti et al.
6,596,852 B2  7/2003  Cerretti et al.
(Continued)

FOREIGN PATENT DOCUMENTS

WO    1999052889 A1    10/1999
WO    2004037169 A2     5/2004
(Continued)

OTHER PUBLICATIONS

Niida et al. "Investigation of the structural requirements of K-Ras(G12D) selective inhibitory peptide KRpep-2d using alanine scans and cysteine bridging," Bioorganic & Medicinal Chemistry Letters, vol. 27, Issue 12, Jun. 15, 2017, pp. 2757-2761 (Year: 2017).*
Feng and Xu "Inspiration from the mirror: D-amino acid containing peptides in biomedical approaches," BioMol Concepts 2016; 7(3): 179-187 (Year: 2016).*
Barnett, Stanley F. et al., Identification and characterization of pleckstrin-homology-domaindependent and isoenzyme-specific Akt inhibitors, Biochem. J., 2005, 399-408, 385.
Milletti, Francesca, Cell-penetrating peptides: classes, origin, and current landscape, Drug Discovery Today, 2012, 850-860, vol. 17, Nos. 15/16.
Sakamoto, K. et al., K-Ras(G12D)-selective inhibitory peptides generated by random peptide T7 phage display technology, Biochemical and Biophysical Research Communications, 2017, 605-611, 484.
Schneeweis, Christian et al., Oncogenic KRAS and the EGFR loop in pancreatic carcinogenesis—A connection to licensing nodes, Small GTPases, 2018, 457-464, 9:6.
(Continued)

*Primary Examiner* — Christina Bradley
(74) *Attorney, Agent, or Firm* — Eric A. Meade; Emily K. Sauter

(57) ABSTRACT

The invention provides compounds of the Formula (I) or pharmaceutically acceptable salts thereof, wherein the variables are as described herein. The compounds or their pharmaceutically acceptable salts can inhibit the G12D mutant of Kirsten rat sarcoma (K-Ras) protein and are expected to have utility as therapeutic agents, for example, for treating cancer. The invention also provides pharmaceutical compositions which comprise compounds of Formula (I) or pharmaceutically acceptable salts thereof. The inven-
(Continued)

tion also relates to methods for use of the compounds or their pharmaceutically acceptable salts in the therapy and prophylaxis of cancer and for preparing pharmaceuticals for this purpose.

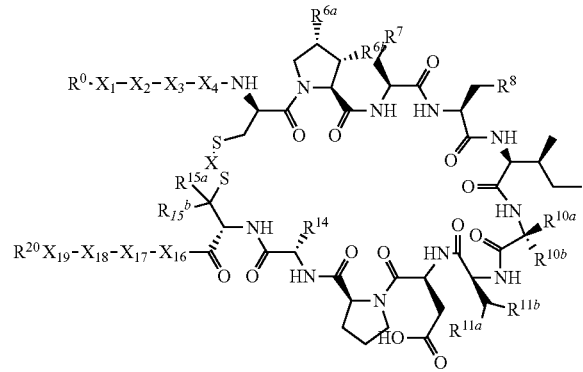

(I)

14 Claims, 12 Drawing Sheets

Specification includes a Sequence Listing.

(56) References Cited

U.S. PATENT DOCUMENTS

| | | | |
|---|---|---|---|
| 6,727,225 | B2 | 4/2004 | Wiley |
| 2002/0042368 | A1 | 4/2002 | Fanslow et al. |
| 2019/0309020 | A1 | 10/2019 | Pei et al. |

FOREIGN PATENT DOCUMENTS

| | | |
|---|---|---|
| WO | 2005016252 A2 | 2/2005 |
| WO | 2009055730 A1 | 4/2009 |

OTHER PUBLICATIONS

Yang, Xiao-Dong et al., Eradication of Established Tumors by a Fully Human Monoclonal Antibody to the Epidermal Growth Factor Receptor without Concomitant Chemotherapy, Cancer Research, 1999, 1236-1243, 59.

Garrigou, Michael et al., Accelerated Identification of Cell Active KRAS Inhibitory Macrocyclic Peptides using Mixture Libraries and Automated Ligand Identification System (ALIS) Technology, J. Med. Chem., 65, 8961-8974, 2022.

Lim, Shuhui et al., Discovery of cell active macrocyclic peptides with on-target inhibition of KRAS signaling, Chem. Sci., 12, 15975-15987, 2021.

Peier, Andrea et al., NanoClick: A High Throughput, Target-Agnostic Peptide Cell Permeability Assay, ACS Chem. Biol., 16, 293-309, 2021.

\* cited by examiner

| Seq. ID No. | Sequence | Formula | Exact Mass (Da) | Molecular Weight (g.mol⁻¹) | Measured Mass (Da) | Observed Ion |
|---|---|---|---|---|---|---|
| 1 | Ac-Lys(N3)-DArg-DArg-DArg-DCys*-Pro-Leu-2Nal-Ile-Ser-Tyr-Asp-Pro-Val-Cys*-DArg-DArg-DArg-NH2 | C119 H197 N48 O25 S2 | 2761.49827 | 2763.27 | 921.8 | $[M+3H]^{3+}$ |
| 2 | Ac-Lys(N3)-DArg-DArg-DArg-DCys*-Pro-Leu-Tyr-Ile-Ser-AMS-Tyr-Asp-Pro-Val-Cys*-DArg-DArg-DArg-NH2 | C116 H197 N48 O26 S2 | 2741.49318 | 2743.23 | 686.6 | $[M+4H]^{4+}$ |
| 3 | CPP12-Gly-Lys(N3)-Aeea-Arg-Arg-DCys*-Pro-Leu-Tyr-Ile-Ser-Tyr-Asp-Pro-Val-Cys*-Arg-Arg-NH2 | C157 H241 N54 O34 S2 | 3489.81524 | 3492.06 | 873.8 | $[M+4H]^{4+}$ |
| 4 | Ac-Lys(N3)-DArg-DArg-DArg-DCys*-Pro-Leu-Tyr-Ile-Ser-Tyr-Asp-Pro-Val-Cys*-DArg-DArg-DArg-T3PhP-DArg-DArg-NH2 | C121 H199 N48 O26 S2 | 2803.50883 | 2805.30 | 562.1 | $[M+5H]^{5+}$ |
| 5 | Ac-Lys(N3)-DArg-DArg-DArg-DCys*-Pro-Leu-2Nal-Ile-Ser-Tyr-Asp-Pro-Cha-Cys*-DArg-DArg-DArg-NH2 | C123 H203 N48 O25 S2 | 2815.54522 | 2817.36 | 939.7 | $[M+3H]^{3+}$ |
| 6 | Ac-Lys(N3)-DArg-DArg-DArg-DCys*-Pro-Leu-2Nal-Ile-Ser-Trp-Asp-Pro-Chg-Cys*-DArg-DArg-DArg-NH2 | C124 H201 N49 O24 S2 | 2824.54555 | 2826.37 | 942.8 | $[M+3H]^{3+}$ |
| 7 | Ac-Lys(N3)-NMeArg-Arg-NMeArg-DCys*-Pro-Leu-Tyr-Ile-Ser-Tyr-Asp-Pro-Val-Cys*-Arg-NMeArg-Arg-NMeArg-NH2 | C119 H203 N48 O26 S2 | 2783.54013 | 2785.31 | 465.1 | $[M+6H]^{6+}$ |

FIG. 1A

| | | | | |
|---|---|---|---|---|
| 8 | cyclo(DArg#-DArg-DArg-DArg-DCys*-Pro-Leu-Tyr-Ile-Ser-Tyr-Asp-Pro-Val-Cys*-DArg-DArg-DArg#) | C107 H180 N43 O24 S2 | 2514.35496 | 2515.97 | 839.4 | [M+3H]³⁺ |
| 9 | Ac-Lys(N3)-DArg-DArg-DArg-DArg-DCys*-Pro-Leu-Tyr-Ile-Ser-Tyr-Asp-AMP-Val-Cys*-DArg-DArg-DArg-NH2 | C116 H197 N48 O26 S2 | 2741.49318 | 2743.23 | 2742.6 | [M+H]⁺ |
| 10 | Ac-DArg-DArg-DArg-DArg-DArg-DCys*-Pro-Leu-Tyr-Ile-Ser-Tyr-Asp-Pro-Val-Cys*-DArg-DArg-DArg-NH2 | C109 H192 N44 O25 S2 | 2573.39207 | 2575.04 | 859.2 | [M+3H]³⁺ |
| 11 | Ac-Lys(N3)-DArg-DArg-DArg-DArg-DCys*-Pro-Leu-Tyr-Ile-Cle-Tyr-Asp-Pro-Val-Cys*-DArg-DArg-DArg-NH2 | C118 H199 N48 O25 S2 | 2751.51392 | 2753.27 | 918.4 | [M+3H]³⁺ |
| 12 | Ac-Lys(N3)-DArg-DArg-DArg-DArg-DCys*-Pro-Leu-Tyr-Ile-Ser-Tyr-Asp-Pro-Cha-Cys*-DArg-DArg-DArg-NH2 | C119 H201 N48 O26 S2 | 2781.52448 | 2783.30 | 928.3 | [M+3H]³⁺ |
| 13 | Ac-Lys(N3)-NMeArg-DArg-DArg-NMeArg-DCys*-Pro-Leu-Tyr-Ile-Ser-Tyr-Asp-Pro-Val-Cys*-DArg-NMeArg-DArg-NMeArg-NH2 | C119 H203 N48 O26 S2 | 2783.54013 | 2785.31 | 697.4 | [M+4H]⁴⁺ |
| 14 | Ac-Lys(N3)-DArg-DArg-DArg-DArg-DCys*-Pro-Leu-2Nal-Ile-Tyr-Asp-Pro-Cha-Cys*-DArg-DArg-DArg-NH2 | C126 H207 N48 O24 S2 | 2839.58160 | 2841.42 | 947.8 | [M+3H]³⁺ |
| 15 | Ac-Lys(N3)-DArg-DArg-DArg-DArg-DCys*-Pro-Leu-Tyr-Ile-Ser-Tyr-Asp-Pro-Val-Cys*-DArg-DArg-DArg-NH2 | C115 H195 N48 O26 S2 | 2727.47753 | 2729.21 | 683.3 | [M+4H]⁴⁺ |

FIG. 1B

| | Sequence | Formula | Mass | m/z | Charge |
|---|---|---|---|---|---|
| 16 | Ac-Penetratin-Gly-Lys(N3)-Aeea-DCys*-Pro-Leu-Tyr-Ile-Ser-Tyr-Asp-Pro-Val-Cys*-Arg-NH2 | C185 H290 N56 O42 S3 | 4064.14403 | 4066.83 | 1017.5 [M+4H]4+ |
| 17 | Ac-Lys(N3)-Arg-Arg-DCys*-Pro-Leu-F4tBu-Ile-Ser-F4tBu-Asp-Pro-Val-Cys*-Arg-Arg-NH2 | C99 H166 N32 O20 S2 | 2183.20846 | 2184.68 | 729.0 [M+3H]3+ |
| 18 | Ac-Lys(N3)-Arg-Arg-Arg-Arg-DCys*-Pro-Leu-2Nal-Ile-Ser-Tyr-Asp-Pro-Val-Cys*-Arg-Arg-Arg-NH2 | C119 H197 N48 O25 S2 | 2761.49827 | 2763.27 | 921.8 [M+3H]3+ |
| 19 | Ac-Lys(N3)-DArg-DArg-DArg-DArg-DCys*-Pro-Leu-Tyr-Ile-Ser-Tyr-Asp-Pro-Glu-Cys*-DArg-DArg-DArg-DArg-NH2 | C115 H200 N48 O28 S2 | 2757.45171 | 2759.19 | 552.8 [M+5H]5+ |
| 20 | Ac-DCys*-Pro-Leu-Tyr-Ile-Ser-Tyr-Asp-Pro-Val-Cys*-Arg-Gly-Lys(N3)-Aeea-Penetratin-NH2 | C185 H290 N56 O42 S3 | 4064.14403 | 4066.83 | 1017.4 [M+4H]4+ |
| 21 | Ac-Arg-Arg-DCys*-Pro-Leu-Tyr-Ile-Cha-Cha-Asp-Pro-Val-Cys*-Arg-Arg-NH2 | C91 H156 N28 O19 S2 | 2005.12300 | 2006.49 | 669.5 [M+3H]3+ |
| 22 | Ac-Lys(N3)-Arg-Arg-Arg-Arg-DCys*-Pro-Leu-Tyr-Ile-Ser-Tyr-Asp-Pro-Cha-Cys*-Arg-Arg-Arg-NH2 | C119 H201 N48 O26 S2 | 2781.52448 | 2783.30 | 928.4 [M+3H]3+ |
| 23 | Ac-Lys(N3)-Arg-Arg-DCys*-Pro-Leu-Tyr-Ile-Dbg-Tyr-Asp-Pro-Val-Cys*-Arg-Arg-NH2 | C98 H164 N32 O21 S2 | 2185.18772 | 2186.65 | 729.5 [M+3H]3+ |
| 24 | Ac-Lys(N3)-Arg-Arg-Arg-Arg-DCys*-Pro-Leu-Tyr-Ile-Cle-Tyr-Asp-Pro-Val-Cys*-Arg-Arg-Arg-Arg-NH2 | C118 H199 N48 O25 S2 | 2751.51392 | 2753.27 | 918.4 [M+3H]3+ |

FIG. 1C

| | | | | |
|---|---|---|---|---|
| 25 | Ac-Lys(N3)-hArg-hArg-DCys*-Pro-Leu-Bip-Ile-Ser-Tyr-Asp-Pro-Val-Cys*-hArg-hArg-NH2 | C101 H162 N32 021 S2 | 2219.17207 | 2220.67 | 741.1 | [M+3H]³⁺ |
| 26 | Ac-Lys(N3)-DArg-DLeu-DLeu-DArg-DCys*-T3PhP Leu-Tyr-Ile-Ser-Tyr-Asp-Pro-Val-Cys*-DArg-DLeu-DLeu-NH2 | C121 H198 N36 026 S2 | 2631.44064 | 2633.19 | 659.1 | [M+H4]⁴⁺ |
| 27 | Ac-Lys(N3)-DArg-DArg-DCys*-T3PhP-Leu-Bip-Ile-Ser-Tyr-Asp-Pro-Val-Cys*-DArg-DArg-NH2 | C103 H158 N32 021 S2 | 2239.14077 | 2240.66 | 561.0 | [M+4H]⁴⁺ |
| 28 | Ac-Lys(N3)-Arg-Arg-DCys*-T34Me2cPP-Leu-Tyr-Ile-Ser-Tyr-Asp-Pro-Val-Cys*-Arg-Arg-NH2 | C94 H154 N32 022 S2 | 2143.10439 | 2144.53 | 715.5 | [M+3H]³⁺ |
| 29 | Ac-Lys(N3)-Arg-Arg-DCys*-Pro-Leu-Tyr-Ile-Aic-Tyr-Asp-Pro-Val-Cys*-Arg-Arg-NH2 | C98 H154 N32 021 S2 | 2175.10947 | 2176.57 | 726.3 | [M+3H]³⁺ |
| 30 | Ac-Lys(N3)-hArg-hArg-DCys*-T3PhP-Leu-Tyr-Ile-Ser-Tyr-Asp-Pro-Val-Cys*-hArg-hArg-NH2 | C101 H159 N32 022 S2 | 2235.16699 | 2236.67 | 560.0 | [M+4H]⁴⁺ |
| 31 | Ac-Lys(N3)-DArg-DArg-DLeu-DLeu-DArg-DCys*-Pro-Leu-Bip-Ile-Ser-Tyr-Asp-Pro-Val-Cys*-DArg-DLeu-DLeu-NH2 | C121 H195 N36 025 S2 | 2615.44573 | 2617.19 | 873.3 | [M+3H]³⁺ |
| 32 | Ac-Lys(N3)-DArg-DLeu-DLeu-DArg-DCys*-Pro-Leu-2Nal-Ile-Ser-Tyr-Asp-Pro-Val-Cys*-DArg-DLeu-DLeu-NH2 | C119 H193 N36 025 S2 | 2589.43008 | 2591.15 | 864.7 | [M+3H]³⁺ |
| 33 | Ac-Lys(N3)-Arg-Arg-Arg-DCys*-Pro-Leu-YCF3-Ile-Ser-YCF3-Asp-Pro-Val-Cys*-Arg-Arg-NH2 | C93 H148 F6 N32 022 S2 | 2239.04786 | 2240.46 | 747.5 | [M+3H]³⁺ |
| 34 | Ac-Arg-Arg-Arg-Arg-DCys*-Pro-Leu-Tyr-Ile-Ser-Tyr-Asp-Pro-Val-Cys*-Arg-Arg-Arg-NH2 | C109 H185 N44 025 S2 | 2573.39207 | 2575.04 | 644.6 | [M+4H]⁴⁺ |

FIG. 1D

| | | | | |
|---|---|---|---|---|
| 35 | Ac-Lys(N3)-Arg-Arg-DCys*-T3PhP-Leu-Tyr-Ile-Ser-Tyr-Asp-Pro-Val-Cys*-Arg-Arg-NH2 | C97 H154 N32 022 S2 | 2179.10439 | 2180.56 | 727.8 | $[M+3H]^{3+}$ |
| 36 | Ac-Lys(N3)-Arg-Arg-DCys*-Pro-BHL-Tyr-Ile-Ser-Tyr-Asp-Pro-Val-Cys*-Arg-Arg-NH2 | C92 H152 N32 022 S2 | 2117.08874 | 2118.49 | 1059.7 | $[M+2H]^{2+}$ |
| 37 | Ac-Lys(N3)-DArg-DLeu-DLeu-DArg-DCys*-Pro-Leu-F4CF3-Ile-Ser-Tyr-Asp-Pro-Val-Cys*-DArg-DLeu-DArg-NH2 | C116 H190 F3 N36 025 S2 | 2607.40181 | 2609.09 | 870.7 | $[M+3H]^{3+}$ |
| 38 | Ac-Lys(N3)-Arg-Arg-DCys*-Pro-Leu-Tyr-Ile-Cle-Tyr-Asp-Pro-Val-Cys*-Arg-Arg-NH2 | C94 H154 N32 021 S2 | 2127.10947 | 2128.53 | 710.2 | $[M+3H]^{3+}$ |
| 39 | Ac-Arg-Arg-DCys*-Pro-Leu-Tyr-Ile-Trp-1Nal-Asp-Pro-Val-Cys*-Arg-Arg-NH2 | C97 H147 N29 019 S2 | 2082.05565 | 2083.49 | 695.3 | $[M+3H]^{3+}$ |
| 40 | Ac-Arg-Arg-DCys*-Pro-Leu-Tyr-Ile-Ser-Bhg-Asp-Pro-Val-Cys*-Arg-Arg-NH2 | C91 H141 N28 021 S2 | 2025.01893 | 2026.39 | 676.2 | $[M+3H]^{3+}$ |
| 41 | Ac-Lys(N3)-Arg-Arg-DCys*-Pro-Leu-Tyr-Ile-C8G-Tyr-Asp-Pro-Val-Cys*-Arg-Arg-NH2 | C99 H156 N32 021 S2 | 2189.12512 | 2190.60 | 1095.7 | $[M+2H]^{2+}$ |
| 42 | Ac-Lys(N3)-Arg-Arg-DCys*-Pro-Leu-Tyr-Ile-C8G-Tyr-Asp-Pro-Val-Cys*-Arg-Arg-NH2 | C98 H164 N32 021 S2 | 2185.18772 | 2186.65 | 1094.0 | $[M+2H]^{2+}$ |
| 43 | Ac-Lys(N3)-Arg-Arg-DCys*-Pro-Leu-YBzl-Ile-Ser-Tyr-Asp-Pro-Val-Cys*-Arg-Arg-NH2 | C98 H156 N32 022 S2 | 2193.12004 | 2194.59 | 1097.8 | $[M+2H]^{2+}$ |
| 44 | Ac-Lys(N3)-Arg-Arg-Arg-Arg-DCys*-T3OHP-Leu-Tyr-Ile-Ser-Tyr-Asp-Pro-Val-Cys*-Arg-Arg-Arg-Arg-NH2 | C115 H195 N48 027 S2 | 2743.47244 | 2745.21 | 458.4 | $[M+6H]^{6+}$ |
| 45 | Ac-Lys(N3)-Arg-Arg-DCys*-Pro-Leu-Tyr-Ile-Ser-4Ial-Asp-Pro-Val-Cys*-Arg-Arg-NH2 | C93 H151 N33 021 S2 | 2126.08907 | 2127.50 | 710.5 | $[M+3H]^{3+}$ |

FIG. 1E

| # | Sequence | Formula | Mass | [M+nH] | Charge |
|---|---|---|---|---|---|
| 46 | Ac-Lys(N3)-Arg-Nle-Nle-Arg-DCys*-Pro-Leu-Tyr-Ile-Ser-Tyr-Asp-Pro-Val-Cys*-Arg-Nle-Nle-Arg-NH2 | C115 H194 N36 026 S2 | 2555.40934 | 2557.09 | 853.2 | [M+3H]³⁺ |
| 47 | Ac-Lys(N3)-Arg-Arg-DCys*-Pro-Leu-Tyr-Ile-Lys-Tyr-Asp-Pro-Val-Cys*-Arg-Arg-NH2 | C94 H157 N33 021 S2 | 2144.13602 | 2145.56 | 715.9 | [M+3H]³⁺ |
| 48 | Ac-Arg-Arg-DCys*-Pro-Leu-Tyr-Ile-Trp-Cha-Asp-Pro-Val-Cys*-Arg-Arg-NH2 | C93 H151 N29 019 S2 | 2038.08695 | 2039.48 | 1020.1 | [M+2H]²⁺ |
| 49 | Ac-Lys(N3)-Arg-Leu-Leu-Arg-DCys*-Pro-Leu-2Nal-Ile-Ser-Trp-Asp-Pro-Chg-Cys*-Arg-Leu-Leu-Arg-NH2 | C124 H201 N37 024 S2 | 2652.47736 | 2654.25 | 885.5 | [M+3H]³⁺ |
| 50 | Ac-Arg-Arg-DCys*-Pro-Leu-Tyr-Ile-Ser-Dip-Asp-Pro-Val-Cys*-Arg-Arg-NH2 | C91 H144 N28 020 S2 | 2009.02401 | 2010.39 | 670.8 | [M+3H]³⁺ |
| 51 | Ac-Lys(N3)-Arg-Arg-DArg-DArg-DCys*-Pro-Leu-Bip-Ile-Ser-Tyr-Asp-Pro-Val-Cys*-DArg-DArg-NH2 | C97 H151 N32 021 S2 | 2163.10947 | 2164.56 | 722.7 | [M+3H]³⁺ |
| 52 | Ac-Lys(N3)-Arg-Arg-DCys*-Pro-Leu-Bip-Ile-Ser-Tyr-Asp-Pro-Val-Cys*-Arg-Arg-NH2 | C97 H154 N32 021 S2 | 2163.10947 | 2164.56 | 1082.7 | [M+2H]²⁺ |
| 53 | Ac-Lys(N3)-Arg-Arg-Arg-Arg-DCys*-Pro-Leu-Tyr-Ile-Ser-Tyr-Asp-Pro-Val-Cys*-Arg-Arg-Arg-Arg-NH2 | C115 H195 N48 026 S2 | 2727.47753 | 2729.21 | 910.7 | [M+3H]³⁺ |
| 54 | Ac-Lys(N3)-Arg-Arg-DCys*-Pro-Leu-Tic-Ile-Ser-Tyr-Asp-Pro-Val-Cys*-Arg-Arg-NH2 | C92 H150 N32 021 S2 | 2099.07817 | 2100.48 | 1050.7 | [M+2H]²⁺ |
| 55 | Ac-Lys(N3)-Arg-Arg-DCys*-Pro-Leu-Tyr-Ile-Arg-Tyr-Asp-Pro-Val-Cys*-Arg-Arg-NH2 | C94 H157 N35 021 S2 | 2172.14217 | 2173.57 | 725.3 | [M+3H]³⁺ |
| 56 | Ac-Lys(N3)-Arg-Arg-DCys*-Pro-C8G-Tyr-Ile-Ser-Tyr-Asp-Pro-Val-Cys*-Arg-Arg-NH2 | C95 H158 N32 022 S2 | 2159.13569 | 2160.57 | 720.8 | [M+3H]³⁺ |

FIG.1F

| | | | | | |
|---|---|---|---|---|---|
| 57 | Ac-DArg-Glu‡-DArg-DArg-DCys*-Pro-Leu-Tyr-Ile-Ser-Tyr-Asp-Pro-Val-Cys*-DArg-Lys‡-DArg-NH2 | C108 H178 N39 O26 S2 | 2500.31684 | 2501.94 | 834.7 | [M+3H]3+ |
| 58 | Ac-Lys(N3)-hArg-hArg-DCys*-Pro-Leu-2Nal-Ile-Ser-Tyr-Asp-Pro-Val-Cys*-hArg-hArg-NH2 | C99 H160 N32 O21 S2 | 2193.15642 | 2194.63 | 549.5 | [M+H4]4+ |
| 59 | Ac-Lys(N3)-DArg-DArg-DArg-DCys*-Pro-Leu-Tyr-Ile-Ser-Tyr-Asp-Pro-Val-Cys*-DArg-DArg-DArg-NH2 | C103 H171 N40 O24 S2 | 2415.27531 | 2416.84 | 806.3 | [M+3H]3+ |
| 60 | Ac-Arg-Arg-DCys*-Pro-Leu-Tyr-Ile-Nva-1Nal-Asp-Pro-Val-Cys*-Arg-Arg-NH2 | C91 H146 N28 O19 S2 | 1995.04475 | 1996.41 | 998.7 | [M+2H]2+ |
| 61 | Ac-Lys(N3)-Arg-Arg-DCys*-Pro-Leu-Tyr-Ile-Ser-Tyr-Asp-Pro-Bhg-Cys*-Arg-Arg-NH2 | C103 H156 N32 O22 S2 | 2253.12004 | 2254.64 | 1127.8 | [M+2H]2+ |
| 62 | Ac-TP2-Gly-Lys(N3)-Aeea-DCys*-Pro-Leu-Tyr-Ile-Ser-Tyr-Asp-Pro-Val-Cys*-Arg-Arg-NH2 | C153 H242 N41 O37 S2 | 3306.75220 | 3308.92 | 1654.9 | [M+2H]2+ |
| 63 | Ac-Lys(N3)-Arg-Arg-DCys*-Pro-Leu-Tyr-Ile-Ser-Tyr-Npg-Tyr-Ile-Ser-Tyr-Asp-Pro-Val-Cys*-Arg-Arg-NH2 | C92 H152 N32 O22 S2 | 2117.08874 | 2118.49 | 1059.7 | [M+2H]2+ |
| 64 | Ac-Lys(N3)-Arg-Arg-DCys*-Pro-Leu-Tyr-Ile-Ser-DBhg-Asp-Pro-Val-Cys*-Arg-Arg-NH2 | C99 H156 N32 O21 S2 | 2189.12512 | 2190.60 | 1095.7 | [M+2H]2+ |
| 65 | Ac-Lys(N3)-Arg-Arg-DCys*-Pro-Leu-Tyr-Ile-Ser-Tyr-Asp-Pro-Val-Pen*-Arg-Arg-NH2 | C93 H154 N32 O22 S2 | 2131.10439 | 2132.52 | 1066.8 | [M+2H]2+ |
| 66 | Ac-Lys(N3)-Arg-Arg-DCys*-Pro-Leu-Lys-Ile-Ser-Tyr-Asp-Pro-Val-Cys*-Arg-Arg-NH2 | C88 H153 N33 O21 S2 | 2068.10472 | 2069.46 | 690.6 | [M+3H]3+ |
| 67 KRpep-2d | Ac-Arg-Arg-Arg-Arg-Cys†-Pro-Leu-Tyr-Ile-Ser-Tyr-Asp-Pro-Val-Cys†-Arg-Arg-Arg-Arg-NH2 | C108 H182 N44 O25 S2 | 2559.37642 | 2561.05 | NA | NA |

FIG.1G

| | | | | | |
|---|---|---|---|---|---|
| 68 | Ac-Lys(N3)-Arg-Arg-Arg-Arg-Arg-Cys†-Pro-Leu-Tyr-Ile-Ser-Tyr-Asp-Lys(5FAM)-Val-Cys†-Arg-Arg-Arg-Arg-NH2 | C136 H208 N49 O32 S2 | 3102.55182 | 3104.58 | 622.0 [M+5H]5+ |
| 69 | Ac-Arg-Arg-DCys*-Pro-Leu-Tyr-Ile-Ser-Tyr-Asp-Lys(5FAM)-Val-Cys*-Arg-Arg-NH2 | C107 H155 N29 O27 S2 | 2338.07756 | 2339.68 | 585.8 [M+4H]4+ |

"*", "#", "†", "‡" indicate residues involved in cyclic bond formation. Residues (e.g., Cys, DCys, Pen) indicated with "*" indicated that the two sulfur atoms of the side chains are cyclized by a thioacetal bridge (S-CH$_2$-S or methylene cross-linker). Residues (e.g., Cys, DCys, Pen) indicated with "†" indicated that the two sulfur atoms of the side chains are cyclized by a disulfide bond (S-S cross-linker). Residues (e.g., Lys, Dab, Dap, Asp, Glu) indicated with "‡" are cyclized by side chain-to-side chain lactam bridge formation. Amino acids marked by "#" are cyclized by head-to-tail lactamization. NA = Not Applicable.

FIG.1H

| Seq ID No. | TR-FRET [K-Ras^G12D (GMPPNP)] EC$_{50}$ (nM) | TR-FRET [K-Ras^G12D (GDP)] EC$_{50}$ (nM) | Alpha Screen (1 h, AsPC-1 cells) IC$_{50}$ (μM) | Alpha Screen (18 h, AsPC-1 cells) IC$_{50}$ (μM) | LDH Release (1 h, AsPC-1 cells) IC$_{50}$ (μM) | LDH Release (18 h, AsPC-1 cells) IC$_{50}$ (μM) | NanoClick (4 h, HeLa cells) EC$_{50}$ (nM) | NanoClick (18 h, HeLa cells) EC$_{50}$ (nM) | Cell Homogenate Stability (HeLa cells) t$_{1/2}$ (min) |
|---|---|---|---|---|---|---|---|---|---|
| 1 | NT | 378 | 0.8 | 5.7 | >50 | 27.6 | >10000 | 165.6 | NT |
| 2 | NT | 54 | 0.9 | 1.7 | >50 | >50 | 1777.0 | 32.1 | NT |
| 3 | 317 | 235 | 1.2 | 7.1 | 23.7 | 7.1 | 554.5 | 93.5 | 37 |
| 4 | NT | 68 | 1.4 | 3.3 | >50 | >50 | 144.8 | 50.6 | NT |
| 5 | NT | 449 | 1.4 | 3.4 | >50 | 11.1 | >10000 | 103.0 | NT |
| 6 | NT | 1305 | 1.6 | 4.0 | >50 | 10.1 | >10000 | 186.8 | NT |
| 7 | NT | 130 | 1.7 | 32.2 | >50 | >50 | 1078.0 | 131.7 | NT |
| 8 | NT | 205 | 1.7 | 8.6 | >50 | >50 | NA | NA | NT |
| 9 | NT | 84 | 2.0 | 7.9 | >50 | >50 | 7287.0 | 34.9 | NT |
| 10 | NT | 135 | 2.2 | 8.9 | >50 | >50 | NA | NA | NT |
| 11 | NT | 666 | 2.5 | 2.5 | >50 | >50 | >10000 | 47.1 | 153 |
| 12 | NT | 145 | 2.6 | 8.7 | >50 | 35.0 | >10000 | 41.3 | 190 |
| 13 | NT | 148 | 2.7 | 12.8 | >50 | >50 | 179.9 | 49.6 | NT |
| 14 | NT | 3033 | 3.0 | 5.3 | >50 | 11.0 | >10000 | 148.0 | NT |
| 15 | 24 | 83 | 5.0 | 19.8 | >50 | >50 | 250.5 | 34.9 | NT |
| 16 | 351 | 400 | 3.1 | 19.1 | >50 | 21.0 | NT | NT | NT |

FIG. 2A

| | | | | | | | | |
|---|---|---|---|---|---|---|---|---|
| 17 | NT | 184 | 3.6 | 30.4 | 12.7 | 10.9 | 186.2 | 78.6 | >360 |
| 18 | NT | 104 | 4.8 | 31.3 | >50 | 36.0 | >10000 | 128.5 | NT |
| 19 | NT | 135 | 5.0 | >50 | >50 | >50 | 451.2 | 53.3 | NT |
| 20 | 127 | 406 | 6.5 | 31.1 | >50 | 45.2 | NT | NT | NT |
| 21 | NT | 1006 | 7.1 | >50 | >50 | >50 | NA | NA | 72 |
| 22 | NT | 114 | 7.4 | >50 | >50 | 46.8 | >10000 | 160.7 | NT |
| 23 | NT | 1404 | 7.7 | >50 | >50 | >50 | 5186.0 | 163.8 | 299 |
| 24 | NT | 355 | 8.1 | >50 | >50 | >50 | >10000 | 189.7 | NT |
| 25 | NT | 45 | 8.3 | >50 | >50 | >50 | 2260.0 | 116.4 | 368 |
| 26 | NT | 152 | 9.0 | 37.0 | >50 | >50 | 6217.0 | 72.2 | >360 |
| 27 | NT | 47 | 9.2 | >50 | >50 | >50 | 8172.0 | 104.9 | >360 |
| 28 | NT | 42 | 9.5 | >50 | >50 | >50 | 3134.0 | 1537.0 | 38 |
| 29 | NT | 156 | 10.3 | >50 | >50 | >50 | 3701.0 | 355.8 | 201 |
| 30 | NT | 13 | 10.7 | >50 | >50 | >50 | >10000 | 938.1 | 130 |
| 31 | NT | 902 | 11.2 | 33.6 | 41.7 | 24.0 | 987.8 | 69.6 | >360 |
| 32 | NT | 1060 | 11.2 | 22.1 | >50 | >50 | 104.7 | 35.7 | >360 |
| 33 | NT | 781 | 11.7 | >50 | >50 | >50 | 2336.0 | 85.1 | 258 |
| 34 | 15 | 41 | 11.7 | >50 | >50 | >50 | NA | NA | NT |
| 35 | NT | 17 | 11.9 | >50 | >50 | >50 | >10000 | 420.3 | 81 |
| 36 | 1330 | 10939 | 11.9 | 34.7 | >50 | >50 | >10000 | 1382.0 | 200 |
| 37 | NT | 1102 | 12.3 | 47.0 | >50 | 39.7 | 280.5 | 50.3 | 312 |

FIG.2B

| | | | | | | | |
|---|---|---|---|---|---|---|---|
| 38 | 37 | 235 | 12.9 | >50 | >50 | >10000 | 470.5 | 230 |
| 39 | NT | 2087 | 13.1 | >50 | >50 | NA | NA | 107 |
| 40 | 25 | 16 | 14.6 | >50 | >50 | NA | NA | 237 |
| 41 | NT | 1041 | 14.7 | >50 | >50 | 1504.0 | 391.2 | 301 |
| 42 | NT | 1128 | 15.2 | >50 | >50 | 1437.0 | 187.2 | 163 |
| 43 | 30 | 46 | 15.3 | 38.0 | >50 | NT | NT | NT |
| 44 | NT | 75 | 15.6 | >50 | >50 | 180.7 | 118.6 | NT |
| 45 | NT | 425 | 17.9 | >50 | >50 | NT | NT | NT |
| 46 | NT | 147 | 18.0 | >50 | >50 | 1493.0 | 75.1 | 63 |
| 47 | 233 | 3818 | 18.5 | >50 | >50 | 4961.0 | 411.7 | 124 |
| 48 | NT | 610 | 19.2 | >50 | >50 | NA | NA | 99 |
| 49 | NT | 1335 | 20.1 | >50 | >50 | >10000 | 95.9 | 81 |
| 50 | NT | 149 | 20.4 | >50 | >50 | NA | NA | 254 |
| 51 | NT | 55 | 20.4 | >50 | >50 | 3523.0 | 78.7 | 240 |
| 52 | 25 | 36 | 21.7 | >50 | >50 | 2377.0 | 101.9 | 133 |
| 53 | 39 | 112 | 22.6 | >50 | >50 | 2693.0 | 636.4 | 311 |
| 54 | 3515 | 13067 | 25.0 | 39.8 | >50 | 383.1 | 152.8 | NT |
| 55 | 97 | 1798 | 25.6 | >50 | >50 | >10000 | 543.8 | 65 |
| 56 | NT | 173 | 30.4 | >50 | >50 | 3081.0 | 133.7 | 46 |
| 57 | NT | 279 | 30.7 | >50 | >50 | NA | NA | 26 |
| 58 | NT | 136 | 30.9 | >50 | >50 | >10000 | 359.5 | 216 |

FIG.2C

| 59 | NT | 159 | 33.1 | >50 | >50 | >50 | 1255.0 | 55.8 | 130 |
| 60 | NT | 5538 | 36.4 | >50 | >50 | >50 | NA | NA | 84 |
| 61 | NT | 18334 | 36.7 | >50 | >50 | >50 | 3446.0 | 241.1 | NT |
| 62 | 394 | 1888 | 37.6 | >50 | >50 | >50 | 2126.0 | 171.6 | 24 |
| 63 | 38 | 116 | 38.5 | >50 | >50 | >50 | 7972.0 | 661.1 | 118 |
| 64 | NT | 43445 | 39.4 | 19.8 | 10.8 | 8.8 | 333.2 | 89.0 | NT |
| 65 | 182 | 1384 | 42.4 | >50 | >50 | >50 | NT | NT | NT |
| 66 | 99 | 774 | 49.0 | >50 | >50 | >50 | >10000 | 1101.0 | 91 |
| 67 | 128 | NT | >50 | >50 | >50 | >50 | NA | NA | 24 |

NA = Not Applicable; NT = Not Tested.

FIG.2D

SEQUENCE LISTING

```
<160> NUMBER OF SEQ ID NOS: 146

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: 2Nal
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 1
```

```
Lys Arg Arg Arg Arg Cys Pro Leu Xaa Ile Ser Tyr Asp Pro Val Cys
1               5                   10                  15

Arg Arg Arg Arg
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (11)..(11)
<223> OTHER INFORMATION: AMS
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 2

Lys Arg Arg Arg Arg Cys Pro Leu Tyr Ile Ser Tyr Asp Pro Val Cys
1               5                   10                  15

Arg Arg Arg Arg
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(N3)
```

```
<220> FEATURE:
<221> NAME/KEY: MOD_RES
<222> LOCATION: (3)..(3)
<223> OTHER INFORMATION: Aeea
<220> FEATURE:
<221> NAME/KEY: MOD_RES
<222> LOCATION: (6)..(6)
<223> OTHER INFORMATION: DCys

<400> SEQUENCE: 3

Gly Lys Xaa Arg Arg Cys Pro Leu Tyr Ile Ser Tyr Asp Pro Val Cys
1               5                   10                  15

Arg Arg

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (7)..(7)
<223> OTHER INFORMATION: T3PhP
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 4

Lys Arg Arg Arg Arg Cys Xaa Leu Tyr Ile Ser Tyr Asp Pro Val Cys
1               5                   10                  15

Arg Arg Arg Arg
            20

<210> SEQ ID NO 5
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: 2Nal
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 5

Lys Arg Arg Arg Arg Cys Pro Leu Xaa Ile Ser Tyr Asp Pro Ala Cys
1               5                   10                  15

Arg Arg Arg Arg
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
```

```
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: 2Nal
<220> FEATURE:
<221> NAME/KEY: MOD_RES
<222> LOCATION: (15)..(15)
<223> OTHER INFORMATION: Chg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 6

Lys Arg Arg Arg Arg Cys Pro Leu Xaa Ile Ser Trp Asp Pro Gly Cys
1               5                   10                  15

Arg Arg Arg Arg
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: NMeArg
<220> FEATURE:
<221> NAME/KEY: MOD_RES
<222> LOCATION: (4)..(4)
<223> OTHER INFORMATION: NMeArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (18)..(18)
<223> OTHER INFORMATION: NMeArg
<220> FEATURE:
<221> NAME/KEY: MOD_RES
```

```
<222> LOCATION: (20)..(20)
<223> OTHER INFORMATION: NMeArg

<400> SEQUENCE: 7

Lys Arg Arg Arg Arg Cys Pro Leu Tyr Ile Ser Tyr Asp Pro Val Cys
1               5                   10                  15

Arg Arg Arg Arg
            20

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 8

Arg Arg Arg Arg Cys Pro Leu Tyr Ile Ser Tyr Asp Pro Val Cys Arg
1               5                   10                  15

Arg Arg Arg

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
```

```
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (14)..(14)
<223> OTHER INFORMATION: AMP
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 9

Lys Arg Arg Arg Arg Cys Pro Leu Tyr Ile Ser Tyr Asp Pro Val Cys
1               5                   10                  15

Arg Arg Arg Arg
            20

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
```

```
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 10

Arg Arg Arg Arg Cys Pro Leu Tyr Ile Ser Tyr Asp Pro Val Cys Arg
1               5                   10                  15

Arg Arg Arg

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (11)..(11)
<223> OTHER INFORMATION: Cle
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 11

Lys Arg Arg Arg Arg Cys Pro Leu Tyr Ile Xaa Tyr Asp Pro Val Cys
1               5                   10                  15

Arg Arg Arg Arg
            20
```

```
<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 12

Lys Arg Arg Arg Arg Cys Pro Leu Tyr Ile Ser Tyr Asp Pro Ala Cys
1               5                   10                  15

Arg Arg Arg Arg
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: NMeArg
<220> FEATURE:
<221> NAME/KEY: MOD_RES
```

```
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: NMeArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: NMeArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: NMeArg

<400> SEQUENCE: 13

Lys Arg Arg Arg Arg Cys Pro Leu Tyr Ile Ser Tyr Asp Pro Val Cys
1               5                   10                  15

Arg Arg Arg Arg
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: 2Nal
<220> FEATURE:
<221> NAME/KEY: MOD_RES
<222> LOCATION: (11)..(11)
<223> OTHER INFORMATION: Cle
```

```
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 14

Lys Arg Arg Arg Arg Cys Pro Leu Xaa Ile Xaa Tyr Asp Pro Ala Cys
1               5                   10                  15

Arg Arg Arg Arg
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 15
```

```
Lys Arg Arg Arg Arg Cys Pro Leu Tyr Ile Ser Tyr Asp Pro Val Cys
1               5                   10                  15

Arg Arg Arg Arg
            20
```

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys(N3)
<220> FEATURE:
<221> NAME/KEY: MOD_RES
<222> LOCATION: (3)..(3)
<223> OTHER INFORMATION: Aeea
<220> FEATURE:
<221> NAME/KEY: MOD_RES
<222> LOCATION: (4)..(4)
<223> OTHER INFORMATION: DCys

<400> SEQUENCE: 16

```
Gly Lys Xaa Cys Pro Leu Tyr Ile Ser Tyr Asp Pro Val Cys Arg
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: F4tBu
<220> FEATURE:
<221> NAME/KEY: MOD_RES
<222> LOCATION: (10)..(10)
<223> OTHER INFORMATION: F4tBu

<400> SEQUENCE: 17

```
Lys Arg Arg Cys Pro Leu Phe Ile Ser Phe Asp Pro Val Cys Arg Arg
1               5                   10                  15
```

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (6)..(6)
<223> OTHER INFORMATION: DCys

```
<220> FEATURE:
<221> NAME/KEY: MOD_RES
<222> LOCATION: (9)..(9)
<223> OTHER INFORMATION: 2Nal

<400> SEQUENCE: 18

Lys Arg Arg Arg Arg Cys Pro Leu Xaa Ile Ser Tyr Asp Pro Val Cys
1               5                   10                  15

Arg Arg Arg Arg
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg
<220> FEATURE:
<221> NAME/KEY: MOD_RES
<222> LOCATION: (20)..(20)
<223> OTHER INFORMATION: DArg

<400> SEQUENCE: 19

Lys Arg Arg Arg Arg Cys Pro Leu Tyr Ile Ser Tyr Asp Pro Glu Cys
1               5                   10                  15

Arg Arg Arg Arg
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: DCys
<220> FEATURE:
<221> NAME/KEY: MOD_RES
<222> LOCATION: (14)..(14)
<223> OTHER INFORMATION: Lys(N3)
<220> FEATURE:
<221> NAME/KEY: MOD_RES
<222> LOCATION: (15)..(15)
<223> OTHER INFORMATION: Aeea

<400> SEQUENCE: 20

Cys Pro Leu Tyr Ile Ser Tyr Asp Pro Val Cys Arg Gly Lys Xaa
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (8)..(8)
<223> OTHER INFORMATION: Cha
<220> FEATURE:
<221> NAME/KEY: MOD_RES
<222> LOCATION: (9)..(9)
<223> OTHER INFORMATION: Cha

<400> SEQUENCE: 21

Arg Arg Cys Pro Leu Tyr Ile Ala Ala Asp Pro Val Cys Arg Arg
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (15)..(15)
<223> OTHER INFORMATION: Cha

<400> SEQUENCE: 22

Lys Arg Arg Arg Arg Cys Pro Leu Tyr Ile Ser Tyr Asp Pro Ala Cys
1               5                   10                  15

Arg Arg Arg Arg
            20

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (9)..(9)
<223> OTHER INFORMATION: Dbg

<400> SEQUENCE: 23

Lys Arg Arg Cys Pro Leu Tyr Ile Xaa Tyr Asp Pro Val Cys Arg Arg
1               5                   10                  15

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (11)..(11)
<223> OTHER INFORMATION: Cle

<400> SEQUENCE: 24

Lys Arg Arg Arg Arg Cys Pro Leu Tyr Ile Xaa Tyr Asp Pro Val Cys
1               5                   10                  15

Arg Arg Arg Arg
            20

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: hArg
<220> FEATURE:
<221> NAME/KEY: MOD_RES
<222> LOCATION: (3)..(3)
<223> OTHER INFORMATION: hArg
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (15)..(15)
```

```
<223> OTHER INFORMATION: hArg
<220> FEATURE:
<221> NAME/KEY: MOD_RES
<222> LOCATION: (16)..(16)
<223> OTHER INFORMATION: hArg

<400> SEQUENCE: 25

Lys Arg Arg Cys Pro Leu Xaa Ile Ser Tyr Asp Pro Val Cys Arg Arg
 1               5                  10                  15

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DLeu
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (7)..(7)
<223> OTHER INFORMATION: T3PhP
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DLeu
<220> FEATURE:
<221> NAME/KEY: MOD_RES
<222> LOCATION: (20)..(20)
<223> OTHER INFORMATION: DArg

<400> SEQUENCE: 26

Lys Arg Leu Leu Arg Cys Xaa Leu Tyr Ile Ser Tyr Asp Pro Val Cys
 1               5                  10                  15

Arg Leu Leu Arg
            20

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                              peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (5)..(5)
<223> OTHER INFORMATION: T3PhP
<220> FEATURE:
<221> NAME/KEY: MOD_RES
<222> LOCATION: (7)..(7)
<223> OTHER INFORMATION: Bip
<220> FEATURE:
<221> NAME/KEY: MOD_RES
<222> LOCATION: (15)..(15)
<223> OTHER INFORMATION: DArg
<220> FEATURE:
<221> NAME/KEY: MOD_RES
<222> LOCATION: (16)..(16)
<223> OTHER INFORMATION: DArg

<400> SEQUENCE: 27

Lys Arg Arg Cys Xaa Leu Xaa Ile Ser Tyr Asp Pro Val Cys Arg Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (5)..(5)
<223> OTHER INFORMATION: T34Me2cPP

<400> SEQUENCE: 28

Lys Arg Arg Cys Xaa Leu Tyr Ile Ser Tyr Asp Pro Val Cys Arg Arg
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
```

```
<222> LOCATION: (4)..(4)
<223> OTHER INFORMATION: DCys
<220> FEATURE:
<221> NAME/KEY: MOD_RES
<222> LOCATION: (9)..(9)
<223> OTHER INFORMATION: Aic

<400> SEQUENCE: 29

Lys Arg Arg Cys Pro Leu Tyr Ile Xaa Tyr Asp Pro Val Cys Arg Arg
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: hArg
<220> FEATURE:
<221> NAME/KEY: MOD_RES
<222> LOCATION: (3)..(3)
<223> OTHER INFORMATION: hArg
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (5)..(5)
<223> OTHER INFORMATION: T3PhP
<220> FEATURE:
<221> NAME/KEY: MOD_RES
<222> LOCATION: (15)..(15)
<223> OTHER INFORMATION: hArg
<220> FEATURE:
<221> NAME/KEY: MOD_RES
<222> LOCATION: (16)..(16)
<223> OTHER INFORMATION: hArg

<400> SEQUENCE: 30

Lys Arg Arg Cys Xaa Leu Tyr Ile Ser Tyr Asp Pro Val Cys Arg Arg
1               5                   10                  15

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DLeu
<220> FEATURE:
```

```
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: Bip
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DLeu
<220> FEATURE:
<221> NAME/KEY: MOD_RES
<222> LOCATION: (20)..(20)
<223> OTHER INFORMATION: DArg

<400> SEQUENCE: 31

Lys Arg Leu Leu Arg Cys Pro Leu Xaa Ile Ser Tyr Asp Pro Val Cys
1               5                   10                  15

Arg Leu Leu Arg
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DLeu
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: 2Nal
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
```

```
<223> OTHER INFORMATION: DLeu
<220> FEATURE:
<221> NAME/KEY: MOD_RES
<222> LOCATION: (19)..(19)
<223> OTHER INFORMATION: DLeu
<220> FEATURE:
<221> NAME/KEY: MOD_RES
<222> LOCATION: (20)..(20)
<223> OTHER INFORMATION: DArg

<400> SEQUENCE: 32

Lys Arg Leu Leu Arg Cys Pro Leu Xaa Ile Ser Tyr Asp Pro Val Cys
1               5                   10                  15

Arg Leu Leu Arg
            20

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: YCF3
<220> FEATURE:
<221> NAME/KEY: MOD_RES
<222> LOCATION: (10)..(10)
<223> OTHER INFORMATION: YCF3

<400> SEQUENCE: 33

Lys Arg Arg Cys Pro Leu Xaa Ile Ser Xaa Asp Pro Val Cys Arg Arg
1               5                   10                  15

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys

<400> SEQUENCE: 34

Arg Arg Arg Arg Cys Pro Leu Tyr Ile Ser Tyr Asp Pro Val Cys Arg
1               5                   10                  15

Arg Arg Arg

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (5)..(5)
<223> OTHER INFORMATION: T3PhP

<400> SEQUENCE: 35

Lys Arg Arg Cys Xaa Leu Tyr Ile Ser Tyr Asp Pro Val Cys Arg Arg
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (6)..(6)
<223> OTHER INFORMATION: BHL

<400> SEQUENCE: 36

Lys Arg Arg Cys Pro Xaa Tyr Ile Ser Tyr Asp Pro Val Cys Arg Arg
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DLeu
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: F4CF3
<220> FEATURE:
<221> NAME/KEY: MOD_RES
```

-continued

```
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DLeu
<220> FEATURE:
<221> NAME/KEY: MOD_RES
<222> LOCATION: (20)..(20)
<223> OTHER INFORMATION: DArg

<400> SEQUENCE: 37

Lys Arg Leu Leu Arg Cys Pro Leu Phe Ile Ser Tyr Asp Pro Val Cys
1               5                   10                  15

Arg Leu Leu Arg
            20

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (9)..(9)
<223> OTHER INFORMATION: Cle

<400> SEQUENCE: 38

Lys Arg Arg Cys Pro Leu Tyr Ile Xaa Tyr Asp Pro Val Cys Arg Arg
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (9)..(9)
<223> OTHER INFORMATION: 1Nal

<400> SEQUENCE: 39

Arg Arg Cys Pro Leu Tyr Ile Trp Xaa Asp Pro Val Cys Arg Arg
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (4)..(4)
<223> OTHER INFORMATION: T3PhP

<400> SEQUENCE: 40

Arg Arg Cys Xaa Leu Tyr Ile Ser Tyr Asp Pro Val Cys Arg Arg
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (10)..(10)
<223> OTHER INFORMATION: Bhg

<400> SEQUENCE: 41

Lys Arg Arg Cys Pro Leu Tyr Ile Ser Xaa Asp Pro Val Cys Arg Arg
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (9)..(9)
<223> OTHER INFORMATION: C8G

<400> SEQUENCE: 42

Lys Arg Arg Cys Pro Leu Tyr Ile Xaa Tyr Asp Pro Val Cys Arg Arg
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
```

```
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: YBzl

<400> SEQUENCE: 43

Lys Arg Arg Cys Pro Leu Tyr Ile Ser Tyr Asp Pro Val Cys Arg Arg
1               5                   10                  15

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (7)..(7)
<223> OTHER INFORMATION: T3OHP

<400> SEQUENCE: 44

Lys Arg Arg Arg Arg Cys Xaa Leu Tyr Ile Ser Tyr Asp Pro Val Cys
1               5                   10                  15

Arg Arg Arg Arg
            20

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (10)..(10)
<223> OTHER INFORMATION: 4Ial

<400> SEQUENCE: 45

Lys Arg Arg Cys Pro Leu Tyr Ile Ser Xaa Asp Pro Val Cys Arg Arg
1               5                   10                  15

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Lys(N3)
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (19)..(19)
<223> OTHER INFORMATION: Nle

<400> SEQUENCE: 46

Lys Arg Leu Leu Arg Cys Pro Leu Tyr Ile Ser Tyr Asp Pro Val Cys
1               5                   10                  15

Arg Leu Leu Arg
            20

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys

<400> SEQUENCE: 47

Lys Arg Arg Cys Pro Leu Tyr Ile Lys Tyr Asp Pro Val Cys Arg Arg
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (9)..(9)
<223> OTHER INFORMATION: Cha

<400> SEQUENCE: 48

Arg Arg Cys Pro Leu Tyr Ile Trp Ala Asp Pro Val Cys Arg Arg
1               5                   10                  15

<210> SEQ ID NO 49
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (6)..(6)
<223> OTHER INFORMATION: DCys
<220> FEATURE:
<221> NAME/KEY: MOD_RES
<222> LOCATION: (9)..(9)
<223> OTHER INFORMATION: 2Nal
<220> FEATURE:
<221> NAME/KEY: MOD_RES
<222> LOCATION: (15)..(15)
<223> OTHER INFORMATION: Chg

<400> SEQUENCE: 49

Lys Arg Leu Leu Arg Cys Pro Leu Xaa Ile Ser Trp Asp Pro Gly Cys
1               5                   10                  15

Arg Leu Leu Arg
            20

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (9)..(9)
<223> OTHER INFORMATION: Dip

<400> SEQUENCE: 50

Arg Arg Cys Pro Leu Tyr Ile Ser Xaa Asp Pro Val Cys Arg Arg
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: Bip
<220> FEATURE:
```

```
<221> NAME/KEY: MOD_RES
<222> LOCATION: (15)..(15)
<223> OTHER INFORMATION: DArg
<220> FEATURE:
<221> NAME/KEY: MOD_RES
<222> LOCATION: (16)..(16)
<223> OTHER INFORMATION: DArg

<400> SEQUENCE: 51

Lys Arg Arg Cys Pro Leu Xaa Ile Ser Tyr Asp Pro Val Cys Arg Arg
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: Bip

<400> SEQUENCE: 52

Lys Arg Arg Cys Pro Leu Xaa Ile Ser Tyr Asp Pro Val Cys Arg Arg
1               5                   10                  15

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (6)..(6)
<223> OTHER INFORMATION: DCys

<400> SEQUENCE: 53

Lys Arg Arg Arg Arg Cys Pro Leu Tyr Ile Ser Tyr Asp Pro Val Cys
1               5                   10                  15

Arg Arg Arg Arg
            20

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
```

```
<223> OTHER INFORMATION: DCys
<220> FEATURE:
<221> NAME/KEY: MOD_RES
<222> LOCATION: (7)..(7)
<223> OTHER INFORMATION: Tic

<400> SEQUENCE: 54

Lys Arg Arg Cys Pro Leu Xaa Ile Ser Tyr Asp Pro Val Cys Arg Arg
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys

<400> SEQUENCE: 55

Lys Arg Arg Cys Pro Leu Tyr Ile Arg Tyr Asp Pro Val Cys Arg Arg
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (6)..(6)
<223> OTHER INFORMATION: C8G

<400> SEQUENCE: 56

Lys Arg Arg Cys Pro Xaa Tyr Ile Ser Tyr Asp Pro Val Cys Arg Arg
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
```

```
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 57

Arg Glu Arg Arg Cys Pro Leu Tyr Ile Ser Tyr Asp Pro Val Cys Arg
1               5                   10                  15

Lys Arg Arg

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: hArg
<220> FEATURE:
<221> NAME/KEY: MOD_RES
<222> LOCATION: (3)..(3)
<223> OTHER INFORMATION: hArg
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (7)..(7)
<223> OTHER INFORMATION: 2Nal
<220> FEATURE:
<221> NAME/KEY: MOD_RES
<222> LOCATION: (15)..(15)
<223> OTHER INFORMATION: hArg
<220> FEATURE:
<221> NAME/KEY: MOD_RES
<222> LOCATION: (16)..(16)
<223> OTHER INFORMATION: hArg

<400> SEQUENCE: 58

Lys Arg Arg Cys Pro Leu Xaa Ile Ser Tyr Asp Pro Val Cys Arg Arg
1               5                   10                  15

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
```

```
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg

<400> SEQUENCE: 59

Lys Arg Arg Arg Cys Pro Leu Tyr Ile Ser Tyr Asp Pro Val Cys Arg
1               5                   10                  15

Arg Arg

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (8)..(8)
<223> OTHER INFORMATION: Nva
<220> FEATURE:
<221> NAME/KEY: MOD_RES
<222> LOCATION: (9)..(9)
<223> OTHER INFORMATION: 1Nal

<400> SEQUENCE: 60

Arg Arg Cys Pro Leu Tyr Ile Val Xaa Asp Pro Val Cys Arg Arg
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
```

-continued

```
<222> LOCATION: (13)..(13)
<223> OTHER INFORMATION: Bhg

<400> SEQUENCE: 61

Lys Arg Arg Cys Pro Leu Tyr Ile Ser Tyr Asp Pro Xaa Cys Arg Arg
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(N3)
<220> FEATURE:
<221> NAME/KEY: MOD_RES
<222> LOCATION: (3)..(3)
<223> OTHER INFORMATION: Aeea
<220> FEATURE:
<221> NAME/KEY: MOD_RES
<222> LOCATION: (4)..(4)
<223> OTHER INFORMATION: DCys

<400> SEQUENCE: 62

Gly Lys Xaa Cys Pro Leu Tyr Ile Ser Tyr Asp Pro Val Cys Arg
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (6)..(6)
<223> OTHER INFORMATION: Npg

<400> SEQUENCE: 63

Lys Arg Arg Cys Pro Xaa Tyr Ile Ser Tyr Asp Pro Val Cys Arg Arg
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (10)..(10)
```

<223> OTHER INFORMATION: DBhg

<400> SEQUENCE: 64

Lys Arg Arg Cys Pro Leu Tyr Ile Ser Xaa Asp Pro Val Cys Arg Arg
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
<222> LOCATION: (14)..(14)
<223> OTHER INFORMATION: Pen

<400> SEQUENCE: 65

Lys Arg Arg Cys Pro Leu Tyr Ile Ser Tyr Asp Pro Val Xaa Arg Arg
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (4)..(4)
<223> OTHER INFORMATION: DCys

<400> SEQUENCE: 66

Lys Arg Arg Cys Pro Leu Lys Ile Ser Tyr Asp Pro Val Cys Arg Arg
1               5                   10                  15

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Arg Arg Arg Cys Pro Leu Tyr Ile Ser Tyr Asp Pro Val Cys Arg
1               5                   10                  15

Arg Arg Arg

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (14)..(14)
<223> OTHER INFORMATION: Lys(5FAM)

<400> SEQUENCE: 68

Lys Arg Arg Arg Arg Cys Pro Leu Tyr Ile Ser Tyr Asp Lys Val Cys
1               5                   10                  15

Arg Arg Arg Arg
            20

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (11)..(11)
<223> OTHER INFORMATION: Lys(5FAM)

<400> SEQUENCE: 69

Arg Arg Cys Pro Leu Tyr Ile Ser Tyr Asp Lys Val Cys Arg Arg
1               5                   10                  15

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
```

-continued

```
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 70

Arg Arg Arg Arg Cys Pro Leu Xaa Ile Ser Tyr Asp Pro Val Cys Arg
1               5                   10                  15

Arg Arg Arg

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (10)..(10)
<223> OTHER INFORMATION: AMS
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 71

Arg Arg Arg Arg Cys Pro Leu Tyr Ile Ser Tyr Asp Pro Val Cys Arg
1               5                   10                  15

Arg Arg Arg

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
               peptide
<220> FEATURE:
<221> NAME/KEY: MOD_RES
<222> LOCATION: (2)..(2)
<223> OTHER INFORMATION: Aeea
<220> FEATURE:
<221> NAME/KEY: MOD_RES
<222> LOCATION: (5)..(5)
<223> OTHER INFORMATION: DCys

<400> SEQUENCE: 72

Gly Xaa Arg Arg Cys Pro Leu Tyr Ile Ser Tyr Asp Pro Val Cys Arg
1               5                   10                  15

Arg

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (6)..(6)
<223> OTHER INFORMATION: T3PhP
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 73

Arg Arg Arg Arg Cys Xaa Leu Tyr Ile Ser Tyr Asp Pro Val Cys Arg
1               5                   10                  15

Arg Arg Arg

<210> SEQ ID NO 74
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal
<220> FEATURE:
<221> NAME/KEY: MOD_RES
<222> LOCATION: (14)..(14)
<223> OTHER INFORMATION: Cha
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 74

Arg Arg Arg Arg Cys Pro Leu Xaa Ile Ser Tyr Asp Pro Ala Cys Arg
1               5                   10                  15

Arg Arg Arg

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
```

```
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal
<220> FEATURE:
<221> NAME/KEY: MOD_RES
<222> LOCATION: (14)..(14)
<223> OTHER INFORMATION: Chg
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 75

Arg Arg Arg Arg Cys Pro Leu Xaa Ile Ser Trp Asp Pro Gly Cys Arg
1               5                   10                  15

Arg Arg Arg

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: NMeArg
<220> FEATURE:
<221> NAME/KEY: MOD_RES
<222> LOCATION: (3)..(3)
<223> OTHER INFORMATION: NMeArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (17)..(17)
<223> OTHER INFORMATION: NMeArg
<220> FEATURE:
<221> NAME/KEY: MOD_RES
<222> LOCATION: (19)..(19)
<223> OTHER INFORMATION: NMeArg

<400> SEQUENCE: 76

Arg Arg Arg Arg Cys Pro Leu Tyr Ile Ser Tyr Asp Pro Val Cys Arg
1               5                   10                  15

Arg Arg Arg

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (13)..(13)
<223> OTHER INFORMATION: AMP
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 77

Arg Arg Arg Arg Cys Pro Leu Tyr Ile Ser Tyr Asp Pro Val Cys Arg
1               5                   10                  15

Arg Arg Arg

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (10)..(10)
```

```
<223> OTHER INFORMATION: Cle
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 78

Arg Arg Arg Arg Cys Pro Leu Tyr Ile Xaa Tyr Asp Pro Val Cys Arg
1               5                   10                  15

Arg Arg Arg

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (14)..(14)
<223> OTHER INFORMATION: Cha
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 79

Arg Arg Arg Arg Cys Pro Leu Tyr Ile Ser Tyr Asp Pro Ala Cys Arg
1               5                   10                  15
```

Arg Arg Arg

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: NMeArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: NMeArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: NMeArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: NMeArg

<400> SEQUENCE: 80

Arg Arg Arg Arg Cys Pro Leu Tyr Ile Ser Tyr Asp Pro Val Cys Arg
1               5                   10                  15

Arg Arg Arg

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:

```
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal
<220> FEATURE:
<221> NAME/KEY: MOD_RES
<222> LOCATION: (10)..(10)
<223> OTHER INFORMATION: Cle
<220> FEATURE:
<221> NAME/KEY: MOD_RES
<222> LOCATION: (14)..(14)
<223> OTHER INFORMATION: Cha
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 81

Arg Arg Arg Arg Cys Pro Leu Xaa Ile Xaa Tyr Asp Pro Ala Cys Arg
1               5                   10                  15

Arg Arg Arg

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
```

```
<220> FEATURE:
<221> NAME/KEY: MOD_RES
<222> LOCATION: (19)..(19)
<223> OTHER INFORMATION: DArg

<400> SEQUENCE: 82

Arg Arg Arg Arg Cys Pro Leu Tyr Ile Ser Tyr Asp Pro Val Cys Arg
1               5                   10                  15

Arg Arg Arg

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aeea
<220> FEATURE:
<221> NAME/KEY: MOD_RES
<222> LOCATION: (3)..(3)
<223> OTHER INFORMATION: DCys

<400> SEQUENCE: 83

Gly Xaa Cys Pro Leu Tyr Ile Ser Tyr Asp Pro Val Cys Arg
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: F4tBu
<220> FEATURE:
<221> NAME/KEY: MOD_RES
<222> LOCATION: (9)..(9)
<223> OTHER INFORMATION: F4tBu

<400> SEQUENCE: 84

Arg Arg Cys Pro Leu Phe Ile Ser Phe Asp Pro Val Cys Arg Arg
1               5                   10                  15

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal

<400> SEQUENCE: 85
```

-continued

```
Arg Arg Arg Arg Cys Pro Leu Xaa Ile Ser Tyr Asp Pro Val Cys Arg
1               5                   10                  15

Arg Arg Arg

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg
<220> FEATURE:
<221> NAME/KEY: MOD_RES
<222> LOCATION: (18)..(18)
<223> OTHER INFORMATION: DArg
<220> FEATURE:
<221> NAME/KEY: MOD_RES
<222> LOCATION: (19)..(19)
<223> OTHER INFORMATION: DArg

<400> SEQUENCE: 86

Arg Arg Arg Arg Cys Pro Leu Tyr Ile Ser Tyr Asp Pro Glu Cys Arg
1               5                   10                  15

Arg Arg Arg

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: DCys
<220> FEATURE:
<221> NAME/KEY: MOD_RES
<222> LOCATION: (14)..(14)
<223> OTHER INFORMATION: Aeea

<400> SEQUENCE: 87

Cys Pro Leu Tyr Ile Ser Tyr Asp Pro Val Cys Arg Gly Xaa
1               5                   10
```

```
<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (14)..(14)
<223> OTHER INFORMATION: Cha

<400> SEQUENCE: 88

Arg Arg Arg Arg Cys Pro Leu Tyr Ile Ser Tyr Asp Pro Ala Cys Arg
1               5                   10                  15

Arg Arg Arg

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (8)..(8)
<223> OTHER INFORMATION: Dbg

<400> SEQUENCE: 89

Arg Arg Cys Pro Leu Tyr Ile Xaa Tyr Asp Pro Val Cys Arg Arg
1               5                   10                  15

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (10)..(10)
<223> OTHER INFORMATION: Cle

<400> SEQUENCE: 90

Arg Arg Arg Arg Cys Pro Leu Tyr Ile Xaa Tyr Asp Pro Val Cys Arg
1               5                   10                  15

Arg Arg Arg

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: hArg
<220> FEATURE:
<221> NAME/KEY: MOD_RES
<222> LOCATION: (2)..(2)
<223> OTHER INFORMATION: hArg
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (14)..(14)
<223> OTHER INFORMATION: hArg
<220> FEATURE:
<221> NAME/KEY: MOD_RES
<222> LOCATION: (15)..(15)
<223> OTHER INFORMATION: hArg

<400> SEQUENCE: 91

Arg Arg Cys Pro Leu Xaa Ile Ser Tyr Asp Pro Val Cys Arg Arg
1               5                   10                  15

<210> SEQ ID NO 92
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DLeu
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (6)..(6)
<223> OTHER INFORMATION: T3PhP
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DLeu
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DArg

<400> SEQUENCE: 92
```

Arg Leu Leu Arg Cys Xaa Leu Tyr Ile Ser Tyr Asp Pro Val Cys Arg
1               5                   10                  15

Leu Leu Arg

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (4)..(4)
<223> OTHER INFORMATION: T3PhP
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (14)..(14)
<223> OTHER INFORMATION: DArg
<220> FEATURE:
<221> NAME/KEY: MOD_RES
<222> LOCATION: (15)..(15)
<223> OTHER INFORMATION: DArg

<400> SEQUENCE: 93

Arg Arg Cys Xaa Leu Xaa Ile Ser Tyr Asp Pro Val Cys Arg Arg
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (4)..(4)
<223> OTHER INFORMATION: T34Me2cPP

<400> SEQUENCE: 94

Arg Arg Cys Xaa Leu Tyr Ile Ser Tyr Asp Pro Val Cys Arg Arg
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (8)..(8)
<223> OTHER INFORMATION: Aic

<400> SEQUENCE: 95

Arg Arg Cys Pro Leu Tyr Ile Xaa Tyr Asp Pro Val Cys Arg Arg
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hArg
<220> FEATURE:
<221> NAME/KEY: MOD_RES
<222> LOCATION: (2)..(2)
<223> OTHER INFORMATION: hArg
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (4)..(4)
<223> OTHER INFORMATION: T3PhP
<220> FEATURE:
<221> NAME/KEY: MOD_RES
<222> LOCATION: (14)..(14)
<223> OTHER INFORMATION: hArg
<220> FEATURE:
<221> NAME/KEY: MOD_RES
<222> LOCATION: (15)..(15)
<223> OTHER INFORMATION: hArg

<400> SEQUENCE: 96

Arg Arg Cys Xaa Leu Tyr Ile Ser Tyr Asp Pro Val Cys Arg Arg
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DLeu
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
```

```
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DLeu
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DArg

<400> SEQUENCE: 97

Arg Leu Leu Arg Cys Pro Leu Xaa Ile Ser Tyr Asp Pro Val Cys Arg
1               5                   10                  15

Leu Leu Arg

<210> SEQ ID NO 98
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DLeu
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DLeu
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DArg

<400> SEQUENCE: 98
```

Arg Leu Leu Arg Cys Pro Leu Xaa Ile Ser Tyr Asp Pro Val Cys Arg
1               5                   10                  15

Leu Leu Arg

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: YCF3
<220> FEATURE:
<221> NAME/KEY: MOD_RES
<222> LOCATION: (9)..(9)
<223> OTHER INFORMATION: YCF3

<400> SEQUENCE: 99

Arg Arg Cys Pro Leu Xaa Ile Ser Xaa Asp Pro Val Cys Arg Arg
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (4)..(4)
<223> OTHER INFORMATION: T3PhP

<400> SEQUENCE: 100

Arg Arg Cys Xaa Leu Tyr Ile Ser Tyr Asp Pro Val Cys Arg Arg
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (5)..(5)
<223> OTHER INFORMATION: BHL

<400> SEQUENCE: 101

Arg Arg Cys Pro Xaa Tyr Ile Ser Tyr Asp Pro Val Cys Arg Arg
1               5                   10                  15

<210> SEQ ID NO 102
<211> LENGTH: 19
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DLeu
<220> FEATURE:
<221> NAME/KEY: MOD_RES
<222> LOCATION: (3)..(3)
<223> OTHER INFORMATION: DLeu
<220> FEATURE:
<221> NAME/KEY: MOD_RES
<222> LOCATION: (4)..(4)
<223> OTHER INFORMATION: DArg
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: F4CF3
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DLeu
<220> FEATURE:
<221> NAME/KEY: MOD_RES
<222> LOCATION: (18)..(18)
<223> OTHER INFORMATION: DLeu
<220> FEATURE:
<221> NAME/KEY: MOD_RES
<222> LOCATION: (19)..(19)
<223> OTHER INFORMATION: DArg

<400> SEQUENCE: 102

Arg Leu Leu Arg Cys Pro Leu Phe Ile Ser Tyr Asp Pro Val Cys Arg
1               5                   10                  15

Leu Leu Arg

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (8)..(8)
<223> OTHER INFORMATION: Cle

<400> SEQUENCE: 103

Arg Arg Cys Pro Leu Tyr Ile Xaa Tyr Asp Pro Val Cys Arg Arg
1               5                   10                  15

<210> SEQ ID NO 104
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (9)..(9)
<223> OTHER INFORMATION: Bhg

<400> SEQUENCE: 104

Arg Arg Cys Pro Leu Tyr Ile Ser Xaa Asp Pro Val Cys Arg Arg
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (8)..(8)
<223> OTHER INFORMATION: C8G

<400> SEQUENCE: 105

Arg Arg Cys Pro Leu Tyr Ile Xaa Tyr Asp Pro Val Cys Arg Arg
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: YBzl

<400> SEQUENCE: 106

Arg Arg Cys Pro Leu Tyr Ile Ser Tyr Asp Pro Val Cys Arg Arg
1               5                   10                  15

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (6)..(6)
<223> OTHER INFORMATION: T3OHP

<400> SEQUENCE: 107
```

Arg Arg Arg Arg Cys Xaa Leu Tyr Ile Ser Tyr Asp Pro Val Cys Arg
1               5                   10                  15

Arg Arg Arg

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (9)..(9)
<223> OTHER INFORMATION: 4Ial

<400> SEQUENCE: 108

Arg Arg Cys Pro Leu Tyr Ile Ser Xaa Asp Pro Val Cys Arg Arg
1               5                   10                  15

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (17)..(17)
<223> OTHER INFORMATION: Nle
<220> FEATURE:
<221> NAME/KEY: MOD_RES
<222> LOCATION: (18)..(18)
<223> OTHER INFORMATION: Nle

<400> SEQUENCE: 109

Arg Leu Leu Arg Cys Pro Leu Tyr Ile Ser Tyr Asp Pro Val Cys Arg
1               5                   10                  15

Leu Leu Arg

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys

<400> SEQUENCE: 110

Arg Arg Cys Pro Leu Tyr Ile Lys Tyr Asp Pro Val Cys Arg Arg
1               5                   10                  15

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (8)..(8)
<223> OTHER INFORMATION: 2Nal
<220> FEATURE:
<221> NAME/KEY: MOD_RES
<222> LOCATION: (14)..(14)
<223> OTHER INFORMATION: Chg

<400> SEQUENCE: 111

Arg Leu Leu Arg Cys Pro Leu Xaa Ile Ser Trp Asp Pro Gly Cys Arg
1               5                   10                  15

Leu Leu Arg

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (14)..(14)
<223> OTHER INFORMATION: DArg
<220> FEATURE:
<221> NAME/KEY: MOD_RES
<222> LOCATION: (15)..(15)
<223> OTHER INFORMATION: DArg

<400> SEQUENCE: 112

Arg Arg Cys Pro Leu Xaa Ile Ser Tyr Asp Pro Val Cys Arg Arg
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: Bip

<400> SEQUENCE: 113

Arg Arg Cys Pro Leu Xaa Ile Ser Tyr Asp Pro Val Cys Arg Arg
1               5                   10                  15

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: DCys

<400> SEQUENCE: 114

Arg Arg Arg Arg Cys Pro Leu Tyr Ile Ser Tyr Asp Pro Val Cys Arg
1               5                   10                  15

Arg Arg Arg

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: Tic

<400> SEQUENCE: 115

Arg Arg Cys Pro Leu Xaa Ile Ser Tyr Asp Pro Val Cys Arg Arg
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys

<400> SEQUENCE: 116

Arg Arg Cys Pro Leu Tyr Ile Arg Tyr Asp Pro Val Cys Arg Arg
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (5)..(5)
<223> OTHER INFORMATION: C8G

<400> SEQUENCE: 117

Arg Arg Cys Pro Xaa Tyr Ile Ser Tyr Asp Pro Val Cys Arg Arg
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hArg
<220> FEATURE:
<221> NAME/KEY: MOD_RES
<222> LOCATION: (2)..(2)
<223> OTHER INFORMATION: hArg
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (6)..(6)
<223> OTHER INFORMATION: 2Nal
<220> FEATURE:
<221> NAME/KEY: MOD_RES
<222> LOCATION: (14)..(14)
<223> OTHER INFORMATION: hArg
<220> FEATURE:
<221> NAME/KEY: MOD_RES
<222> LOCATION: (15)..(15)
<223> OTHER INFORMATION: hArg

<400> SEQUENCE: 118

Arg Arg Cys Pro Leu Xaa Ile Ser Tyr Asp Pro Val Cys Arg Arg
1               5                   10                  15

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DArg
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DCys
<220> FEATURE:
<221> NAME/KEY: MOD_RES
```

```
<222> LOCATION: (15)..(15)
<223> OTHER INFORMATION: DArg
<220> FEATURE:
<221> NAME/KEY: MOD_RES
<222> LOCATION: (16)..(16)
<223> OTHER INFORMATION: DArg
<220> FEATURE:
<221> NAME/KEY: MOD_RES
<222> LOCATION: (17)..(17)
<223> OTHER INFORMATION: DArg

<400> SEQUENCE: 119

Arg Arg Arg Cys Pro Leu Tyr Ile Ser Tyr Asp Pro Val Cys Arg Arg
1               5                   10                  15

Arg

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (12)..(12)
<223> OTHER INFORMATION: Bhg

<400> SEQUENCE: 120

Arg Arg Cys Pro Leu Tyr Ile Ser Tyr Asp Pro Xaa Cys Arg Arg
1               5                   10              15

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aeea
<220> FEATURE:
<221> NAME/KEY: MOD_RES
<222> LOCATION: (3)..(3)
<223> OTHER INFORMATION: DCys

<400> SEQUENCE: 121

Gly Xaa Cys Pro Leu Tyr Ile Ser Tyr Asp Pro Val Cys Arg
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (5)..(5)
<223> OTHER INFORMATION: Npg
```

-continued

```
<400> SEQUENCE: 122

Arg Arg Cys Pro Xaa Tyr Ile Ser Tyr Asp Pro Val Cys Arg Arg
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (9)..(9)
<223> OTHER INFORMATION: DBhg

<400> SEQUENCE: 123

Arg Arg Cys Pro Leu Tyr Ile Ser Xaa Asp Pro Val Cys Arg Arg
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys
<220> FEATURE:
<221> NAME/KEY: MOD_RES
<222> LOCATION: (13)..(13)
<223> OTHER INFORMATION: Pen

<400> SEQUENCE: 124

Arg Arg Cys Pro Leu Tyr Ile Ser Tyr Asp Pro Val Xaa Arg Arg
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: DCys

<400> SEQUENCE: 125

Arg Arg Cys Pro Leu Lys Ile Ser Tyr Asp Pro Val Cys Arg Arg
1               5                   10                  15

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-Arg, D-Arg, L-homoArg, N-Me-L-Arg, L-Glu,
```

```
      L-Lys, L-Gly-Aeea, L-Gly-L-Lys(N3)-Aeea, or absent
<220> FEATURE:
<221> NAME/KEY: MOD_RES
<222> LOCATION: (2)..(2)
<223> OTHER INFORMATION: L-Arg, D-Arg, L-homoArg, N-Me-L-Arg, L-Leu,
      D-Leu, L-Nle, L-Trp, L-Phe, L-Ala, L-Bip, L-Phe(4-CO2H), L-Glu,
      L-Lys, (L-Arg)3, (D-Arg)3, (L-homoArg)3, (L-Arg)4, (D-Arg)4,
      (L-homoArg)4, or absent
<220> FEATURE:
<221> NAME/KEY: MOD_RES
<222> LOCATION: (3)..(3)
<223> OTHER INFORMATION: L-Arg, D-Arg, L-homoArg, N-Me-L-Arg, L-Leu,
      D-Leu, L-Nle, L-Trp, L-Phe, L-Ala, L-Bip, L-Phe(4-CO2H), L-Glu,
      L-Lys, (L-Arg)3, (D-Arg)3, (L-homoArg)3, (L-Arg)4, (D-Arg)4,
      (L-homoArg)4, or absent
<220> FEATURE:
<221> NAME/KEY: MOD_RES
<222> LOCATION: (4)..(4)
<223> OTHER INFORMATION: L-Arg, D-Arg, L-homoArg, N-Me-L-Arg, L-Glu,
      L-Lys, L-Gly-Aeea, L-Gly-L-Lys(N3)-Aeea, or absent
<220> FEATURE:
<221> NAME/KEY: MOD_RES
<222> LOCATION: (5)..(5)
<223> OTHER INFORMATION: DCys
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: L-Arg, D-Arg, L-homoArg, N-Me-L-Arg, L-Glu,
      L-Lys, L-Gly-Aeea, L-Gly-L-Lys(N3)-Aeea, or absent
<220> FEATURE:
<221> NAME/KEY: MOD_RES
<222> LOCATION: (17)..(17)
<223> OTHER INFORMATION: L-Arg, D-Arg, L-homoArg, N-Me-L-Arg, L-Leu,
      D-Leu, L-Nle, L-Trp, L-Phe, L-Ala, L-Bip, L-Phe(4-CO2H), L-Glu,
      L-Lys, (L-Arg)3, (D-Arg)3, (L-homoArg)3, (L-Arg)4, (D-Arg)4,
      (L-homoArg)4, or absent
<220> FEATURE:
<221> NAME/KEY: MOD_RES
<222> LOCATION: (18)..(18)
<223> OTHER INFORMATION: L-Arg, D-Arg, L-homoArg, N-Me-L-Arg, L-Leu,
      D-Leu, L-Nle, L-Trp, L-Phe, L-Ala, L-Bip, L-Phe(4-CO2H), L-Glu,
      L-Lys, (L-Arg)3, (D-Arg)3, (L-homoArg)3, (L-Arg)4, (D-Arg)4,
      (L-homoArg)4, or absent
<220> FEATURE:
<221> NAME/KEY: MOD_RES
<222> LOCATION: (19)..(19)
<223> OTHER INFORMATION: L-Arg, D-Arg, L-homoArg, N-Me-L-Arg, L-Glu,
      L-Lys, L-Gly-Aeea, L-Gly-L-Lys(N3)-Aeea, or absent

<400> SEQUENCE: 126
```

```
Xaa Xaa Xaa Xaa Cys Xaa Xaa Xaa Leu Xaa Xaa Asp Pro Xaa Xaa Xaa
1               5                   10                  15

Xaa Xaa Xaa

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be present

<400> SEQUENCE: 127

Tyr Gly Lys Lys Lys Arg Arg Gln Arg Arg Arg
1               5                   10

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Gln Ile Lys Ile Trp Phe Gln Asn Arg Arg Met Lys Trp Lys Lys
1               5                   10                  15

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(9)
<223> OTHER INFORMATION: This sequence may encompass 5, 8, or 9 residues

<400> SEQUENCE: 129

Arg Arg Arg Arg Arg Arg Arg Arg Arg
1               5

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<221> NAME/KEY: MOD_RES
<222> LOCATION: (2)..(2)
<223> OTHER INFORMATION: DPhe
<220> FEATURE:
<221> NAME/KEY: MOD_RES
<222> LOCATION: (3)..(3)
<223> OTHER INFORMATION: 2Nal
<220> FEATURE:
<221> NAME/KEY: MOD_RES
<222> LOCATION: (5)..(5)
<223> OTHER INFORMATION: DArg
<220> FEATURE:
<221> NAME/KEY: MOD_RES
<222> LOCATION: (7)..(7)
<223> OTHER INFORMATION: DArg

<400> SEQUENCE: 131

Phe Phe Xaa Arg Arg Arg Arg Gln
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Leu Ile Tyr Leu Arg Leu Leu Arg
1               5

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Val Arg Leu Pro Pro Pro Val Arg Leu Pro Pro Pro Val Arg Leu Pro
1               5                   10                  15

Pro Pro

<210> SEQ ID NO 134
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Cys Arg Arg Arg Gln Arg Arg Lys Lys Arg Gly Gly Asp Ile Met Gly
1               5                   10                  15

Glu Trp Gly Asn Glu Ile Phe Gly Ala Ile Ala Gly Phe Leu Gly
            20                  25                  30

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 135

Tyr Ala Arg Val Arg Arg Gly Pro Arg Arg
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Arg Arg Arg Pro Arg Arg Thr Thr Arg Arg Arg
1               5                   10

<210> SEQ ID NO 137
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 138
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Lys Ala Leu Leu Ala His Ala Leu His Leu Leu Ala Leu Leu Ala
1               5                   10                  15

Leu His Leu Ala His Ala Leu Lys Lys Ala
            20                  25

<210> SEQ ID NO 139
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Lys Ala Leu Leu His Ala Ala Leu Ala His Leu Leu Ala Leu Ala
1               5                   10                  15

His His Leu Leu Ala Leu Leu Lys Lys Ala
            20                  25

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 140

Val Ser Arg Arg Arg Arg Arg Gly Gly Arg Arg Arg Arg
1               5                   10

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Gly Asp Asp Tyr Lys
1               5

<210> SEQ ID NO 142
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DPhe
<220> FEATURE:
<221> NAME/KEY: MOD_RES
<222> LOCATION: (3)..(3)
<223> OTHER INFORMATION: 2Nal
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: DArg(Pbf)
<220> FEATURE:
<221> NAME/KEY: MOD_RES
<222> LOCATION: (6)..(6)
<223> OTHER INFORMATION: Arg(Pbf)
<220> FEATURE:
<221> NAME/KEY: MOD_RES
<222> LOCATION: (7)..(7)
<223> OTHER INFORMATION: DArg(Pbf)
<220> FEATURE:
<221> NAME/KEY: MOD_RES
<222> LOCATION: (8)..(8)
<223> OTHER INFORMATION: gamma-Glu(alpha-OAll)
<220> FEATURE:
<221> NAME/KEY: MOD_RES
<222> LOCATION: (10)..(10)
<223> OTHER INFORMATION: Lys(N3)
<220> FEATURE:
<221> NAME/KEY: MOD_RES
<222> LOCATION: (11)..(11)
<223> OTHER INFORMATION: Aeea
<220> FEATURE:
<221> NAME/KEY: MOD_RES
<222> LOCATION: (12)..(12)
<223> OTHER INFORMATION: Arg(Pbf)
<220> FEATURE:
<221> NAME/KEY: MOD_RES
<222> LOCATION: (13)..(13)
<223> OTHER INFORMATION: Arg(Pbf)
<220> FEATURE:
<221> NAME/KEY: MOD_RES
<222> LOCATION: (14)..(14)
<223> OTHER INFORMATION: DCys(Trt)
<220> FEATURE:
<221> NAME/KEY: MOD_RES
<222> LOCATION: (17)..(17)
<223> OTHER INFORMATION: Tyr(OtBu)
```

```
<220> FEATURE:
<221> NAME/KEY: MOD_RES
<222> LOCATION: (19)..(19)
<223> OTHER INFORMATION: Ser(OtBu)
<220> FEATURE:
<221> NAME/KEY: MOD_RES
<222> LOCATION: (20)..(20)
<223> OTHER INFORMATION: Tyr(OtBu)
<220> FEATURE:
<221> NAME/KEY: MOD_RES
<222> LOCATION: (21)..(21)
<223> OTHER INFORMATION: Asp(OtBu)
<220> FEATURE:
<221> NAME/KEY: MOD_RES
<222> LOCATION: (24)..(24)
<223> OTHER INFORMATION: Cys(Trt)
<220> FEATURE:
<221> NAME/KEY: MOD_RES
<222> LOCATION: (25)..(25)
<223> OTHER INFORMATION: Arg(Pbf)
<220> FEATURE:
<221> NAME/KEY: MOD_RES
<222> LOCATION: (26)..(26)
<223> OTHER INFORMATION: Arg(Pbf)

<400> SEQUENCE: 142

Phe Phe Xaa Arg Arg Arg Arg Glu Gly Lys Xaa Arg Arg Cys Pro Leu
1               5                   10                  15

Tyr Ile Ser Tyr Asp Pro Val Cys Arg Arg
            20                  25

<210> SEQ ID NO 143
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Gly Gly Gly Met Thr Glu Tyr Lys Leu Val Val Val Gly Ala Asp
1               5                   10                  15

Gly Val Gly Lys Ser Ala Leu Thr Ile Gln Leu Ile Gln Asn His Phe
            20                  25                  30

Val Asp Glu Tyr Asp Pro Thr Ile Glu Asp Ser Tyr Arg Lys Gln Val
        35                  40                  45

Val Ile Asp Gly Glu Thr Cys Leu Leu Asp Ile Leu Asp Thr Ala Gly
    50                  55                  60

Gln Glu Glu Tyr Ser Ala Met Arg Asp Gln Tyr Met Arg Thr Gly Glu
65                  70                  75                  80

Gly Phe Leu Cys Val Phe Ala Ile Asn Asn Thr Lys Ser Phe Glu Asp
                85                  90                  95

Ile His His Tyr Arg Glu Gln Ile Lys Arg Val Lys Asp Ser Glu Asp
            100                 105                 110

Val Pro Met Val Leu Val Gly Asn Lys Cys Asp Leu Pro Ser Arg Thr
        115                 120                 125

Val Asp Thr Lys Gln Ala Gln Asp Leu Ala Arg Ser Tyr Gly Ile Pro
    130                 135                 140

Phe Ile Glu Thr Ser Ala Lys Thr Arg Gln Gly Val Asp Asp Ala Phe
145                 150                 155                 160

Tyr Thr Leu Val Arg Glu Ile Arg Lys His Lys Glu Lys
                165                 170

<210> SEQ ID NO 144
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Gly Gly Gly Leu Pro Glu Thr Gly Gly
1               5                   10

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N3)
<220> FEATURE:
<221> NAME/KEY: MOD_RES
<222> LOCATION: (2)..(2)
<223> OTHER INFORMATION: Beta-Ala
<220> FEATURE:
<221> NAME/KEY: MOD_RES
<222> LOCATION: (6)..(6)
<223> OTHER INFORMATION: (R)-2-(7'-Octenyl)alanine or alpha-Me-D-Gly(7'-
      octenyl)-OH
<220> FEATURE:
<221> NAME/KEY: MOD_RES
<222> LOCATION: (12)..(12)
<223> OTHER INFORMATION: Cba
<220> FEATURE:
<221> NAME/KEY: MOD_RES
<222> LOCATION: (13)..(13)
<223> OTHER INFORMATION: (S)-alpha-(4'-Pentenyl)alanine or alpha-Me-L-
      Gly(4'-pentenyl)-OH

<400> SEQUENCE: 145

Lys Ala Leu Thr Phe Xaa Glu Tyr Trp Ala Gln Ala Xaa Ser Ala Ala
1               5                   10                  15

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(N3)
<220> FEATURE:
<221> NAME/KEY: MOD_RES
<222> LOCATION: (11)..(11)
<223> OTHER INFORMATION: (R)-2-(7'-Octenyl)alanine or alpha-Me-D-Gly(7'-
      octenyl)-OH
<220> FEATURE:
<221> NAME/KEY: MOD_RES
<222> LOCATION: (18)..(18)
<223> OTHER INFORMATION: (S)-alpha-(4'-Pentenyl)alanine or alpha-Me-L-
      Gly(4'-pentenyl)-OH

<400> SEQUENCE: 146

Glu Glu Glu Lys Ser Gly Ser Thr Ser Phe Xaa Glu Tyr Trp Ala Leu
1               5                   10                  15

Leu Xaa Glu Glu Glu
            20
```

MACROCYCLIC PEPTIDES AS POTENT INHIBITORS OF K-RAS G12D MUTANT

CROSS-REFERENCE TO RELATED APPLICATIONS

This application is a § 371 National Phase Application of International Application No. PCT/US2020/065009, filed on Dec. 15, 2020, which claims priority to U.S. Provisional Patent Application No. 62/949,705, filed on Dec. 18, 2019, the content of each of which is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 15, 2020, is named 24888WOPCT-SEQLIST-15OCT2020 and is 84.1 Kb in size.

FIELD OF THE INVENTION

The present invention relates to certain macrocyclic peptides and pharmaceutically acceptable salts thereof that inhibit the G12D mutant of Kirsten rat sarcoma (K-Ras) protein and are expected to have utility as therapeutic agents, for example, for treatment of cancer. The present application also relates to pharmaceutical compounds containing such compounds as well as methods of using the compounds for treating cancer.

BACKGROUND OF THE INVENTION

Ras proteins are membrane-associated guanine nucleotide-binding proteins which function as molecular switches. Ras proteins function as components of signalling pathways transmitting signals from cell-surface receptors to regulate cellular proliferation, survival and differentiation. Ras proteins cycle between an inactive GDP-bound state and an active GTP-bound state.

Exchange of a glycine for an aspartate at residue 12 of RAS (the G12D mutation) results from a gain-of-function mutation commonly found in RAS gene. The K-Ras(G12D) mutation appears frequently in certain cancer types including pancreatic ductal adenocarcinoma, colorectal cancer and lung adenocarcinoma. Pancreatic ductal adenocarcinoma is particularly significant. This cancer type represents a malignancy having a 5-year survival rate of less than 8%, and is also the fourth leading cause of cancer-related deaths in the western world. See Schneeweis C. et al., *Small GTPases* 2018; 9(6) 457-464.

Recently, Sakamoto et al., in *Biochemical and Biophysical Research Communications* 2017; 484; 605-611 disclosed the discovery of the cyclic peptide KRpep-2d (SEQ ID NO: 67) by screening random peptide libraries displayed on T7 phage against recombinant biotinylated K-Ras(G12D) immobilized onto streptavidin magnetic beads and subtracting phages bound to wild type K-Ras in a phage-panning process followed by affinity enhancement with a semi-random library. The publication discloses that KRpep-2d potently inhibited the SOS1-mediated GDP-GTP exchange with G12D-mutant selectivity against G12C and wild-type K-Ras variants. KRpep-2d reduced phosphorylation levels of ERK1/2, which is a signal transduction pathway downstream of K-Ras, and also suppressed cell proliferation of A427 cells (which contain the K-Ras(G12D) mutation) in a dose-dependent manner.

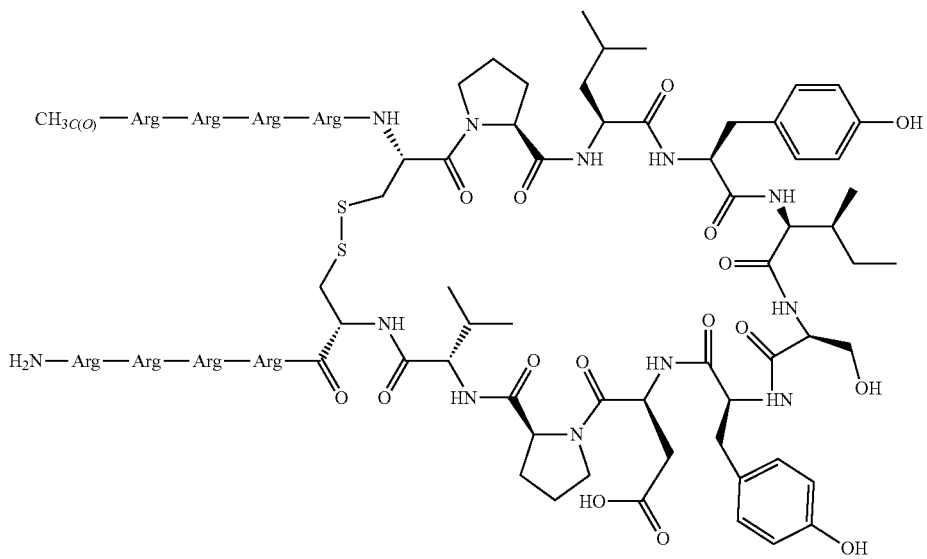

KRpep-2d (SEQ ID NO: 67)

Unfortunately, while KRpep-2d possessed severable desirable properties, the publication concludes that its efficacy was not sufficient for in vivo studies.

Accordingly, while progress has been made in designing K-Ras(G12D) inhibitors, there remains a need in the art for improved inhibitors that would lead to more effective in vivo activity, as well as methods for using such inhibitors for the treatment of cancer.

SUMMARY OF THE INVENTION

The present invention relates to compounds with potent binding affinity for K-Ras(G12D), prolonged metabolic stability, enhanced cell permeability, and potent cellular activity and may be valuable pharmaceutically active compounds for the treatment of cancer. Other K-Ras mutants may be inhibited by the compounds disclosed in the present application. The compounds of Formula (I) (SEQ ID. NO: 126)

cell permeability as a result of its hydrophilic character and the disulfide bridge (which may be labile under reducing conditions such a occur in the cytosol.

The compounds of Formula (I) incorporate an —S-alkylene-S— bridge (e.g., a thioacetal bridge) in place of the (I)

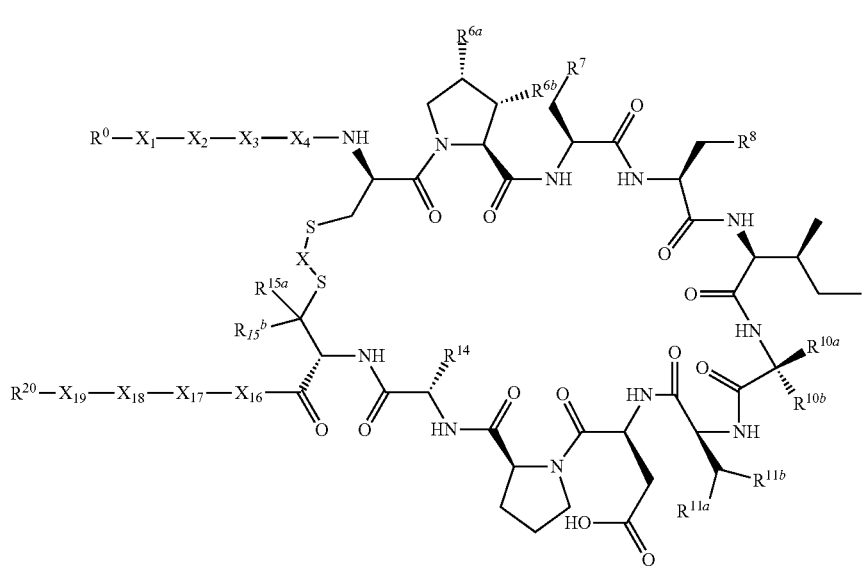

and their pharmaceutically acceptable salts, can modulate the K-Ras(G12D) activity and thereby effect the signaling pathways which regulate cell growth, differentiation, and proliferation associated with oncological disorders. The invention furthermore relates to processes for preparing compounds of Formula (I), to the use of such compounds for the treatment of oncological disorders and for preparing compounds for this purpose, and to pharmaceutical compositions which comprise compounds of Formula (I).

BRIEF DESCRIPTION OF THE DRAWINGS

FIG. 1A to FIG. 1H show examples of K-Ras modulators of the compound of Formula (I) as well as reference polypeptides, their mass, and observed mass spectral molecular ions.

FIG. 2A to FIG. 2D show certain biological properties of the exemplified K-Ras modulators of the compound of Formula (I) as well as reference polypeptides.

DETAILED DESCRIPTION OF THE INVENTION

The Applicants have introduced certain structural features into derivatives of KRpep-2d which significantly improve the properties of inhibitors of the protein. Applicants observed that KRpep-2d is a bona fide binder of K-Ras (G12D) with high affinity for the GDP-loaded form but observed weaker affinity for the GTP-loaded form of the protein. In addition, the Applicants observed the rapid proteolytic degradation of the macrocycle in a cell homogenate stability study and the absence of biological activity, i.e., inhibition of ERK phosphorylation in an AsPC-1 cell line as described below in the Examples. While not being bound by any particular theory, the Applicants believe that KRpep-2d's moderate cellular activity is due to its limited disulfide bridge of KRpep-2d. In addition, the stereochemistry of one of the cysteine residues involved in the bridge to form the cyclic peptide is inverted. The structural features incorporated into the compounds of Formula (I) result in improved potency, stability, and cell permeability, and thus achieve inhibition of K-Ras dependent pathways in AsPC-1 cells at micromolar concentrations.

In some embodiments, the stereochemistry of the N- and C-terminal L-Arg residues which are present in KRpep-2d are inverted. Thus, the compounds of Formula (I) include D-arginine residues at the N- and/or C-terminus of the peptide (e.g., (D-Arg)$_4$). In addition, certain embodiments of the compounds of Formula (I) incorporate replacements of one or more amino acid residues of KRpep-2d, for instance, at positions 6, 8, 10, 11 and 14 of KRpep-2d. Specific replacement resulted in either improved affinity for K-Ras (G12D) as observed in competition binding assays or enhanced cellular permeability, cytosolic exposure (Nano-Click assay) or proteolytic stability (cell homogenate stability) as shown in the Examples below.

In embodiment no. 1, the present invention provides a compound having structural Formula (I) as shown above or a pharmaceutically acceptable salt thereof, wherein:

$R^{6a}$ and $R^{6b}$ are independently H, $C_1$-$C_3$ alkyl, fluoro, —$NH_2$, azido, hydroxy, $C_3$-$C_6$ cycloalkyl, phenyl, or —$OR^{6c}$, wherein $R^{6c}$ is allyl, propargyl, or benzyl; or $R^{6a}$ and $R^{6b}$, together with the carbon atoms to which they are attached, form a 3- to 6-membered cycloalkyl ring which is unsubstituted or substituted by 1 to 3 $C_1$-$C_3$ alkyl;

$R^7$ is $C_1$-$C_7$ alkyl or $C_3$-$C_6$ cycloalkyl;

$R^8$ is $C_6$-$C_{10}$ aryl or indolyl, wherein said $C_6$-$C_{10}$ aryl or indolyl of $R^8$ is optionally (i) substituted by one $C_1$-$C_6$ alkyl, $C_1$-$C_6$ fluoroalkyl, hydroxy, $C_1$-$C_6$ alkoxy, $C_1$-$C_6$ fluoroalkoxy, phenyl, or benzyloxy and (ii) optionally substituted by 1 to 5 halogens;

$R^{10a}$ is —$CH_2OH$, $C_1$-$C_8$ alkyl, $C_3$-$C_6$ cycloalkyl, or —$CH_2$—$R^{10c}$, wherein $R^{10c}$ is $C_6$-$C_{10}$ heteroaryl or $C_3$-$C_6$ cycloalkyl;

$R^{10b}$ is H or $C_1$-$C_4$ alkyl;

or $R^{10a}$ and $R^{10b}$ together with the carbon atom to which they are attached form a 3- to 6-membered cycloalkyl ring, wherein said 3- to 6-membered cycloalkyl is optionally fused to phenyl;

$R^{11a}$ and $R^{11b}$ are independently H, $C_3$-$C_6$ cycloalkyl, $C_6$-$C_{10}$ aryl, or 5- to 9-membered heteroaryl, wherein said $C_6$-$C_{10}$ aryl or 5- to 9-membered heteroaryl of $R^{11a}$ or $R^{11b}$ is optionally substituted by (i) 1 hydroxy, $C_1$-$C_6$ alkyl, $C_1$-$C_6$ fluoroalkyl, or $C_1$-$C_6$ fluoroalkoxy and (ii) 1 to 5 halogens;

$R^{14}$ is $C_1$-$C_6$ alkyl, —$CH_2CH_2CO_2H$, —$C_3$-$C_6$ cycloalkyl, or —$CH_2$—$R^{14a}$, wherein $R^{14a}$ is $C_3$-$C_6$cycloalkyl;

$R^{15a}$ and $R^{15b}$ are independently H or $C_1$-$C_3$ alkyl;

X is $C_1$-$C_3$ alkylene or carbonyl;

$R^0$ is:
(i) H,
(ii) Ac-Lys($N_3$),
(iii) $R^{0a}C(O)$— wherein $R^{0a}$ is $C_1$-$C_6$ alkyl or $C_3$-$C_6$ cycloalkyl; or
(iv) a Cell-Penetrating Peptide (CPP) moiety; or
(v) a group of the formula:

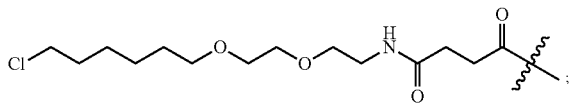 [SMILES: *C(=O)CCC(=O)NCCOCCOCCCCCCCl]

$R^{20}$ is:
(i) —OH;
(ii) —$OR^{20a}$, wherein $R^{20a}$ is $C_1$-$C_6$ alkyl;
(iii) —$NH_2$;
(iv) —$N(H)R^{20a}$;
(v) —$N(R^{20a})(R^{20b})$, wherein $R^{20b}$ is $C_1$-$C_6$ alkyl, or alternatively, $R^{20a}$ and $R^{20b}$ together with the nitrogen atom to which they are attached form a 3- to 6-membered heterocycloalkyl ring or
(vi) a CPP moiety;

or alternatively, $R^0$ and $R^{20}$ join to form a second ring via an amide linkage;

$X_1$, $X_4$, $X_{16}$, and $X_{19}$ are independently L-Arg, D-Arg, L-homoArg, N-Me-L-Arg, L-Glu, L-Lys, L-Gly-Aeea, L-Gly-L-Lys($N_3$)-Aeea, or absent;

$X_2$, $X_3$, $X_{17}$, and $X_{18}$ are independently L-Arg, D-Arg, L-homoArg, N-Me-L-Arg, L-Leu, D-Leu, L-Nle, L-Trp, L-Phe, L-Ala, L-Bip, L-Phe(4-$CO_2H$), L-Glu, L-Lys, (L-Arg)$_3$, (D-Arg)$_3$, (L-homoArg)$_3$, (L-Arg)$_4$, (D-Arg)$_4$, (L-homoArg)$_4$, or absent;

wherein when one of $X_1$, $X_2$, $X_3$, and $X_4$ is L-Glu, and one of $X_{16}$, $X_{17}$, $X_{18}$, and $X_{19}$ is L-Lys, the side chains of said L-Glu and L-Lys may optionally form an amide bond;

wherein when one of $X_1$, $X_2$, $X_3$, and $X_4$ is L-Lys, and one of $X_{16}$, $X_{17}$, $X_{18}$, and $X_{19}$ is L-Glu, the side chains of said L-Lys and L-Glu may optionally form an amide bond;

or a pharmaceutically acceptable salt thereof.

In embodiment no. 2, the present invention provides the compound having structural Formula (I), wherein $R^0$ is acetyl and the remaining variables are as set forth in embodiment no. 1.

In embodiment no. 3, the present invention provides the compound having structural Formula (I), wherein $R^{20}$ is —$NH_2$; and the remaining variables are as set forth in embodiment no. 1 or 2.

In embodiment no. 4, the present invention provides the compound having structural Formula (I), wherein $R^{6a}$ and $R^{6b}$ are both H; and the remaining variables are as set forth in any one of embodiment nos. 1-3.

In embodiment no. 5, the present invention provides the compound having structural Formula (I), wherein $R^7$ is —$C(H)(CH_3)_2$; and the remaining variables are as set forth in any one of embodiment nos. 1-4.

In embodiment no. 6, the present invention provides the compound having structural Formula (I), $R^8$ is 4-hydroxyphenyl; and the remaining variables are as set forth in any one of embodiment nos. 1-5.

In embodiment no. 7, the present invention provides the compound having structural Formula (I), wherein $R^{10a}$ is —$CH_2OH$ and $R^{10b}$ is H; and the remaining variables are as set forth in any one of embodiment nos. 1-6.

In embodiment no. 8, the present invention provides the compound having structural Formula (I), wherein $R^{11a}$ is 4-hydroxyphenyl and $R^{11b}$ is H; and the remaining variables are as set forth in any one of embodiment nos. 1-7.

In embodiment no. 9, the present invention provides the compound having structural Formula (I), wherein $R^{14}$ is —$C(H)(CH_3)_2$; and the remaining variables are as set forth in any one of embodiment nos. 1-8.

In embodiment no. 10, the present invention provides the compound having structural Formula (I), wherein $R^{15a}$ and $R^{15b}$ are both H; and the remaining variables are as set forth in any one of embodiment nos. 1-9.

In embodiment no. 11, the present invention provides the compound having structural Formula (I), wherein wherein X is methylene; and the remaining variables are as set forth in any one of embodiment nos. 1-10.

In embodiment no. 12, the present invention provides the compound having structural Formula (I), wherein the moiety —$X_1$—$X_2$—$X_3$—$X_4$— is:
(D-Arg)$_2$, (D-Arg)$_3$, (D-Arg)$_4$, (D-Arg)$_8$,
(L-Arg)$_2$, (L-Arg)$_3$, (L-Arg)$_4$, (L-Arg)$_8$,
(L-homoArg)$_2$, or (L-homoArg)$_4$;

and the remaining variables are as set forth in any one of embodiment nos. 1-11.

In embodiment no. 13, the present invention provides the compound as set forth in embodiment no. 12, wherein the moiety —$X_1$—$X_2$—$X_3$—$X_4$— is (D-Arg)$_4$.

In embodiment no. 14, the present invention provides the compound having structural Formula (I), wherein the moiety —$X_{16}$—$X_{17}$—$X_{18}$—$X_{19}$— is:
(D-Arg)$_2$, (D-Arg)$_3$, (D-Arg)$_4$, (D-Arg)$_8$,
(L-Arg)$_2$, (L-Arg)$_3$, (L-Arg)$_4$, (L-Arg)$_8$,
(L-homoArg)$_2$, or (L-homoArg)$_4$;

and the remaining variables are as set forth in any one of embodiment nos. 1-13.

In embodiment no. 15, the present invention provides the compound as set forth in embodiment no. 14, wherein the moiety —$X_{16}$—$X_{17}$—$X_{18}$—$X_{19}$— is (D-Arg)$_4$.

In embodiment no. 16, the present invention provides a compound selected from SEQ ID Nos. 1-66 as set forth below, or a pharmaceutically acceptable salt thereof. In this embodiment nos. 16 and 17, "*", "#", "‡" indicate the residues involved in cyclic bond formation. Residues (e.g., Cys, DCys, Pen) marked with "*" indicated that the two sulfur atoms of the side chains are cyclized by a thioacetal bridge (S—$CH_2$—S or methylene cross-linker). Residues (e.g., Lys, Dab, Dap, Asp, Glu) indicated with "‡" are cyclized by side chain-to-side chain lactam bridge formation. Amino acids marked by "#" are cyclized by head-to-tail lactamization.

Ac-Lys(N₃)-DArg-DArg-DArg-DArg-DCys*-Pro-Leu-2Nal-Ile-Ser-Tyr-Asp-Pro-Val-Cys*-DArg-DArg-DArg-DArg-NH₂; (SEQ ID NO: 1)

Ac-Lys(N₃)-DArg-DArg-DArg-DArg-DCys*-Pro-Leu-Tyr-Ile-AMS-Tyr-Asp-Pro-Val-Cys*-DArg-DArg-DArg-DArg-NH₂; (SEQ ID NO: 2)

CPP12-Gly-Lys(N₃)-Aeea-Arg-Arg-DCys*-Pro-Leu-Tyr-Ile-Ser-Tyr-Asp-Pro-Val-Cys*-Arg-Arg-NH₂; (SEQ ID NO: 3)

Ac-Lys(N₃)-DArg-DArg-DArg-DArg-DCys*-T3PhP-Leu-Tyr-Ile-Ser-Tyr-Asp-Pro-Val-Cys*-DArg-DArg-DArg-DArg-NH₂; (SEQ ID NO: 4)

Ac-Lys(N₃)-DArg-DArg-DArg-DArg-DCys*-Pro-Leu-2Nal-Ile-Ser-Tyr-Asp-Pro-Cha-Cys*-DArg-DArg-DArg-DArg-NH₂; (SEQ ID NO: 5)

Ac-Lys(N₃)-DArg-DArg-DArg-DArg-DCys*-Pro-Leu-2Nal-Ile-Ser-Trp-Asp-Pro-Chg-Cys*-DArg-DArg-DArg-DArg-NH₂; (SEQ ID NO: 6)

Ac-Lys(N₃)-NMeArg-Arg-NMeArg-Arg-DCys*-Pro-Leu-Tyr-Ile-Ser-Tyr-Asp-Pro-Val-Cys*-Arg-NMeArg-Arg-NMeArg-NH₂; (SEQ ID NO: 7)

cyclo(DArg#-DArg-DArg-DArg-DCys*-Pro-Leu-Tyr-Ile-Ser-Tyr-Asp-Pro-Val-Cys*-DArg-DArg-DArg-DArg#); (SEQ ID NO: 8)

Ac-Lys(N₃)-DArg-DArg-DArg-DArg-DCys*-Pro-Leu-Tyr-Ile-Ser-Tyr-Asp-AMP-Val-Cys*-DArg-DArg-DArg-DArg-NH₂; (SEQ ID NO: 9)

Ac-DArg-DArg-DArg-DArg-DCys*-Pro-Leu-Tyr-Ile-Ser-Tyr-Asp-Pro-Val-Cys*-DArg-DArg-DArg-DArg-NH₂; (SEQ ID NO: 10)

Ac-Lys(N₃)-DArg-DArg-DArg-DArg-DCys*-Pro-Leu-Tyr-Ile-Cle-Tyr-Asp-Pro-Val-Cys*-DArg-DArg-DArg-DArg-NH₂; (SEQ ID NO: 11)

Ac-Lys(N₃)-DArg-DArg-DArg-DArg-DCys*-Pro-Leu-Tyr-Ile-Ser-Tyr-Asp-Pro-Cha-Cys*-DArg-DArg-DArg-DArg-NH₂; (SEQ ID NO: 12)

Ac-Lys(N₃)-NMeArg-DArg-NMeArg-DArg-DCys*-Pro-Leu-Tyr-Ile-Ser-Tyr-Asp-Pro-Val-Cys*-DArg-NMeArg-DArg-NMeArg-NH₂; (SEQ ID NO: 13)

Ac-Lys(N₃)-DArg-DArg-DArg-DArg-DCys*-Pro-Leu-2Nal-Ile-Cle-Tyr-Asp-Pro-Cha-Cys*-DArg-DArg-DArg-DArg-NH₂; (SEQ ID NO: 14)

Ac-Lys(N₃)-DArg-DArg-DArg-DArg-DCys*-Pro-Leu-Tyr-Ile-Ser-Tyr-Asp-Pro-Val-Cys*-DArg-DArg-DArg-DArg-NH₂; (SEQ ID NO: 15)

Ac-Penetratin-Gly-Lys(N₃)-Aeea-DCys*-Pro-Leu-Tyr-Ile-Ser-Tyr-Asp-Pro-Val-Cys*-Arg-NH₂; (SEQ ID NO: 16)

-continued (SEQ ID NO: 17)
Ac-Lys(N$_3$)-Arg-Arg-DCys*-Pro-Leu-F4tBu-Ile-Ser-F4tBu-Asp-Pro-Val-Cys*-Arg-Arg-NH$_2$;

(SEQ ID NO: 18)
Ac-Lys(N$_3$)-Arg-Arg-Arg-Arg-DCys*-Pro-Leu-2Nal-Ile-Ser-Tyr-Asp-Pro-Val-Cys*-Arg-Arg-Arg-Arg-NH$_2$;

(SEQ ID NO: 19)
Ac-Lys(N$_3$)-DArg-DArg-DArg-DArg-DCys*-Pro-Leu-Tyr-Ile-Ser-Tyr-Asp-Pro-Glu-Cys*-DArg-DArg-DArg-DArg-NH$_2$;

(SEQ ID NO: 20)
Ac-DCys*-Pro-Leu-Tyr-Ile-Ser-Tyr-Asp-Pro-Val-Cys*-Arg-Gly-Lys(N3)-Aeea-Penetratin-NH$_2$;

(SEQ ID NO: 21)
Ac-Arg-Arg-DCys*-Pro-Leu-Tyr-Ile-Cha-Cha-Asp-Pro-Val-Cys*-Arg-Arg-NH$_2$;

(SEQ ID NO: 22)
Ac-Lys(N$_3$)-Arg-Arg-Arg-Arg-DCys*-Pro-Leu-Tyr-Ile-Ser-Tyr-Asp-Pro-Cha-Cys*-Arg-Arg-Arg-Arg-NH$_2$;

(SEQ ID NO: 23)
Ac-Lys(N$_3$)-Arg-Arg-DCys*-Pro-Leu-Tyr-Ile-Dbg-Tyr-Asp-Pro-Val-Cys*-Arg-Arg-NH$_2$;

(SEQ ID NO: 24)
Ac-Lys(N$_3$)-Arg-Arg-Arg-Arg-DCys*-Pro-Leu-Tyr-Ile-Cle-Tyr-Asp-Pro-Val-Cys*-Arg-Arg-Arg-Arg-NH$_2$;

(SEQ ID NO: 25)
Ac-Lys(N$_3$)-hArg-hArg-DCys*-Pro-Leu-Bip-Ile-Ser-Tyr-Asp-Pro-Val-Cys*-hArg-hArg-NH$_2$;

(SEQ ID NO: 26)
Ac-Lys(N$_3$)-DArg-DLeu-DLeu-DArg-DCys*-T3PhP-Leu-Tyr-Ile-Ser-Tyr-Asp-Pro-Val-Cys*-DArg-DLeu-DLeu-DArg-NH$_2$;

(SEQ ID NO: 27)
Ac-Lys(N$_3$)-DArg-DArg-DCys*-T3PhP-Leu-Bip-Ile-Ser-Tyr-Asp-Pro-Val-Cys*-DArg-DArg-NH$_2$;

(SEQ ID NO: 28)
Ac-Lys(N$_3$)-Arg-Arg-DCys*-T34Me2cPP-Leu-Tyr-Ile-Ser-Tyr-Asp-Pro-Val-Cys*-Arg-Arg-NH$_2$;

(SEQ ID NO: 29)
Ac-Lys(N$_3$)-Arg-Arg-DCys*-Pro-Leu-Tyr-Ile-Aic-Tyr-Asp-Pro-Val-Cys*-Arg-Arg-NH$_2$;

(SEQ ID NO: 30)
Ac-Lys(N$_3$)-hArg-hArg-DCys*-T3PhP-Leu-Tyr-Ile-Ser-Tyr-Asp-Pro-Val-Cys*-hArg-hArg-NH$_2$;

(SEQ ID NO: 31)
Ac-Lys(N$_3$)-DArg-DLeu-DLeu-DArg-DCys*-Pro-Leu-Bip-Ile-Ser-Tyr-Asp-Pro-Val-Cys*-DArg-DLeu-DLeu-DArg-NH$_2$;

(SEQ ID NO: 32)
Ac-Lys(N$_3$)-DArg-DLeu-DLeu-DArg-DCys*-Pro-Leu-2Nal-Ile-Ser-Tyr-Asp-Pro-Val-Cys*-DArg-DLeu-DLeu-DArg-NH$_2$;

-continued

```
                                                         (SEQ ID NO: 33)
Ac-Lys(N3)-Arg-Arg-DCys*-Pro-Leu-YCF3-Ile-Ser-YCF3-Asp-Pro-Val-Cys*-Arg-
Arg-NH2;

(SEQ ID NO: 34)
Ac-Arg-Arg-Arg-Arg-DCys*-Pro-Leu-Tyr-Ile-Ser-Tyr-Asp-Pro-Val-Cys*-Arg-Arg-
Arg-Arg-NH2;

(SEQ ID NO: 35)
Ac-Lys(N3)-Arg-Arg-DCys*-T3PhP-Leu-Tyr-Ile-Ser-Tyr-Asp-Pro-Val-Cys*-Arg-Arg-
NH2;

(SEQ ID NO: 36)
Ac-Lys(N3)-Arg-Arg-DCys*-Pro-BHL-Tyr-Ile-Ser-Tyr-Asp-Pro-Val-Cys*-Arg-Arg-
NH2;

(SEQ ID NO: 37)
Ac-Lys(N3)-DArg-DLeu-DLeu-DArg-DCys*-Pro-Leu-F4CF3-Ile-Ser-Tyr-Asp-Pro-
Val-Cys*-DArg-DLeu-DLeu-DArg-NH2;

(SEQ ID NO: 38)
Ac-Lys(N3)-Arg-Arg-DCys*-Pro-Leu-Tyr-Ile-Cle-Tyr-Asp-Pro-Val-Cys*-Arg-Arg-
NH2;

(SEQ ID NO: 39)
Ac-Arg-Arg-DCys*-Pro-Leu-Tyr-Ile-Trp-1Nal-Asp-Pro-Val-Cys*-Arg-Arg-NH2;

(SEQ ID NO: 40)
Ac-Arg-Arg-DCys*-T3PhP-Leu-Tyr-Ile-Ser-Tyr-Asp-Pro-Val-Cys*-Arg-Arg-NH2;

(SEQ ID NO: 41)
Ac-Lys(N3)-Arg-Arg-DCys*-Pro-Leu-Tyr-Ile-Ser-Bhg-Asp-Pro-Val-Cys*-Arg-Arg-
NH2;

(SEQ ID NO: 42)
Ac-Lys(N3)-Arg-Arg-DCys*-Pro-Leu-Tyr-Ile-C8G-Tyr-Asp-Pro-Val-Cys*-Arg-Arg-
NH2;

(SEQ ID NO: 43)
Ac-Lys(N3)-Arg-Arg-DCys*-Pro-Leu-YBzl-Ile-Ser-Tyr-Asp-Pro-Val-Cys*-Arg-Arg-
NH2;

(SEQ ID NO: 44)
Ac-Lys(N3)-Arg-Arg-Arg-Arg-DCys*-T3OHP-Leu-Tyr-Ile-Ser-Tyr-Asp-Pro-Val-
Cys*-Arg-Arg-Arg-Arg-NH2;

(SEQ ID NO: 45)
Ac-Lys(N3)-Arg-Arg-DCys*-Pro-Leu-Tyr-Ile-Ser-4Ial-Asp-Pro-Val-Cys*-Arg-Arg-
NH2;

(SEQ ID NO: 46)
Ac-Lys(N3)-Arg-Nle-Nle-Arg-DCys*-Pro-Leu-Tyr-Ile-Ser-Tyr-Asp-Pro-Val-Cys*-
Arg-Nle-Nle-Arg-NH2;

(SEQ ID NO: 47)
Ac-Lys(N3)-Arg-Arg-DCys*-Pro-Leu-Tyr-Ile-Lys-Tyr-Asp-Pro-Val-Cys*-Arg-Arg-
NH2;

(SEQ ID NO: 48)
Ac-Arg-Arg-DCys*-Pro-Leu-Tyr-Ile-Trp-Cha-Asp-Pro-Val-Cys*-Arg-Arg-NH2;

(SEQ ID NO: 49)
Ac-Lys(N3)-Arg-Leu-Leu-Arg-DCys*-Pro-Leu-2Nal-Ile-Ser-Trp-Asp-Pro-Chg-Cys*-
Arg-Leu-Leu-Arg-NH2;
```

(SEQ ID NO: 50)
Ac-Arg-Arg-DCys*-Pro-Leu-Tyr-Ile-Ser-Dip-Asp-Pro-Val-Cys*-Arg-Arg-NH$_2$;

(SEQ ID NO: 51)
Ac-Lys(N$_3$)-DArg-DArg-DCys*-Pro-Leu-Bip-Ile-Ser-Tyr-Asp-Pro-Val-Cys*-DArg-DArg-NH$_2$;

(SEQ ID NO: 52)
Ac-Lys(N3)-Arg-Arg-DCys*-Pro-Leu-Bip-Ile-Ser-Tyr-Asp-Pro-Val-Cys*-Arg-Arg-NH$_2$;

(SEQ ID NO: 53)
Ac-Lys(N$_3$)-Arg-Arg-Arg-Arg-DCys*-Pro-Leu-Tyr-Ile-Ser-Tyr-Asp-Pro-Val-Cys*-Arg-Arg-Arg-Arg-NH$_2$;

(SEQ ID NO: 54)
Ac-Lys(N$_3$)-Arg-Arg-DCys*-Pro-Leu-Tic-Ile-Ser-Tyr-Asp-Pro-Val-Cys*-Arg-Arg-NH$_2$;

(SEQ ID NO: 55)
Ac-Lys(N$_3$)-Arg-Arg-DCys*-Pro-Leu-Tyr-Ile-Arg-Tyr-Asp-Pro-Val-Cys*-Arg-Arg-NH$_2$;

(SEQ ID NO: 56)
Ac-Lys(N$_3$)-Arg-Arg-DCys*-Pro-C8G-Tyr-Ile-Ser-Tyr-Asp-Pro-Val-Cys*-Arg-Arg-NH$_2$;

(SEQ ID NO: 57)
Ac-DArg-Glu‡-DArg-DArg-DCys*-Pro-Leu-Tyr-Ile-Ser-Tyr-Asp-Pro-Val-Cys*-DArg-Lys‡-DArg-DArg-NH$_2$;

(SEQ ID NO: 58)
Ac-Lys(N$_3$)-hArg-hArg-DCys*-Pro-Leu-2Nal-Ile-Ser-Tyr-Asp-Pro-Val-Cys*-hArg-hArg-NH$_2$;

(SEQ ID NO: 59)
Ac-Lys(N$_3$)-DArg-DArg-DArg-DCys*-Pro-Leu-Tyr-Ile-Ser-Tyr-Asp-Pro-Val-Cys*-DArg-DArg-DArg-NH$_2$;

(SEQ ID NO: 60)
Ac-Arg-Arg-DCys*-Pro-Leu-Tyr-Ile-Nva-1Nal-Asp-Pro-Val-Cys*-Arg-Arg-NH2;

(SEQ ID NO: 61)
Ac-Lys(N$_3$)-Arg-Arg-DCys*-Pro-Leu-Tyr-Ile-Ser-Tyr-Asp-Pro-Bhg-Cys*-Arg-Arg-NH$_2$;

(SEQ ID NO: 62)
Ac-TP2-Gly-Lys(N$_3$)-Aeea-DCys*-Pro-Leu-Tyr-Ile-Ser-Tyr-Asp-Pro-Val-Cys*-Arg-NH$_2$;

(SEQ ID NO: 63)
Ac-Lys(N$_3$)-Arg-Arg-DCys*-Pro-Npg-Tyr-Ile-Ser-Tyr-Asp-Pro-Val-Cys*-Arg-Arg-NH$_2$;

(SEQ ID NO: 64)
Ac-Lys(N$_3$)-Arg-Arg-DCys*-Pro-Leu-Tyr-Ile-Ser-DBhg-Asp-Pro-Val-Cys*-Arg-Arg-NH$_2$;

(SEQ ID NO: 65)
Ac-Lys(N$_3$)-Arg-Arg-DCys*-Pro-Leu-Tyr-Ile-Ser-Tyr-Asp-Pro-Val-Pen*-Arg-Arg-NH$_2$;
or

```
                                                          (SEQ ID NO: 66)
Ac-Lys(N3)-Arg-Arg-DCys*-Pro-Leu-Lys-Ile-Ser-Tyr-Asp-Pro-Val-Cys*-Arg-Arg-

NH2;
```
or a pharmaceutically acceptable salt thereof.

In embodiment no. 18, the present invention provides a compound selected from SEQ ID Nos. 8, 10, 21, 34, 39, 40, 48, 50, 57, 60, and 70-125 as set forth below, or a pharmaceutically acceptable salt thereof.

```
                                                          (SEQ ID NO: 70)
Ac-DArg-DArg-DArg-DArg-DCys*-Pro-Leu-2Nal-Ile-Ser-Tyr-Asp-Pro-Val-Cys*-

DArg-DArg-DArg-DArg-NH2;

(SEQ ID NO: 71)
Ac-DArg-DArg-DArg-DArg-DCys*-Pro-Leu-Tyr-Ile-AMS-Tyr-Asp-Pro-Val-Cys*-

DArg-DArg-DArg-DArg-NH2;

(SEQ ID NO: 72)
CPP12-Gly-Aeea-Arg-Arg-DCys*-Pro-Leu-Tyr-Ile-Ser-Tyr-Asp-Pro-Val-Cys*-Arg- Arg-NH2;

(SEQ ID NO: 73)
Ac-DArg-DArg-DArg-DArg-DCys*-T3PhP-Leu-Tyr-Ile-Ser-Tyr-Asp-Pro-Val-Cys*-

DArg-DArg-DArg-DArg-NH2;

(SEQ ID NO: 74)
Ac-DArg-DArg-DArg-DArg-DCys*-Pro-Leu-2Nal-Ile-Ser-Tyr-Asp-Pro-Cha-Cys*-

DArg-DArg-DArg-DArg-NH2;

(SEQ ID NO: 75)
Ac-DArg-DArg-DArg-DArg-DCys*-Pro-Leu-2Nal-Ile-Ser-Trp-Asp-Pro-Chg-Cys*-

DArg-DArg-DArg-DArg-NH2;

(SEQ ID NO: 76)
Ac-NMeArg-Arg-NMeArg-Arg-DCys*-Pro-Leu-Tyr-Ile-Ser-Tyr-Asp-Pro-Val-Cys*-

Arg-NMeArg-Arg-NMeArg-NH2;

(SEQ ID NO: 8)
cyclo(DArg#-DArg-DArg-DArg-DCys*-Pro-Leu-Tyr-Ile-Ser-Tyr-Asp-Pro-Val-Cys*-

DArg-DArg-DArg-DArg#);

(SEQ ID NO: 77)
Ac-DArg-DArg-DArg-DArg-DCys*-Pro-Leu-Tyr-Ile-Ser-Tyr-Asp-AMP-Val-Cys*-

DArg-DArg-DArg-DArg-NH2;

(SEQ ID NO: 10)
Ac-DArg-DArg-DArg-DArg-DCys*-Pro-Leu-Tyr-Ile-Ser-Tyr-Asp-Pro-Val-Cys*-

DArg-DArg-DArg-DArg-NH2;

(SEQ ID NO: 78)
Ac-DArg-DArg-DArg-DArg-DCys*-Pro-Leu-Tyr-Ile-Cle-Tyr-Asp-Pro-Val-Cys*-

DArg-DArg-DArg-DArg-NH2;

(SEQ ID NO: 79)
Ac-DArg-DArg-DArg-DArg-DCys*-Pro-Leu-Tyr-Ile-Ser-Tyr-Asp-Pro-Cha-Cys*-

DArg-DArg-DArg-DArg-NH2;

(SEQ ID NO: 80)
Ac-NMeArg-DArg-NMeArg-DArg-DCys*-Pro-Leu-Tyr-Ile-Ser-Tyr-Asp-Pro-Val-

Cys*-DArg-NMeArg-DArg-NMeArg-NH2;
```

-continued

```
                                                        (SEQ ID NO: 81)
Ac-DArg-DArg-DArg-DArg-DCys*-Pro-Leu-2Nal-Ile-Cle-Tyr-Asp-Pro-Cha-Cys*-

DArg-DArg-DArg-DArg-NH2;

(SEQ ID NO: 82)
Ac-DArg-DArg-DArg-DArg-DCys*-Pro-Leu-Tyr-Ile-Ser-Tyr-Asp-Pro-Val-Cys*-

DArg-DArg-DArg-DArg-NH2;

(SEQ ID NO: 83)
Ac-Penetratin-Gly-Aeea-DCys*-Pro-Leu-Tyr-Ile-Ser-Tyr-Asp-Pro-Val-Cys*-Arg-NH2;

(SEQ ID NO: 84)
Ac-Arg-Arg-DCys*-Pro-Leu-F4tBu-Ile-Ser-F4tBu-Asp-Pro-Val-Cys*-Arg-Arg-NH2;

(SEQ ID NO: 85)
Ac-Arg-Arg-Arg-Arg-DCys*-Pro-Leu-2Nal-Ile-Ser-Tyr-Asp-Pro-Val-Cys*-Arg-Arg-

Arg-Arg-NH2;

(SEQ ID NO: 86)
Ac-DArg-DArg-DArg-DArg-DCys*-Pro-Leu-Tyr-Ile-Ser-Tyr-Asp-Pro-Glu-Cys*-

DArg-DArg-DArg-DArg-NH2;

(SEQ ID NO: 87)
Ac-DCys*-Pro-Leu-Tyr-Ile-Ser-Tyr-Asp-Pro-Val-Cys*-Arg-Gly-Aeea-Penetratin-NH2;

(SEQ ID NO: 21)
Ac-Arg-Arg-DCys*-Pro-Leu-Tyr-Ile-Cha-Cha-Asp-Pro-Val-Cys*-Arg-Arg-NH2;

(SEQ ID NO: 88)
Ac-Arg-Arg-Arg-Arg-DCys*-Pro-Leu-Tyr-Ile-Ser-Tyr-Asp-Pro-Cha-Cys*-Arg-Arg-

Arg-Arg-NH2;

(SEQ ID NO: 89)
Ac-Arg-Arg-DCys*-Pro-Leu-Tyr-Ile-Dbg-Tyr-Asp-Pro-Val-Cys*-Arg-Arg-NH2;

(SEQ ID NO: 90)
Ac-Arg-Arg-Arg-Arg-DCys*-Pro-Leu-Tyr-Ile-Cle-Tyr-Asp-Pro-Val-Cys*-Arg-Arg-

Arg-Arg-NH2;

(SEQ ID NO: 91)
Ac-hArg-hArg-DCys*-Pro-Leu-Bip-Ile-Ser-Tyr-Asp-Pro-Val-Cys*-hArg-hArg-NH2;

(SEQ ID NO: 92)
Ac-DArg-DLeu-DLeu-DArg-DCys*-T3PhP-Leu-Tyr-Ile-Ser-Tyr-Asp-Pro-Val-Cys*-

DArg-DLeu-DLeu-DArg-NH2;

(SEQ ID NO: 93)
Ac-DArg-DArg-DCys*-T3PhP-Leu-Bip-Ile-Ser-Tyr-Asp-Pro-Val-Cys*-DArg-DArg-

NH2;

(SEQ ID NO: 94)
Ac-Arg-Arg-DCys*-T34Me2cPP-Leu-Tyr-Ile-Ser-Tyr-Asp-Pro-Val-Cys*-Arg-Arg-

NH2;

(SEQ ID NO: 95)
Ac-Arg-Arg-DCys*-Pro-Leu-Tyr-Ile-Aic-Tyr-Asp-Pro-Val-Cys*-Arg-Arg-NH2;

(SEQ ID NO: 96)
Ac-hArg-hArg-DCys*-T3PhP-Leu-Tyr-Ile-Ser-Tyr-Asp-Pro-Val-Cys*-hArg-hArg-NH2;

(SEQ ID NO: 97)
Ac-DArg-DLeu-DLeu-DArg-DCys*-Pro-Leu-Bip-Ile-Ser-Tyr-Asp-Pro-Val-Cys*-

DArg-DLeu-DLeu-DArg-NH2;

(SEQ ID NO: 98)
Ac-DArg-DLeu-DLeu-DArg-DCys*-Pro-Leu-2Nal-Ile-Ser-Tyr-Asp-Pro-Val-Cys*-

DArg-DLeu-DLeu-DArg-NH2;
```

```
                                                       (SEQ ID NO: 99)
Ac-Arg-Arg-DCys*-Pro-Leu-YCF3-Ile-Ser-YCF3-Asp-Pro-Val-Cys*-Arg-Arg-NH2;

(SEQ ID NO: 34)
Ac-Arg-Arg-Arg-Arg-DCys*-Pro-Leu-Tyr-Ile-Ser-Tyr-Asp-Pro-Val-Cys*-Arg-Arg-
Arg-Arg-NH2;

(SEQ ID NO: 100)
Ac-Arg-Arg-DCys*-T3PhP-Leu-Tyr-Ile-Ser-Tyr-Asp-Pro-Val-Cys*-Arg-Arg-NH2;

(SEQ ID NO: 101)
Ac-Arg-Arg-DCys*-Pro-BHL-Tyr-Ile-Ser-Tyr-Asp-Pro-Val-Cys*-Arg-Arg-NH2;

(SEQ ID NO: 102)
Ac-DArg-DLeu-DLeu-DArg-DCys*-Pro-Leu-F4CF3-Ile-Ser-Tyr-Asp-Pro-Val-Cys*-
DArg-DLeu-DLeu-DArg-NH2;

(SEQ ID NO: 103)
Ac-Arg-Arg-DCys*-Pro-Leu-Tyr-Ile-Cle-Tyr-Asp-Pro-Val-Cys*-Arg-Arg-NH2;

(SEQ ID NO: 39)
Ac-Arg-Arg-DCys*-Pro-Leu-Tyr-Ile-Trp-1Nal-Asp-Pro-Val-Cys*-Arg-Arg-NH2;

(SEQ ID NO: 40)
Ac-Arg-Arg-DCys*-T3PhP-Leu-Tyr-Ile-Ser-Tyr-Asp-Pro-Val-Cys*-Arg-Arg-NH2;

(SEQ ID NO: 104)
Ac-Arg-Arg-DCys*-Pro-Leu-Tyr-Ile-Ser-Bhg-Asp-Pro-Val-Cys*-Arg-Arg-NH2;

(SEQ ID NO: 105)
Ac-Arg-Arg-DCys*-Pro-Leu-Tyr-Ile-C8G-Tyr-Asp-Pro-Val-Cys*-Arg-Arg-NH2;

(SEQ ID NO: 106)
Ac-Arg-Arg-DCys*-Pro-Leu-YBzl-Ile-Ser-Tyr-Asp-Pro-Val-Cys*-Arg-Arg-NH2;

(SEQ ID NO: 107)
Ac-Arg-Arg-Arg-Arg-DCys*-T3OHP-Leu-Tyr-Ile-Ser-Tyr-Asp-Pro-Val-Cys*-Arg-
Arg-Arg-Arg-NH2;

(SEQ ID NO: 108)
Ac-Arg-Arg-DCys*-Pro-Leu-Tyr-Ile-Ser-4Ial-Asp-Pro-Val-Cys*-Arg-Arg-NH2;

(SEQ ID NO: 109)
Ac-Arg-Nle-Nle-Arg-DCys*-Pro-Leu-Tyr-Ile-Ser-Tyr-Asp-Pro-Val-Cys*-Arg-Nle-Nle-
Arg-NH2;

(SEQ ID NO: 110)
Ac-Arg-Arg-DCys*-Pro-Leu-Tyr-Ile-Lys-Tyr-Asp-Pro-Val-Cys*-Arg-Arg-NH2;

(SEQ ID NO: 48)
Ac-Arg-Arg-DCys*-Pro-Leu-Tyr-Ile-Trp-Cha-Asp-Pro-Val-Cys*-Arg-Arg-NH2;

(SEQ ID NO: 111)
Ac-Arg-Leu-Leu-Arg-DCys*-Pro-Leu-2Nal-Ile-Ser-Trp-Asp-Pro-Chg-Cys*-Arg-Leu-
Leu-Arg-NH2;

(SEQ ID NO: 50)
Ac-Arg-Arg-DCys*-Pro-Leu-Tyr-Ile-Ser-Dip-Asp-Pro-Val-Cys*-Arg-Arg-NH2;

(SEQ ID NO: 112)
Ac-DArg-DArg-DCys*-Pro-Leu-Bip-Ile-Ser-Tyr-Asp-Pro-Val-Cys*-DArg-DArg-NH2;

(SEQ ID NO: 113)
Ac-Arg-Arg-DCys*-Pro-Leu-Bip-Ile-Ser-Tyr-Asp-Pro-Val-Cys*-Arg-Arg-NH2;

(SEQ ID NO: 114)
Ac-Arg-Arg-Arg-Arg-DCys*-Pro-Leu-Tyr-Ile-Ser-Tyr-Asp-Pro-Val-Cys*-Arg-Arg-
Arg-Arg-NH2;

(SEQ ID NO: 115)
Ac-Arg-Arg-DCys*-Pro-Leu-Tic-Ile-Ser-Tyr-Asp-Pro-Val-Cys*-Arg-Arg-NH2;

(SEQ ID NO: 116)
Ac-Arg-Arg-DCys*-Pro-Leu-Tyr-Ile-Arg-Tyr-Asp-Pro-Val-Cys*-Arg-Arg-NH2;
```

```
                                                                (SEQ ID NO: 117)
Ac-Arg-Arg-DCys*-Pro-C8G-Tyr-Ile-Ser-Tyr-Asp-Pro-Val-Cys*-Arg-Arg-NH2;

(SEQ ID NO: 57)
Ac-DArg-Glu‡-DArg-DArg-DCys*-Pro-Leu-Tyr-Ile-Ser-Tyr-Asp-Pro-Val-Cys*-DArg-

Lys‡-DArg-DArg-NH2;

(SEQ ID NO: 118)
Ac-hArg-hArg-DCys*-Pro-Leu-2Nal-Ile-Ser-Tyr-Asp-Pro-Val-Cys*-hArg-hArg-NH2;

(SEQ ID NO: 119)
Ac-DArg-DArg-DArg-DCys*-Pro-Leu-Tyr-Ile-Ser-Tyr-Asp-Pro-Val-Cys*-DArg-

DArg-DArg-NH2;

(SEQ ID NO: 60)
Ac-Arg-Arg-DCys*-Pro-Leu-Tyr-Ile-Nva-1Nal-Asp-Pro-Val-Cys*-Arg-Arg-NH2;

(SEQ ID NO: 120)
Ac-Arg-Arg-DCys*-Pro-Leu-Tyr-Ile-Ser-Tyr-Asp-Pro-Bhg-Cys*-Arg-Arg-NH2;

(SEQ ID NO: 121)
Ac-TP2-Gly-Aeea-DCys*-Pro-Leu-Tyr-Ile-Ser-Tyr-Asp-Pro-Val-Cys*-Arg-NH2;

(SEQ ID NO: 122)
Ac-Arg-Arg-DCys*-Pro-Npg-Tyr-Ile-Ser-Tyr-Asp-Pro-Val-Cys*-Arg-Arg-NH2;

(SEQ ID NO: 123)
Ac-Arg-Arg-DCys*-Pro-Leu-Tyr-Ile-Ser-DBhg-Asp-Pro-Val-Cys*-Arg-Arg-NH2;

(SEQ ID NO: 124)
Ac-Arg-Arg-DCys*-Pro-Leu-Tyr-Ile-Ser-Tyr-Asp-Pro-Val-Pen*-Arg-Arg-NH2;
or (SEQ ID NO: 125)
Ac-Arg-Arg-DCys*-Pro-Leu-Lys-Ile-Ser-Tyr-Asp-Pro-Val-Cys*-Arg-Arg-NH2;
``` or a pharmaceutically acceptable salt thereof.

Definitions

"Alkyl", as well as other groups having the prefix "alk", such as alkoxy, and the like, means carbon chains which may be linear or branched, or combinations thereof, containing the indicated number of carbon atoms. In particular embodiments linear alkyl groups have 1-6 carbon atoms and branched alkyl groups have 3-7 carbon atoms. Examples of alkyl groups include methyl, ethyl, propyl, isopropyl, butyl, sec- and tert-butyl, pentyl, hexyl, heptyl, octyl, nonyl and the like.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms (C$_1$-C$_6$ alkylene). In another embodiment, an alkylene group has from 1 to 3 carbon atoms (C$_1$-C$_3$ alkylene). In another embodiment, an alkylene group is branched. In another embodiment, an alkylene group is linear. In one embodiment, an alkylene group is —CH$_2$—. The term "C$_1$-C$_3$ alkylene" refers to an alkylene group having from 1 to 3 carbon atoms. Unless otherwise indicated, an alkylene group is unsubstituted.

"Alkoxy" and "alkyl-O—" are used interchangeably and refer to an alkyl group linked to oxygen.

"Alkyl-NH—" refers to an alkyl group linked to an NH group. Examples of alkyl-NH-include methyl-amino or methyl-NH— and ethyl-amino or ethyl-NH—.

An "amino acid" refers to naturally-occurring α-amino acids and their stereoisomers, as well as unnatural amino acids (such as β-amino acids and substituted amino acids) and their stereoisomers. In the sequences given for the peptides according to the present invention, the amino acid residues have their conventional meaning as given in Chapter 2400 of the Manual of Patent Examining Procedure, 9th Ed. Thus, "Nle" is norleucine, "Asp" is aspartic acid, "His" is histidine, "Phe" is phenylalanine, "Arg" is arginine, "Trp" is tryptophan, and "Lys" is lysine, and so on. It is to be understood that "D" isomers are designated by a "D-" or "D" before the three letter code or amino acid name, such that for example D-Phe is D-phenylalanine or DArg is D-arginine. Amino acid residues not encompassed by the foregoing have the definitions provided in the Table in the Examples section below.

"Aryl" means phenyl or naphthyl, e.g., 1- or 2-napthyl. In some embodiments, the aryl is unsubstituted. In other embodiments, the aryl can be substituted by 1 to 5 C$_1$-C$_6$ alkyl, C$_1$-C$_6$ fluoroalkyl, halo, hydroxy, C$_1$-C$_6$ alkoxy, C$_1$-C$_6$ fluoroalkoxy, phenyl, or benzyloxy.

"Combination therapy" as used herein refers to treatment of a human or animal individual comprising administering a first therapeutic agent and a second therapeutic agent consecutively or concurrently to the individual. In general, the first and second therapeutic agents are administered to the individual separately and not as a mixture; however, there may be embodiments where the first and second therapeutic agents are mixed prior to administration.

"Fluoroalkyl" include mono-substituted as well as multiple fluoro-substituted alkyl groups, up to perfluoro substituted alkyl. For example, fluoromethyl, difluoromethyl, trifluoromethyl, 1,1-difluoroethyl, or 1,1,1,2,2-pentafluorobutyl are included.

"Fluoroalkoxy" and "fluoroalkyl-O" are used interchangeably and refer to fluoro-substituted alkyl groups or "fluoroalkyl" linked through the oxygen atom. Fluoroalkoxy include monosubstituted as well as multiple fluoro-substituted alkoxy groups, up to perfluoro-substituted alkoxy. For example, trifluoromethoxy is included.

"Cell-penetrating peptide" or "CPP" refers to a polycationic, hydrophobic, or amphipathic linear or cyclic peptide, which when conjugated to peptides, including the peptides compound of Formula (I), improve cell-penetration of the conjugated peptide. Such cell-penetrating peptides are described in Milletti, F., Cell-penetrating peptides: classes, origin, and current landscape. *Drug Discov Today* 2012 August; 17(15-16):850-60. Examples of cell-penetrating peptides and their characteristics are provided in Table 1 below.

include cyclopropyl, cyclobutyl, cyclopentyl, cyclohexyl, cycloheptyl, adamantyl, and the like.

"Cycloalkoxy" and "cycloalkyl-O" are used interchangeably and refer to a cycloalkyl group, as defined above, linked to oxygen.

"Heterocycloalkyl" refers to nonaromatic monocyclic and bicyclic ring structures in which one or more atoms in the ring, the heteroatom(s), is an element other than carbon. Such nonaromatic cyclic ring structures can be saturated or unsaturated. Heteroatoms are typically O, S or N atoms. In some embodiments a heterocycloalkyl group is a 3- to 6-membered heterocyclyl containing 1 to 2 heteroatoms selected N, O, and S. Examples of heterocycloalkyl groups include: piperidine, piperazinyl, morpholinyl, pyrrolidinyl, tetrahydrofuranyl, azetidinyl, oxiranyl, or aziridinyl, and the like.

TABLE 1

| SEQ ID NO: | Name | Sequence of Cell-Penetrating Peptide (CPP) | Characteristics |
|---|---|---|---|
| 127 | Tat | (Y)GKKKRRQRRR | Cationic |
| 128 | Penetratin | RQIKIWFQNRRMKWKK | Cationic |
| 129 | Polyarginine (R5, R8 or R9) | RRRRR(RRR(R)) | Cationic |
| 130 | Pep-1 | KETWWETWWTEWSQPKKKRKV (Lys-Glu-Thr-Trp-Trp-Glu-Thr-Trp-Trp-Thr-Glu-Trp-Ser-Gln-Pro-Lys-Lys-Lys-Arg-Lys-Val) | Amphipathic |
| 131 | CPP12 | cyclo(Phe-DPhe-2Nal-Arg-D Arg-Arg-DArg-Gln) | Cationic |
| 132 | TP2 | PLIYLRLLR | Cationic |
| — | Endo-Porter | unknown‡ | Amphipathic |
| 133 | Proline-rich peptide (Pro) | VRLPPPVRLPPPVRLPPP | Proline-rich |
| 134 | Tat-HA2 | CRRRQRRKKRGGDIMGEWGNEIFGAIAGFLG | Cationic fusogenic |
| 135 | Hph-1 | YARVRRRGPRR | Cationic |
| 136 | HP4 | RRRRPRRRTTRRRR | Cationic |
| 137 | LAH4 | KKALLALALHHLAHLALHLALALKKA | Histidine-rich cationic amphipathic |
| 138 | LAH4-L1 | KKALLAHALHLLALLALHLAHALKKA | Histidine-rich cationic amphipathic |
| 139 | Vectofusin-1 | KKALLHAALAHLLALAHHLLALLKKA | Histidine-rich cationic amphipathic |
| 140 | Low molecular weight protamine (LMWP) | VSRRRRRRGGRRRR | Cationic |

‡Summerton, JE, Ann. NY Acad. Sci. 2005 Nov: 1058: 62-75.

"Cycloalkyl" means a saturated cyclic hydrocarbon radical. In particular embodiments, the cycloalkyl group has 3-12 carbon atoms, forming 1-3 carbocyclic rings that are fused. In some embodiments, the cycloalkyl is monocyclic and has from 3 to 6 carbon atoms. Examples of cycloalkyl "Heteroaryl" refers to an aromatic monocyclic and bicyclic ring structures in which one or more atoms in the ring, the heteroatom(s), is an element other than carbon. Heteroatoms are typically O, S, or N atoms. In some embodiments, heteroaryl is a 5- to 9-membered heteroaryl containing 1 to 4 heteroatoms selected from O, S, and N atoms. In some embodiments, heteroaryl is a or 6- to 10-membered heteroaryl containing 1 to 4 heteroatoms selected from 0, S, and N atoms. Examples of heteroaromatic groups include: pyridinyl, pyrimidinyl, pyrrolyl, pyridazinyl, isoxazolyl, thiazolyl, oxazolyl, indolyl, benzoxazolyl, benzothiazolyl, or imidazolyl.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable occurs more than one time in any constituent or in Formula (I) or other generic formulas herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocycloalkyl ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

"Polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, are permitted on any available carbon atom in the ring to which the variable is attached. When a moiety is noted as being "optionally substituted" in Formula (I) or any embodiment thereof, it means that Formula (I) or the embodiment thereof encompasses compounds that contain the noted substituent (or substituents) on the moiety and also compounds that do not contain the noted substituent (or substituents) on the moiety.

The wavy line , as used herein, indicates a point of attachment to the rest of the compound.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of Formula (I) and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula (I), can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts containing acetate, formate or chloride salts are typical for use with the compounds of Formula (I). In some embodiments, salts of compounds of Formula (I) can be formed by exchange well-known to those of ordinary skill in the art, such as by anion exchange, e.g., replacement of trifluoroacetate ions with chloride ions.

Furthermore, compounds of the present invention may exist in amorphous form and/or one or more crystalline forms, and as such all amorphous and crystalline forms and mixtures thereof of the compounds of Formula (I), including the Examples, are intended to be included within the scope of the present invention. In addition, some of the compounds of the instant invention may form solvates with water (i.e., a hydrate) or common organic solvents such as, but not limited to, ethyl acetate. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention.

The present invention also relates to processes for the preparation of the compounds of Formula (I) which are described in the following and by which the compounds of the invention are obtainable.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. In a preferred embodiment, the term "therapeutically effective amount" means an amount of a pharmaceutical drug that alleviates at least one clinical symptom in a human patient. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

| Abbreviations | |
|---|---|
| Abbreviation | Definition |
| 1Nal | 3-(1-Naphthyl)-L-alanine |
| 2Nal | 3-(2-Naphthyl)-L-alanine |
| 4Ial | 3-(1H-4-Indolyl)-L-alanine or (S)-2-amino-3-(1H-indol-4-yl)propanoic acid |
| 5FAM | 5-Carboxyfluorescein |
| AA | Amino acid |
| Ac | Acetyl |
| Aeea | 8-Amino-3,6-dioxaoctanoic acid or PEG$_2$-CH$_2$COOH |
| Aic | 2-Aminoindane-2-carboxylic acid |
| Ala | L-Alanine |
| AMP | α-Methyl-L-Proline |
| AMS | α-Methyl-L-Serine |
| Arg | L-Arginine |
| Asp | L-Aspartic acid |
| BAla | β-Alanine |
| Bhg | (S)-2-Amino-2-(10,11-dihydro-5H-dibenzo[a,d][7]annulen-5-yl)acetic acid |
| BHL | L-β-Homoleucine or (S)-3-amino-5-methylhexanoic acid |
| Bip | L-(4,4'-Biphenyl)-alanine or (S)-2-amino-3-(1,1'-bipheny-4-yl)propanoic acid |
| BME | 2-Mercaptoethanol |
| Boc | tert-Butoxy-carbonyl |
| BOP | (Benzotriazol-1-yloxy)tris(dimethylamino)phosphonium hexafluorophosphate or Castros reagent |
| C8G | L-Octylglycine or L-octyl-Gly-OH or (S)-2-aminodecanoic acid or L-decyline or L-2-aminocapric acid |
| Cba | Cyclobutyl-L-alanine |
| Cha | Cyclohexyl-L-alanine |
| Chg | Cyclohexyl-L-glycine |
| Cle | Cycloleucine or 1-aminocyclopentane carboxylic acid |
| CL$_{int}$ | Intrinsic clearance |
| CTC | 2-Chlorotrityl chloride resin |
| Cys | L-Cysteine |
| DArg | D-Arginine |
| Dbg | Di-n-butyl glycine or 5-aminononane-5-carboxylic acid |
| DBhg | (R)-2-Amino-2-(10,11-dihydro-5H-dibenzo[a,d][7]annulen-5-yl)acetic acid |
| DCM | Dichloromethane |
| DCys | D-Cysteine |
| Dde | 1-(4,4-Dimethyl-2,6-dioxocyclohexylidene)ethyl |
| DI | Deionized |
| DiBac-CA | Dibenzoazacyclooctyne-Chloroalkane |
| DIC | N,N'-Diisopropylcarbodiimide |
| DIPEA | N,N-Diisopropylethylamine or Hünig's base |
| Dip | 3,3-Diphenyl-L-alanine or β-phenyl-Phe-OH |
| DLeu | D-Leucine |
| DMF | N,N-Dimethylformamide |
| DMSO | Dimethyl sulfoxide |
| DODT | 3,6-Dioxa-1,8-octanedithiol |
| DPhe | D-Phenylalanine |
| DTT | Dithiothreitol |
| EDTA | Ethylenediaminetetraacetic acid |
| ERK | Extracellular signal-regulated kinase |
| F4CF3 | 4-Trifluoromethyl-L-phenylalanine |
| F4tBu | 4-tert-Butyl-L-phenylalanine |
| FBS | Fetal bovine serum |
| GDP | Guanosine 5'-diphosphate |
| Gln | L-Glutamine |
| Glu | L-Glutamic acid |
| Glu(OAll) | L-Glutamic acid 5-allyl ester |
| Gly | Glycine |
| GMPPNP | Guanosine 5'-[β,γ-imido]triphosphate or GMP-PNP or Gpp(NH)p |
| GTP | Guanosine 5'-triphosphate |
| h | hour |
| HATU | 1-[Bis(dimethylamino)methylene]-1H-1,2,3-triazolo[4,5-b]pyridinium 3-oxide hexafluorophosphate or N-[(Dimethylamino)-1H-1,2,3-triazolo-[4,5-b] ranium-1-ylmethylene]-N-methylmethanaminium hexafluorophosphate N-oxide |
| HBTU | N,N,N',N'-Tetramethyl-O-(1H-benzotriazol-1-yl)uranium hexafluorophosphate or O-(Benzotriazol-1-yl)-N,N,N',N'-tetramethyluronium hexafluorophosphate |
| hCys | L-Homocysteine or (S)-2-amino-4-mercaptobutyric acid |
| HEPES | (4-(2-hydroxyethyl)-1-piperazineethanesulfonic acid) (zwitterionic sulfonic acid buffering agent) |
| HFIP | Hexafluoroisopropanol |
| His | L-Histidine |
| HOBt | 1-Hydroxybenzotriazole |
| HPLC | High-performance liquid chromatography |
| Ile | L-Isoleucine |
| IPTG | Isopropyl β-D-1-thiogalactopyranoside |
| ivDde | 1-(4,4-Dimethyl-2,6-dioxocyclohexylidene)-3-methylbutyl |
| LDH | Lactate dehydrogenase |
| Leu | L-Leucine |
| Lys | L-Lysine |
| Lys(Alloc) | N$^ε$-Allyloxycarbonyl-L-lysine |
| Lys(N$_3$) | L-Azidolysine |
| MBHA | 4-Methylbenzhydrylamine |
| MEM | Minimum essential medium (Eagle) |
| MeOH | Methanol |
| Met | L-Methionine |
| min | Minute |
| MS | Mass spectrometry |
| Mtt | 4-Methyltrityl |
| EAA | Non-essential amino acid (cell culture supplement) |
| NH$_2$ | C-terminal amide |
| Nle | L-Norleucine or (S)-2-amino caproic acid or (S)-2-amino hexanoic acid |
| NMeArg | A-Methyl-L-Arginine |
| NMM | A-Methylmorpholine |
| NMP | A-Methyl-2-pyrrolidone |
| Npg | L-α-Neopentylglycine or γ-methyl-L-leucine or (S)-2-amino-4,4-dimethylpentanoic acid or β-tert-butyl-L-alanine |
| Nva | L-Norvaline |
| PBS | Phosphate-buffered saline |
| pERK | Phosphorylated ERK or Phospho-ERK |
| Pbf | 2,2,4,6,7-Pentamethyldihydrobenzofuran-5-sulfonyl |
| Pen | L-Penicillamine or 3,3-dimethyl-L-cysteine or 3-mercapto-L-valine or L-(+)-2-amino-3-mercapto-3-methylbutanoic acid |
| Phe | L-Phenylalanine |
| Pro | L-Proline |
| PyAOP | (7-Azabenzotriazol-1-yloxy)tripyrrolidinophosphonium hexafluorophosphate |
| R8 | (A)-2-(7'-Octenyl)alanine or α-Me-D-Gly(7'-octenyl)-OH |
| rpm | Rotation per minute |
| S5 | (S')-α-(4'-Pentenyl)alanine or α-Me-L-Gly(4'-pentenyl)-OH |
| Ser | L-Serine |
| SOS | Son of Sevenless |
| SPPS | Solid Phase Peptide Synthesis |
| SUMO | Small Ubiquitin-like Modifier |
| T34Me2cPP | (1R,2S,5S)-6,6-Dimethyl-3-azabicyclo-[3.1.0]hexane-2-carboxylic acid |
| T3OHP | trans-3-Hydroxy-L-Pro or (2S,3S)-3-hydroxypyrrolidine-2-carboxylic acid |
| T3PhP | trans-3-Ph-L-Pro or (2S,3R)-3-phenyl-pyrrolidine-2-carboxylic acid |
| tBu | tert-butyl |
| TCEP | Tris(2-carboxyethyl)phosphine |
| TFA | Trifluoroacetic acid |
| THF | Tetrahydrofuran |
| Tic | (5)-1,2,3,4-tetrahydroisoquinoline-3-carboxylic acid |
| TIS | Triisopropylsilane |
| Thr | L-Threonine |
| TR-FRET | Time-Resolved Fluorescence Resonance Energy Transfer |
| Trp | L-Tryptophan |
| Trt | Trityl |

-continued

| Abbreviation | Definition |
| --- | --- |
| Tyr | L-Tyrosine |
| UPLC | Ultra Performance Liquid Chromatography or Ultrahigh Pressure Liquid Chromatography |
| Val | L-Valine |
| VC | Volume column |
| YBzl | O-Benzyl-L-tyrosine |
| YCF3 | O-(Trifluoromethyl)-L-tyrosine or (2S)-2-amino-3-[4-(trifluoromethoxy)phenyl]propanoic acid |

Dosages of the Compounds of Formula (I)

The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the invention is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula (I) and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition. Administering of the drug to the subject includes both self-administration and administration to the patient by another person. The subject may be in need of, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

The present invention also provides pharmaceutical compositions comprising a compound of Formula (I). The compound of Formula (I) can be used in combination with any suitable pharmaceutical carrier or excipient. Such pharmaceutical compositions comprise a therapeutically effective amount of one or more compounds of Formula (I), and pharmaceutically acceptable excipient(s) and/or carrier(s). The specific pharmaceutic composition will suit the mode of administration. In particular aspects, the pharmaceutical acceptable carrier may be water or a buffered solution.

Excipients included in the pharmaceutical compositions have different purposes depending, for example on the nature of the drug, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

Carriers are compounds and substances that improve and/or prolong the delivery of an active ingredient to a subject in the context of a pharmaceutical composition. Carriers may serve to prolong the in vivo activity of a drug or slow the release of the drug in a subject, using controlled-release technologies. Carriers may also decrease drug metabolism in a subject and/or reduce the toxicity of the drug. Carriers can also be used to target the delivery of the drug to particular cells or tissues in a subject. Common carriers (both hydrophilic and hydrophobic carriers) include fat emulsions, lipids, PEGylated phospholipids, PEGylated liposomes, PEGylated liposomes coated via a PEG spacer with a cyclic RGD peptide c(RGDDYK) (SEQ ID. NO. 141), liposomes and lipospheres, microspheres (including those made of biodegradable polymers or albumin), polymer matrices, biocompatible polymers, protein-DNA complexes, protein conjugates, erythrocytes, vesicles, nanoparticles, and side-chains for hydro-carbon stapling. The aforementioned carriers can also be used to increase cell membrane permeability of the compounds of Formula (I). In addition to their use in the pharmaceutical compositions of the present invention, carriers may also be used in compositions for other uses, such as research uses in vitro (e.g., for delivery to cultured cells) and/or in vivo.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatin capsules include lactose, maize starch or derivatives thereof, stearic acid or salts thereof. Suitable excipients for use with soft gelatin capsules include for example vegetable oils, waxes, fats, semi-solid, or liquid polyols etc. For the preparation of solutions and syrups, excipients which may be used include for example water, polyols and sugars. For the preparation of suspensions oils, e.g., vegetable oils, may be used to provide oil-in-water or water in oil suspensions. In certain situations, delayed release preparations may be advantageous and compositions which can deliver the peptidomimetic macrocycles in a delayed or controlled release manner may also be prepared. Prolonged gastric residence brings with it the problem of degradation by the enzymes present in the stomach and so enteric-coated capsules may also be prepared by standard techniques in the art where the active substance for release lower down in the gastro-intestinal tract.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6):318 (1986).

Pharmaceutical compositions adapted for topical administration may be formulated as ointments, creams, suspensions, lotions, powders, solutions, pastes, gels, sprays, aerosols or oils. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water-for-injection, alcohols, polyols, glycerin and vegetable oils, for example. The compositions may be presented in unit-dose or multi-dose containers, for example sealed ampoules and vials, and may be stored in a freeze-dried (lyophilized) condition requiring only the addition of the sterile liquid carrier, for example water or saline for injections, immediately prior to use. Extemporaneous injection solutions and suspensions may be prepared from sterile powders, granules and tablets. The pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or anti-oxidants. They may also contain therapeutically-active agents in addition to the substance of the present invention.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication.

Methods of Using the Compounds of Formula (I)

The present application provides a method of inhibiting RAS-mediated cell signaling comprising contacting a cell with a compound of Formula (I) or a pharmaceutically acceptable salt thereof. Inhibition of RAS-mediated signal transduction can be assessed and demonstrated by a wide variety of ways known in the art. Non-limiting examples include (a) an increase in GTPase activity of RAS; (b) nucleotide exchange mediated by SOS; (c) an increase in $k_{off}$ of GTP or a decrease in $k_{off}$ of GDP; (d) a decrease in the levels of signaling transduction molecules downstream in the RAS pathway, such as a decrease in pMEK, pERK, or pAKT levels; (e) a decrease in binding of RAS complex to downstream signaling molecules including but not limited to Raf; (f) alteration of RAS microclustering, (g) membrane localization; and/or (h) assessment of protein levels. Kits and commercially available assays can be utilized for determining one or more of the above.

The present application also provides methods of using the compounds of Formula (I) (or their pharmaceutically acceptable salts) or pharmaceutical compositions containing such compounds to treat disease conditions, including but not limited to, conditions implicated by mutant K-Ras, proteins (e.g., cancer, including but not limited to colorectal adenocarcinoma, pancreatic exocrine neoplasm, non-small cell lung carcinoma, uterine corpus neoplasm, and ovarian neoplasm), and in some embodiments the K-Ras(G12D) mutant.

In some embodiments, a method for treatment of cancer is provided, the method comprising administering a therapeutically effective amount a compound of Formula (I) (or a pharmaceutically acceptable salt thereof) or any of the foregoing pharmaceutical compositions comprising such a compound to a subject in need of such treatment. In some embodiments, the cancer is mediated by a K-Ras mutation, e.g., the K-Ras(G12D) mutation.

In some embodiments the present invention provides a method of treating a disorder in a subject in need thereof, wherein the method comprises determining if the subject has a K-Ras mutation (e.g., K-Ras(G12D) mutation) and if the subject is determined to have the K-Ras, mutation, then administering to the subject a therapeutically effective amount of a compound of Formula (I) or a pharmaceutically acceptable salt thereof.

The disclosed compounds may inhibit anchorage-independent cell growth and therefore have the potential to inhibit tumor metastasis. Accordingly, another embodiment the present invention provides a method for inhibiting tumor metastasis, the method comprising administering an effective amount of a compound of Formula (I).

The disclosed compounds may inhibit tumor immunity evasion. Accordingly, another embodiment the present invention provides a method for inhibiting tumor immunity evasion, the method comprising administering an effective amount of a compound of Formula (I).

K-Ras mutations have also been identified in hematological malignancies (e.g., cancers that affect blood, bone marrow and/or lymph nodes). See, e.g., Braun B S et al., *Proc Natl Acad Sci USA*. 2004 Jan. 13; 101(2):597-602. Accordingly, certain embodiments are directed to administration of the compounds of Formula (I) (e.g., in the form of a pharmaceutical composition) to a subject in need of treatment of a hematological malignancy. Such malignancies include, but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds are useful for treatment of lymphomas such as Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a K-Ras mutation (e.g., the K-Ras(G12D) mutation) can be undertaken by assessing the nucleotide sequence encoding the K-RAS gene, by assessing the amino acid sequence of the K-Ras protein, or by assessing the characteristics of a putative K-Ras mutant protein. The sequence of the wild-type human K-Ras protein is known in the art.

Methods for detecting a mutation in a K-RAS nucleotide sequence are also known by those of skill in the art. These methods include, but are not limited to, polymerase chain reaction-restriction fragment length polymorphism (PCR-RFLP) assays, polymerase chain reaction-single strand conformation polymorphism (PCR—SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for K-Ras mutations (e.g., the K-Ras(G12D) mutation) by real-time PCR. In real-time PCR, fluorescent probes specific for a K-Ras, e.g., K-Ras(G12D), mutation are used. When a mutation is present, the probe binds and fluorescence is detected. In some embodiments, the K-RAS mutation is identified using a direct sequencing method of specific regions (e.g., exon 2 and/or exon 3) in the K-RAS gene.

Methods for detecting a mutation in the K-Ras protein (e.g., the K-Ras(G12D) mutation) are known by those of skill in the art. These methods include, but are not limited to, detection of a K-Ras mutant using a binding agent (e.g., an antibody) specific for the mutant protein, protein electrophoresis and Western blotting, and direct peptide sequencing.

A number of tissue samples can be assessed for determining whether a tumor or cancer comprises a K-Ras mutation (e.g., the K-Ras(G12D) mutation). In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The present application also provides a method of treating a hyperproliferative disorder comprising administering a therapeutically effective amount of a compound of the invention, or a pharmaceutically acceptable salt thereof to a subject in need thereof. In some embodiments, said method relates to the treatment of a subject who suffers from a cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer; multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer; small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating pancreatic cancer, colorectal cancer or lung cancer. In certain embodiments, the cancer is pancreatic ductal adenocarcinoma, colorectal cancer, or lung adenocarcinomal.

The present invention also provides methods of modulating mutant K-Ras protein activity (e.g., activity resulting from the K-Ras(G12D) mutation) by contacting the protein with an effective amount of a compound of Formula (I). Modulation can be inhibiting protein activity. In some embodiments, the present invention provides methods of inhibiting protein activity by contacting the mutant K-Ras protein (e.g., K-Ras(G12D) mutation) with an effective amount of a compound of Formula (I) in solution. In some embodiments, the present invention provides methods of inhibiting the mutant K-Ras protein activity by contacting a cell, tissue, or organ that expresses the protein of interest. In some embodiments, the disclosure provides methods of inhibiting protein activity in subjects including but not limited to rodents and mammals (e.g., humans) by administering into the subjects an effective amount of a compound of Formula (I).

Combination Therapies

One or more additional pharmacologically active agents may be administered in combination with a compound of Formula (I) (or a pharmaceutically acceptable salt thereof). An additional active agent (or agents) is intended to mean a pharmaceutically active agent (or agents) that is active in the body, including pro-drugs that convert to pharmaceutically active form after administration, which are different from the compound of Formula (I). The additional active agents also include free-acid, free-base and pharmaceutically acceptable salts of said additional active agents. Generally, any suitable additional active agent or agents, including chemotherapeutic agents or therapeutic antibodies may be used in any combination with the compound of Formula (I) in a single dosage formulation (a fixed dose drug combination), or in one or more separate dosage formulations which allows for concurrent or sequential administration of the active agents (co-administration of the separate active agents) to subjects. In addition, the compounds of Formula (I) (or pharmaceutically acceptable salts thereof) can be administered in combination with radiation therapy, hormone therapy, surgery or immunotherapy.

The present application also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes but is not limited to the combination of one or more compounds of Formula (I) with chemotherapeutic agents, therapeutic antibodies, and radiation treatment, to provide a synergistic or additive therapeutic effect.

In one embodiment, the combination therapies comprise chemotherapeutic agents. Many such agents are presently known in the art and can be used in combination with the compounds of Formula (I). In some embodiments, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), and Adriamycin as well. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™ chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifiuridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxy tamoxifen, trioxifene, keoxifene, LY 117018, onapristone, and toremifene; and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); and topoisomerase inhibitor RFS 2000.

Where desired, the compounds of Formula (I) or pharmaceutical compositions containing such compounds can be used in combination with commonly prescribed anti-cancer drugs such as Herceptin®, Avastin®, Erbitux®, Rituxan®, Taxol®, Arimidex®, Taxotere®, ABVD, AVICINE, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, Antineoplastic, antitumorigenic herbs, apaziquone, atiprimod, azathioprine, belotecan, bendamustine, BMW 2992, biricodar, brostallicin, bryostatin, buthionine sulfoximine, calyculin, cell-cycle nonspecific antineoplastic agents, dichloroacetic acid, discodermolide, elsamitrucin, enocitabine, epothilone, eribulin, everolimus, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pixantrone, proteasome inhibitor, rebeccamycin, resiquimod, rubitecan, SN-38, salinosporamide a, sapacitabine, swainsonine, talaporfin, tariquidar, tegafur-uracil, temozolimide, tesetaxel, triplatin tetranitrate, tris(2-chloroethyl)amine, troxacitabine, Vadimezan, Vinflunine, ZD6126 or Zosuquidar.

The present application further provides a method for using the compounds of Formula (I) or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of Formula (I) in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive microspheres.

The compounds of Formula (I) or pharmaceutical compositions containing such compounds can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors and MMP-9 (matrix-metalloproteinase 9) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful matrix metalloproteinase inhibitors are described in WO 96/33172, WO 96/27583 European Patent Publication No. EP0818442, European Patent Publication No. EP1004578, WO 98/07697, WO 98/03516, WO 98/34918, WO 98/34915, WO 98/33768, WO 98/30566, European Patent Publication No. 606046, European Patent Publication No. 931788, WO 90/05719, WO 99/52910, WO 99/52889, WO 99/29667, WO 1999007675, European Patent Publication No. EP1786785, European Patent Publication No. EP1181017, U.S. Publication No. US20090012085, U.S. Pat. Nos. 5,863,949, 5,861,510, and European Patent Publication No. EP0780386. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the combinations are AG-3340, RO 32-3555, and RS 13-0830.

The compounds of Formula (I) may also be used in co-therapies with other antineoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RH retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of Formula (I) may further be used with VEGFR inhibitors.

In some embodiments, the combination comprises a composition of the present invention in combination with at least one anti-angiogenic agent. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™, KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRES S A™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met". Other anti-angiogenic agents include Campath, IL-8, B-FGF, Tek antagonists (Ceretti et al, U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; and 6,057,124), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide (Merck KGaA, Germany); pegaptanib octasodium, (Gilead Sciences, USA); alphastatin (BioActa, UK); M-PGA, ilomastat, (Arriva, USA); emaxanib, (Pfizer, USA); vatalanib (Novartis, Switzerland); 2-methoxyestradiol; TLC ELL-12 (Elan, Ireland); anecortave acetate (Alcon, USA); alpha-D148 Mab, (Amgen, USA); CEP-7055 (Cephalon, USA); anti-Vn Mab (Crucell, Netherlands) angiocidin (InKine Pharmaceutical, USA); KM-2550 (Kyowa Hakko, Japan); SU-0879 (Pfizer, USA); CGP-79787 (Novartis, Switzerland, EP 970070); fibrinogen-E fragment (BioActa, UK); TBC-1635 (Encysive Pharmaceuticals, USA); SC-236 (Pfizer, USA); metastatin (EntreMed, USA); maspin (Sosei, Japan); ER-68203-00 (IVAX, USA); benefin (Lane Labs, USA); Tz-93 (Tsumura, Japan); TAN-1120 (Takeda, Japan); FR-111142 (Fujisawa, Japan); platelet factor 4; vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and Medlmmune, USA); enzastaurin hydrochloride (USAN), (Lilly, USA); CEP 7055, (Cephalon, USA and Sanofi-Synthelabo, France); BC 1, (Genoa Institute of Cancer Research, Italy); rBPI 21 and BPI-derived antiangiogenic (XOMA, USA); PI 88 (Progen, Australia); cetuximab, (Aventis, France); AVE 8062 (Ajinomoto, Japan); AS 1404, (Cancer Research Laboratory, New Zealand); SG 292, (Telios, USA); endostatin, (Boston Childrens Hospital, USA); ANGIOSTATIN (Boston Childrens Hospital, USA); AZD 6474, (AstraZeneca, UK); ZD 6126 (Angiogene Pharmaceuticals, UK); PPI 2458, (Praecis, USA); AZD 9935 (AstraZeneca, UK); AZD 2171 (AstraZeneca, UK); vatalanib (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); SDX 103, (University of California at San Diego, USA); PX 478, (ProlX, USA);

METASTATIN (EntreMed, USA); troponin I, (Harvard University, USA); SU 6668, (SUGEN, USA); OXI 4503 (OXiGENE, USA); motuporamine C, (British Columbia University, Canada); CDP 791 (Celltech Group, UK); atiprimod (GlaxoSmithKline, UK); E 7820 (Eisai, Japan); CYC 381 (Harvard University, USA); AE 941 (Aeterna, Canada); urokinase plasminogen activator inhibitors; HIF-1 alfa inhibitors; angiocidin (InKine, USA); GW 2286 (GlaxoSmithKline, UK); EHT 0101 (ExonHit, France); CP 868596 (Pfizer, USA); CP 564959 (OSI, USA); CP 547632 (Pfizer, USA); 786034, (GlaxoSmithKline, UK); KRN 633 (Kirin Brewery, Japan); tumor necrosis factor-alpha inhibitors; KDR kinase inhibitors; combretastatin A4 prodrug (Arizona State University, USA); chondroitinase AC (IBEX, Canada); BAY RES 2690 (Bayer, Germany); tetrathiomolybdate (University of Michigan, USA); GCS 100 (Wayne State University, USA) CV 247 (Ivy Medical, UK); CKD 732, (Chong Kun Dang, South Korea); MAb, vascular endothelium growth factor, (Xenova, UK); irsogladine (Nippon Shinyaku, Japan); RG 13577 (Aventis, France); VE-cadherin-2 antagonists; vasostatin, (National Institutes of Health, USA); Flk-1, (ImClone Systems, USA); TZ 93 (Tsumura, Japan); TumStatin (Beth Israel Hospital, USA); forms of FLT 1 (vascular endothelial growth factor receptor 1); Tie-2 ligands (Regeneron, USA); and thrombospondin 1 inhibitor (Allegheny Health, USA).

Additional active compounds/agents that can be used in the treatment of cancers and that can be used in combination with one or more compounds of Formula (I) include: epoetin alfa; darbepoetin alfa; panitumumab; pegfilgrastim; palifermin; filgrastim; denosumab; ancestim or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, ERK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific anti-sense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib, and lapatinib.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, *Br. J. Cancer* 67:247-253; Teramoto, T., et al., 1996, *Cancer* 77:639-645; Goldstein et al, 1995, *Clin. Cancer Res.* 1: 1311-1318; Huang, S. M., et al., 1999, *Cancer Res.* 15:59 (8): 1935-40; and Yang, X., et al., 1999, *Cancer Res.* 59: 1236-1243. The EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl) piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl] phenol hydrochloride available from Axon Medchem), PIK 75 (N'-[(1E)-(6-bromoinddazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-mo holin-4-yl-thieno[3,2-d]pyrimidine bismesylate available from Axon Medchem), AS-252424 (5-[1-[5-(4-fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Akt1) (Barnett et al. (2005) *Biochem. J.*, 385 (Pt. 2), 399-408); Akt-1-1,2 (Barnett et al. (2005) *Biochem. J.* 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134(12 Suppl), 3493 S-3498S); perifosine; Dasmahapatra et al. (2004) *Clin. Cancer Res.* 10(15), 5242-52, 2004); phosphatidylinositol ether lipid analogues (e.g., Gills and Dennis (2004) *Expert. Opin. Investig. Drugs* 13, 787-97); and triciribine (TCN or API-2 or NCI identifier: NSC 154020; Yang et al. (2004) Cancer Res. 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g., as disclosed in WO 98/02441 and WO 01/14387, e.g., AP23573, AP23464, or AP23841; 40-(2-hydroxyethyl) rapamycin, 40-[3-hydroxy(hydroxymethyl)methylpropanoate]-rapamycin, 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05016252).

MCl-1 inhibitors include, but are not limited to, AMG-176, MIK665, and 563845.

Proteasome inhibitors include, but are not limited to, Kyprolis® (carfilzomib), Velcade® (bortezomib), and oprozomib.

Immune therapies include, but are not limited to, anti-PD-1 agents, anti-PD-L1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

In a particular embodiment, the compounds of Formula (I) are used in combination with an anti-PD-1 antibody. In certain embodiments, the anti-PD-1 antibody is pembrolizumab, cemiplimab, or nivolumab. In a specific embodiment, the anti-PD-1 antibody is pembrolizumab.

In other embodiments, the compounds of Formula (I) are used in combination with an anti-PD-L1 antibody, such as atezolizumab, durvalumab, or avelumab.

In some embodiments, the compounds of Formula (I) are used in combination with an anti-CTLA-4 antibody, e.g., ipilumumab.

The compounds of the invention can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXAMPLES

The following examples are provided so that the invention might be more fully understood. The examples include methods for preparing the compounds of Formula (I) and testing such compounds in biochemical and cellular assays. The examples should not be construed as limiting the invention in any way.

Several methods for preparing the compounds of Formula (I) are described in the following Schemes and Examples. Starting materials and intermediates are purchased, made from known procedures, or as otherwise illustrated. Some frequently applied routes to the compounds of Formula (I) are also described by the Schemes as follows. In some cases the order of carrying out the steps of reaction schemes may be varied to facilitate the reaction or to avoid unwanted reaction products.

A. Generalized Procedure for Synthesizing Linear Peptide Precursors

Peptides in FIG. 1A to FIG. 1H were synthesized using standard solid phase synthesis using Fmoc/tert-Bu chemistry as exemplified in Chan, W. C.; White, P. D. "Fmoc Solid-Phase Synthesis: a Practical Approach", Oxford University Press, Oxford, 2000; Steward, J.; Young, J. "Solid Phase Peptide Synthesis", Pierce Chemical Company, Rockford, 1984.; N. L. Benoiton, "Chemistry of Peptide Synthesis", CRC Press, New York, 2006; and Lloyd-Williams, P.; Albericio, F. "Chemical Approaches to the Synthesis of Peptides and Proteins", CRC Press, New York, 1997. Section B, below, describes approaches for cyclizing such peptides to form mono- and bicyclic peptides.

The α-amino group of each amino acid was protected by a 9H-fluoren-9-ylmethoxycarbonyl group (Fmoc) during the coupling of the carboxylic acid of the amino acid with the free amino terminus of the peptide attached to the resin. To avoid any side reactions during the coupling steps performed in DMF, the reactive side-chains of amino acids also carry acid-labile protecting groups that effectively mask the reactive groups until treatment of the resin with acid during the cleavage of the peptide from the solid support. After completion of each coupling step, the Fmoc group of the just-attached amino acid was removed with piperidine or 4-methylpiperidine and the resin was thoroughly washed to prepare for the coupling of the subsequent Fmoc-protected amino acid derivative.

The side chain protecting groups were: tert-butyl (tBu) for L-Asp, L-Glu, α-Me-L-Ser, L-Ser, L-Thr and L-Tyr; trityl (Trt) for L-Asn, L-Cys, D-Cys, L-hCys, D-hCys, L-Pen, D-Pen, and L-Gln; tert-butoxy-carbonyl (Boc) for L-Lys, L-Trp, L-His; and, 2,2,4,6,7-pentamethyldihydrobenzofuran-5-sulfonyl (Pbf) for L-Arg, D-Arg, L-homoArg, N-Me-L-Arg.

Fmoc-protected amino acids were typically obtained from vendors such as Sigma-Aldrich, Novabiochem, Chem-Impex, Combi-Block.

B. Synthetic Procedures Used to Prepare Cyclic Peptides

Synthetic Procedures A-F describe synthetic procedures used to prepare SEQ ID Nos: 1-66, including cyclization and purification of peptides. Table 2 below specifies the procedure used to prepare the peptide.

TABLE 2

| Seq ID No: | Procedure |
| --- | --- |
| 1 | B |
| 2 | C |
| 3 | F |

TABLE 2-continued

| Seq ID No: | Procedure |
|---|---|
| 4 | C |
| 5 | B |
| 6 | A |
| 7 | C |
| 8 | D |
| 9 | C |
| 10 | A |
| 11 | B |
| 12 | B |
| 13 | C |
| 14 | B |
| 15 | C |
| 16 | A |
| 17 | A |
| 18 | B |
| 19 | C |
| 20 | A |
| 21 | A |
| 22 | B |
| 23 | A |
| 24 | B |
| 25 | C |
| 26 | C |
| 27 | C |
| 28 | A |
| 29 | A |
| 30 | C |
| 31 | C |
| 32 | C |
| 33 | A |
| 34 | C |
| 35 | A |
| 36 | A |
| 37 | C |

TABLE 2-continued

| Seq ID No: | Procedure |
|---|---|
| 38 | A |
| 39 | A |
| 40 | C |
| 41 | A |
| 42 | A |
| 43 | A |
| 44 | C |
| 45 | A |
| 46 | C |
| 47 | A |
| 48 | A |
| 49 | A |
| 50 | A |
| 51 | C |
| 52 | A |
| 53 | C |
| 54 | A |
| 55 | A |
| 56 | A |
| 57 | E |
| 58 | C |
| 59 | B |
| 60 | A |
| 61 | A |
| 62 | A |
| 63 | A |
| 64 | A |
| 65 | A |
| 66 | A |

For specific compounds, additional details involved in their preparation are described in Section C below.

1. Synthetic Procedure A

Synthetic Scheme 1
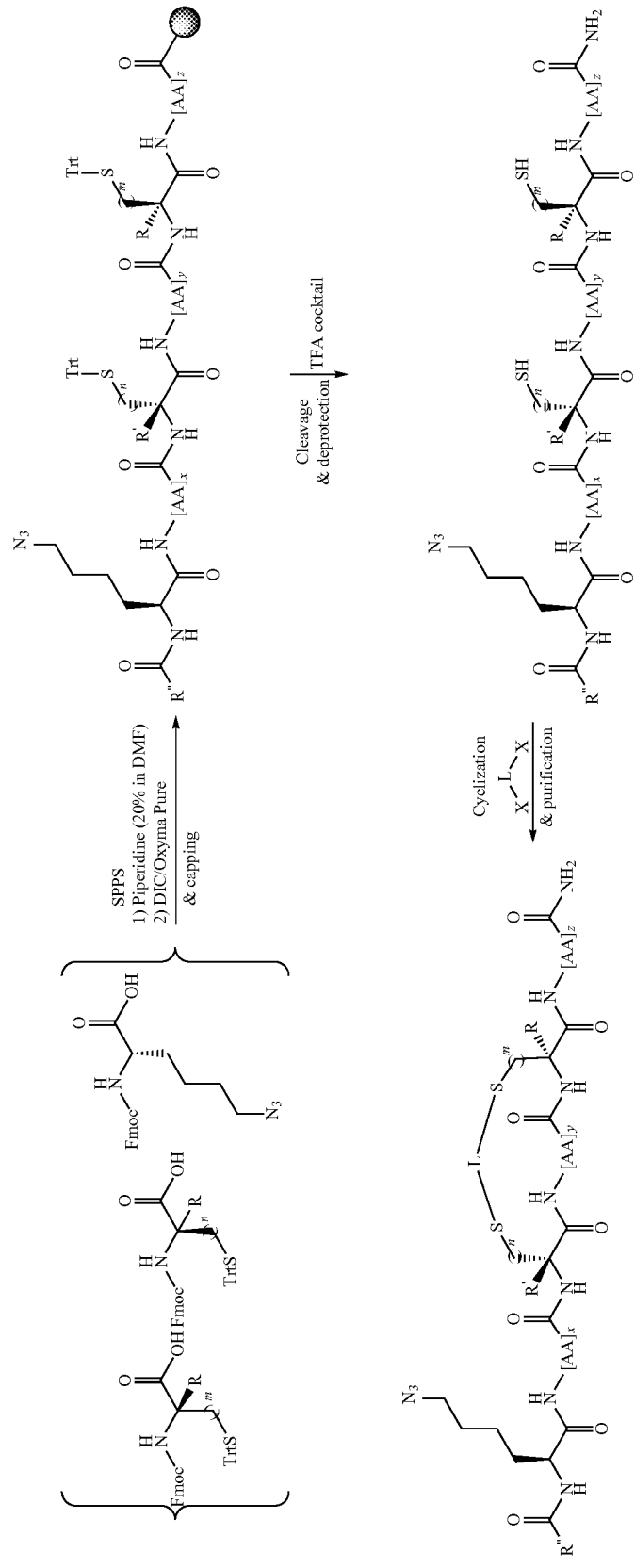

Solid Phase Synthesis of Peptides (SPPS)

Peptides were synthesized on a Liberty Blue™ synthesizer from CEM Corporation, using standard solid phase synthesis using Fmoc/t-Bu chemistry as summarized above.

N,N'-Diisopropylcarbodiimide (DIC) with ethyl cyano(hydroxyimino)acetate (Oxyma Pure) were used as coupling agents to create the amide bond between the free amino terminus of the resin-bound protected peptide and the carboxylic acid of the Fmoc-protected amino acid.

Unloaded Rink amide MBHA (4-Methylbenzhydrylamine) resin (100-200 mesh, 0.36 mmol/g loading, 1% cross-linked polystyrene, Novabiochem) was used for synthesis.

All the amino acids were dissolved at a 0.2 M concentration in anhydrous DMF (N,N-dimethylformamide). The amino acids were activated with equimolar amounts of Oxyma Pure solution (0.5 M in anhydrous DMF), and a 2-fold molar excess of DIC solution (1.0 M in anhydrous DMF).

Reactions were typically performed at the 0.1 mmol scale.

Every synthesis cycle included: Fmoc amino acid deprotection by 20% piperidine in anhydrous DMF (90° C. microwave assisted heating, 2 min) and coupling (potentially repeated twice for difficult couplings) with Fmoc-protected amino acid/DIC/Oxyma (5, 5, and 10 equiv respectively; 90° C. microwave assisted heating, 2 min or 4 min). Cycles of Fmoc deprotection and Fmoc-protected amino acid coupling were repeated with the desired monomers until the full linear peptide was formed. When required, a final acylation (capping) step was performed using acetic anhydride (10% in DMF; 75° C. for 10 min).

Cleavage and Deprotection

The linear resin-bound peptides were deprotected and cleaved from the solid support by treatment with TFA/$H_2O$/TIS/DTT (92.5:2.5:2.5:2.5, v/v; 10 mL) at 38° C. for 30 min using a Razor® peptide cleavage system from CEM Corporation. After filtration of the resin, crude linear peptides were precipitated from the TFA cleavage solution using cold tert-butyl methyl ether (TBME; 40 mL) and collected by centrifugation (4000 rpm). The crude peptide was washed with cold TBME (35 mL) and blown dried by a stream of nitrogen gas.

Peptide Cyclization

After solid phase synthesis and cleavage, crude peptides were dissolved in acetonitrile/DI water (1:1, v/v, 20 mL, degassed). 1,4-Dithiothreitol (DTT, 1 equiv) and diiodomethane (10 equiv) were added. $NH_4HCO_3$ (200 mM solution in DI water, degassed) was added to adjust the pH to 8. The resulting reaction mixture was stirred at room temperature for approximately 4 hours and monitored by LC-MS. After the reaction was complete, the reaction solution was quenched by addition of TFA (200 frozen and lyophilized.

HPLC Purification

Purification was performed by preparative reversed-phase high performance liquid chromatography (RP-HPLC) on Waters XSelect Peptide CSH C18 OBD Prep column (130 Å, 5 µm, column size 150×30 mm) using a Waters MS-Directed AutoPurification HPLC/MS system. Mobile phase: (A) 0.1% TFA in HPLC water and (B) 0.1% TFA in HPLC acetonitrile; flow rate: 50 mL/min; UV wavelength $\lambda$=214 nm; gradient: 5% B over 17 min. UV absorbing fractions containing the target m/z ions were collected and the fractions containing product were confirmed by LC/MS.

Purity of fractions was confirmed by UPLC, which was measured by a reverse phase Waters Acquity UPLC-MS system. Column: Waters XSelect CSH C18 XP Column (130 Å, 2.5 µm, column size 50×2.1 mm). Mobile phase: (A) 0.1% TFA in HPLC water and (B) 0.1% TFA in HPLC acetonitrile; gradient: 5-100% B in 14 min; injection volume: 0.5 µL; flow rate: 1 mL/min; UV wavelength $\lambda$=214 nm.

Lyophilization of combined fractions containing pure peptide resulted in the final cyclized product as a powder.

2. Synthetic Procedure B

Synthetic Scheme 2
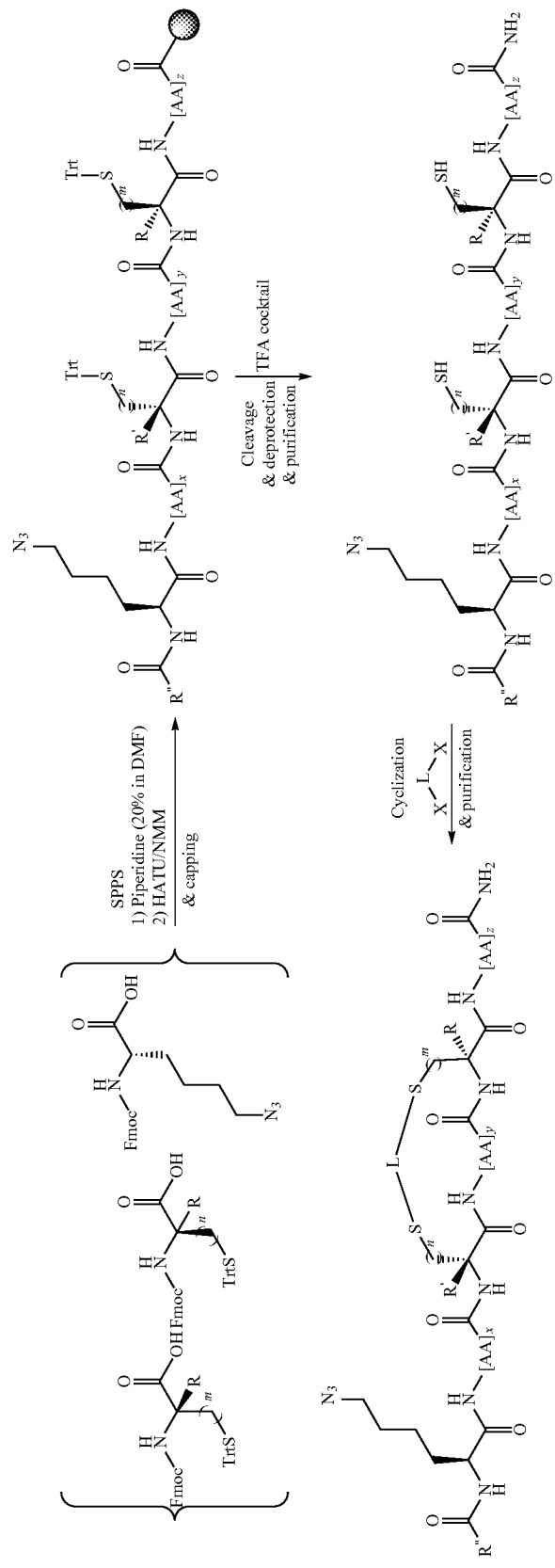

Solid Phase Synthesis of Peptides

Peptides were synthesized on a Symphony® X synthesizer (Gyros Protein Technologies), using standard solid phase synthesis using Fmoc/t-Bu chemistry as summarized above.

1-[Bis(dimethylamino)methylene]-1H-1,2,3-triazolo[4,5-b]pyridinium 3-oxide hexafluorophosphate (HATU) was used as a coupling agent to create the amide bond between the free amino terminus of the resin-bound protected peptide and the carboxylic acid of the Fmoc-protected amino acid. HATU solution was used within 5 days of preparation.

Unloaded Rink amide MBHA resin (100-200 mesh, 0.36 mmol/g loading, 1% cross-linked polystyrene, Novabiochem) was used for synthesis.

All the amino acids were dissolved at a 0.2 M concentration in anhydrous DMF. The amino acids were activated with equimolar amounts of HATU solution (0.5 M in anhydrous DMF), and a 2-fold molar excess of NMM (N-Methylmorpholine) solution (1.0 M in anhydrous DMF).

Reactions were typically performed at the 0.1 mmol scale.

Every synthesis cycle included: Fmoc amino acid deprotection by 20% (v/v) piperidine or 4-methylpiperidine in anhydrous DMF (room temperature; 3×3 min) and coupling (potentially repeated twice for difficult couplings) with Fmoc-protected amino acid/HATU/NMM (5, 5, and 10 equiv respectively; room temperature; 40 min). Cycles of Fmoc deprotection and Fmoc-protected amino acid coupling were repeated with the desired monomers until the full linear peptide was formed. When required, a final acylation (capping) step was performed using acetic anhydride (1.0 M) and DIPEA (2.0 M) in NMP (N-Methyl-2-pyrrolidone) at room temperature for 10 min.

Cleavage and Deprotection

The linear resin-bound peptides were deprotected and cleaved from the solid support by treatment with TFA/DTT/thioanisole/phenol/$H_2O$ (87.5/2.5/5/2.5/2.5, v/v, 8 mL) at room temperature for 3 h. After filtration of the resin, crude linear peptides were precipitated from the TFA cleavage solution using cold TBME (40 mL) and collected by centrifugation (4000 rpm). The crude peptide was washed with cold TBME (35 mL) and the residue was dissolved in acetonitrile/water (1:1, v/v, 15 mL) and lyophilized to dryness.

Intermediate Purification

The crude solids were redissolved in DMSO (1 mL) and was purified by Teledyne ISCO flash chromatography (15.5 g RediSep Rf Gold® Reversed-phase HP C18 Aq column) with gradient 20-60% ACN in water with 0.1% TFA as modifier (flowrate=30 mL/min). Fractions containing the desired product were collected and lyophilized to give the linear product.

Peptide Cyclization

After solid phase synthesis and cleavage, crude peptides were dissolved in acetonitrile/water (1:1, v/v, 10 mL). $NH_4HCO_3$ (0.2 M solution in water) was added to adjust the pH to ~8. 3,6-Dioxa-1,8-octanedithiol (DODT, 2 equiv) and diiodomethane (20 equiv) were added. Additional acetonitrile (2 mL) was added to make the reaction mixture homogeneous. The resulting reaction mixture was stirred at room temperature overnight and monitored by LC-MS. After the reaction was complete, the reaction mixture was frozen and lyophilized.

Final HPLC Purification

Purification was performed by preparative reversed-phase high performance liquid chromatography (RP-HPLC) on Waters XSelect Peptide CSH C18 OBD Prep column (130 Å, 5 µm, column size 150×30 mm) using a Waters MS-Directed AutoPurification HPLC/MS system. Mobile phase: (A) 0.1% TFA in water and (B) 0.1% TFA in acetonitrile; flow rate: 50 mL/min; UV wavelength $\lambda$=214 nm; gradient: 5% B over 17 min. UV absorbing fractions containing the target m/z ions were collected and the fractions containing product were confirmed by LC/MS.

Purity of fractions was confirmed by UPLC, which was measured by a reverse phase Waters Acquity UPLC-MS system. Column: Waters XSelect CSH C18 XP Column (130 Å, 2.5 µm, column size 50×2.1 mm). Mobile phase: (A) 0.1% TFA in water and (B) 0.1% TFA in acetonitrile; gradient: 5-100% B in 14 min; injection volume: 0.5 µL; flow rate: 1 mL/min; UV wavelength $\lambda$=214 nm.

Lyophilization of combined fractions containing pure peptide resulted in the final cyclized product as a powder.

3. Synthetic Procedure C

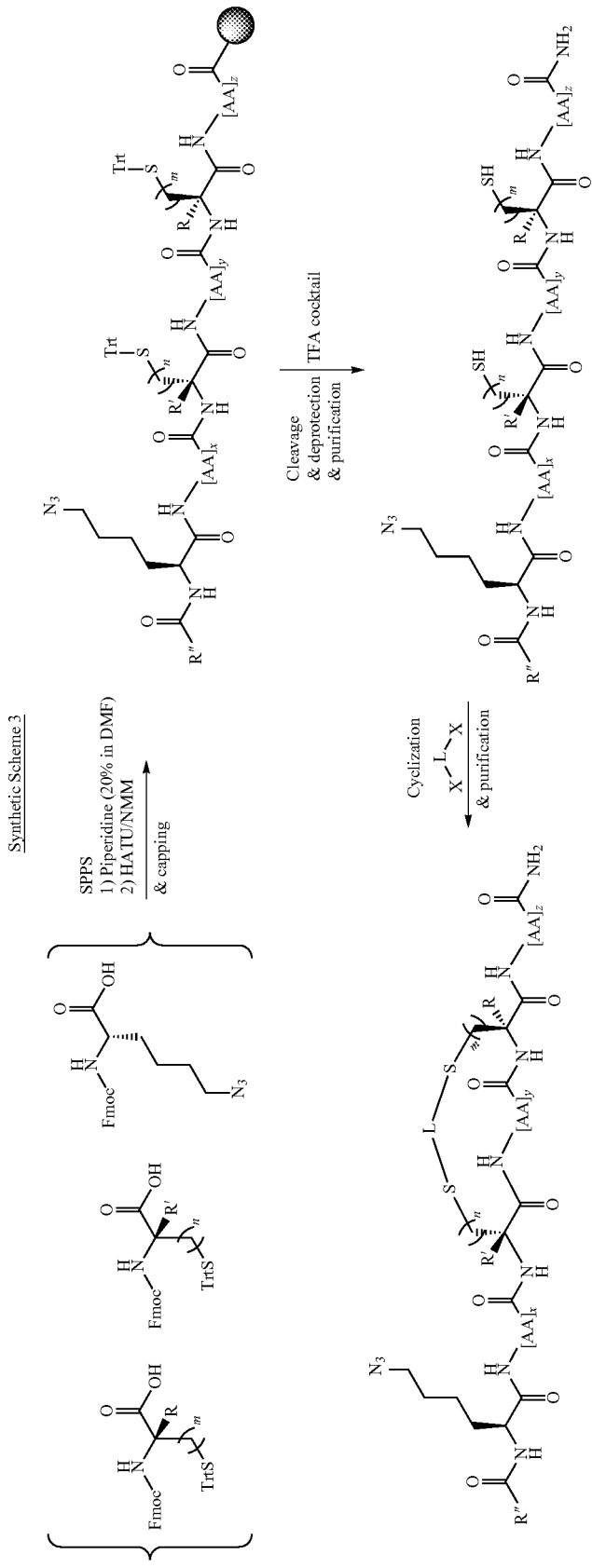

Solid Phase Synthesis of Peptides

Peptides were synthesized manually using standard solid phase synthesis using Fmoc/t-Bu chemistry as summarized above.

HATU with NMM were used as coupling agents to create the amide bond between the free amino terminus of the resin-bound protected peptide and the carboxylic acid of the Fmoc-protected amino acid.

Unloaded Rink amide MBHA resin (100-200 mesh, 1% cross-linked polystyrene) was used for synthesis. All the amino acids were dissolved at a 0.2 M concentration in anhydrous DMF.

Reactions were typically performed at the 0.3 mmol scale.

Every synthesis cycle included: (1) Fmoc amino acid deprotection: 20% piperidine in DMF (20 mL) was added into the resin. The mixture was kept at room temperature for 30 min while a stream of nitrogen was bubbled through it. The mixture was filtered, and the peptidyl resin was washed with DMF (5×20 mL); (2) Coupling (potentially repeated twice for difficult couplings) with Fmoc-protected amino acid/HATU/NMM (3, 2.85 and 6 equiv, respectively; room temperature; 1 h). Cycles of Fmoc deprotection and Fmoc-protected amino acid coupling were repeated with the desired monomers until the full linear peptide was formed. Final acylation (capping) step was performed using acetic anhydride capping solution [Capping Solution: Acetic anhydride (6 mL) and NMM (10 mL) in DMF (84 mL)].

Cleavage and Deprotection

The linear resin-bound peptides (~1.7 g of dry resin) were deprotected and cleaved from the solid support by treatment with TFA/EDT/Thioanisole/Phenol/$H_2O$ (87.5/2.5/5/2.5/2.5, v/v, 30 mL) at room temperature for 2.5 h. After filtration of the resin, crude linear peptides were precipitated from the TFA cleavage solution using cold diethyl ether (270 mL) and collected by centrifugation (4000 rpm). The precipitate was washed with cold diethyl ether (2×270 mL). The crude was dried under vacuum overnight to give the crude deprotected linear peptide as a solid (~450 mg).

Intermediate Purification

Purification was performed by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength $\lambda$=220 nm; gradient: 30% B over 60 min. UV absorbing fractions containing the target m/z ions were collected and the fractions containing product were confirmed by LC/MS.

Peptide Cyclization

The crude linear peptide (~0.06 mmol) was dissolved in a 1:1 mixture of water/ACN (30 mL). DODT (2 equiv) was added and the mixture was stirred at 30° C. for 30 min. pH was adjusted to ~8 by addition of aqueous 0.2 M ammonium carbonate solution. Diiodomethane (20 equiv) and DODT (2 equiv) were added. The mixture was shaken at 30° C. overnight.

Final HPLC Purification

The crude cyclized peptide was purified by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength $\lambda$=220 nm; gradient: 30% B over 60 min. UV absorbing fractions containing the target m/z ions were collected and the fractions containing product were confirmed by LC/MS. Lyophilization of combined fractions containing pure peptide resulted in the final cyclized product as a powder.

Purity of fractions was confirmed by UPLC, which was measured by a reverse phase Hewlett Packard 1100 UPLC-MS system. Column: Sepax GP-C18 Column (120 Å, 5 μm, column size 150×4.6 mm). Mobile phase: (A) 0.1% TFA in water and (B) 0.09% TFA in 80% ACN+20% $H_2O$; gradient: 10% B in 20 min; flow rate: 1 mL/min; UV wavelength $\lambda$=220 nm. The peptide was characterized by electrospray mass spectrometry on an Agilent 1260-6120 Quadrupole LC/MS.

4. Synthetic Procedure D

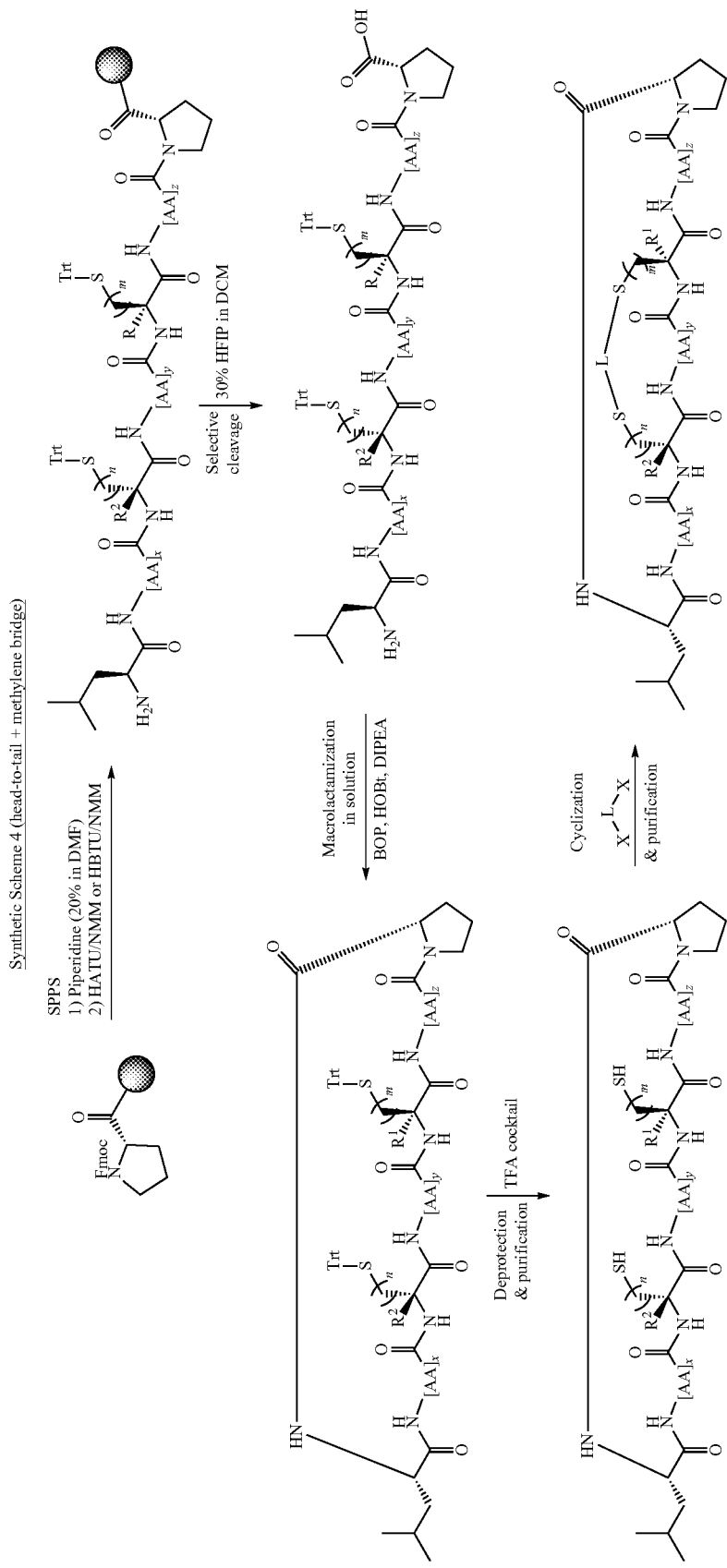

Solid Phase Synthesis of Peptides

Peptides were synthesized manually using standard solid phase synthesis using Fmoc/t-Bu chemistry as previously reported.

HBTU or HATU with NMM were used as coupling agents to create the amide bond between the free amino terminus of the resin-bound protected peptide and the carboxylic acid of the Fmoc-protected amino acid.

Fmoc-L-Pro-loaded Chlorotrityl Chloride (CTC) resin (100-200 mesh, 0.51 mmol/g loading, 1% cross-linked polystyrene) was used for synthesis.

All the amino acids were dissolved at a 0.2 M concentration in anhydrous DMF.

Reactions were typically performed at the 0.2 mmol scale.

Every synthesis cycle included: (1) Fmoc amino acid deprotection: 20% Piperidine in DMF (20 mL) was added into the resin. The mixture was kept at room temperature for 30 min while a stream of nitrogen was bubbled through it. The mixture was filtered, and the peptidyl resin was washed with DMF (5×20 mL); (2) Coupling (potentially repeated twice for difficult couplings) with Fmoc-protected D-amino acid/HATU/NMM (3, 2.85, and 6 equiv respectively, room temperature; 1 h) or with Fmoc-protected L-amino acid/HBTU/NMM (3, 2.85, and 6 equiv respectively, room temperature; 1 h). Cycles of Fmoc deprotection and Fmoc-protected amino acid coupling were repeated with the desired monomers until the full linear peptide was formed. Full linear peptidyl resin was washed with DMF (5×20 mL). Then peptidyl resin was washed with MeOH (2×20 mL), DCM (2×20 mL) and MeOH (2×20 mL). The resin was dried under vacuum overnight.

Selective Cleavage of Protected Peptide and Macrolactamization

For the cleavage of the protected linear peptide from the solid support, the peptidyl resin (~1 g) was treated with 30% hexafluoroisopropanol (HFIP) in DCM for 1 h at room temperature, filtered, and the solvent was removed under reduced pressure.

The resulting residue was dissolved in DMF (100 mL). HOBT (18 equiv), DIPEA (6 equiv) and BOP (3 equiv) were added. The mixture was shaken for 3 h at room temperature. Upon completion of the macrolactamization monitored by UPLC-MS, the solvent was removed under reduced pressure.

Deprotection

TFA/$H_2O$ (95/5, v/v, 35 mL) and DTT (2 mmol) were added to the crude protected cyclic peptide. The mixture was shaken for 2.5 h at room temperature. Cold diethyl ether (180 mL) was added into the filtrate. The peptide was precipitated by centrifugation (4000 rpm). The precipitate was washed with diethyl ether (2×270 mL). The crude was dried under vacuum overnight to give the crude deprotected cyclic peptide as a solid.

Intermediate Purification

Purification was performed by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength $\lambda$=220 nm; gradient: 30% B over 60 min. UV absorbing fractions containing the target m/z ions were collected and the fractions containing product were confirmed by LC/MS.

Methylene Bridge Insertion

The intermediate cyclic peptide (~0.03 mmol) was dissolved in a 1:1 mixture of water/ACN (13 mL). DODT (2 equiv) was added and the mixture was stirred at 30° C. for 30 min. pH was adjusted to ~8 by addition of aqueous 0.2 M ammonium carbonate solution. Diiodomethane (20 equiv) and DODT (2 equiv) were added. The mixture was shaken at 30° C. overnight.

Final HPLC Purification

The final crude peptide was purified by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength $\lambda$=220 nm; gradient: 30% B over 60 min. UV absorbing fractions containing the target m/z ions were collected and the fractions containing product were confirmed by LC/MS. Lyophilization of combined fractions containing pure peptide resulted in the final cyclized product as a powder.

5. Synthetic Procedure E

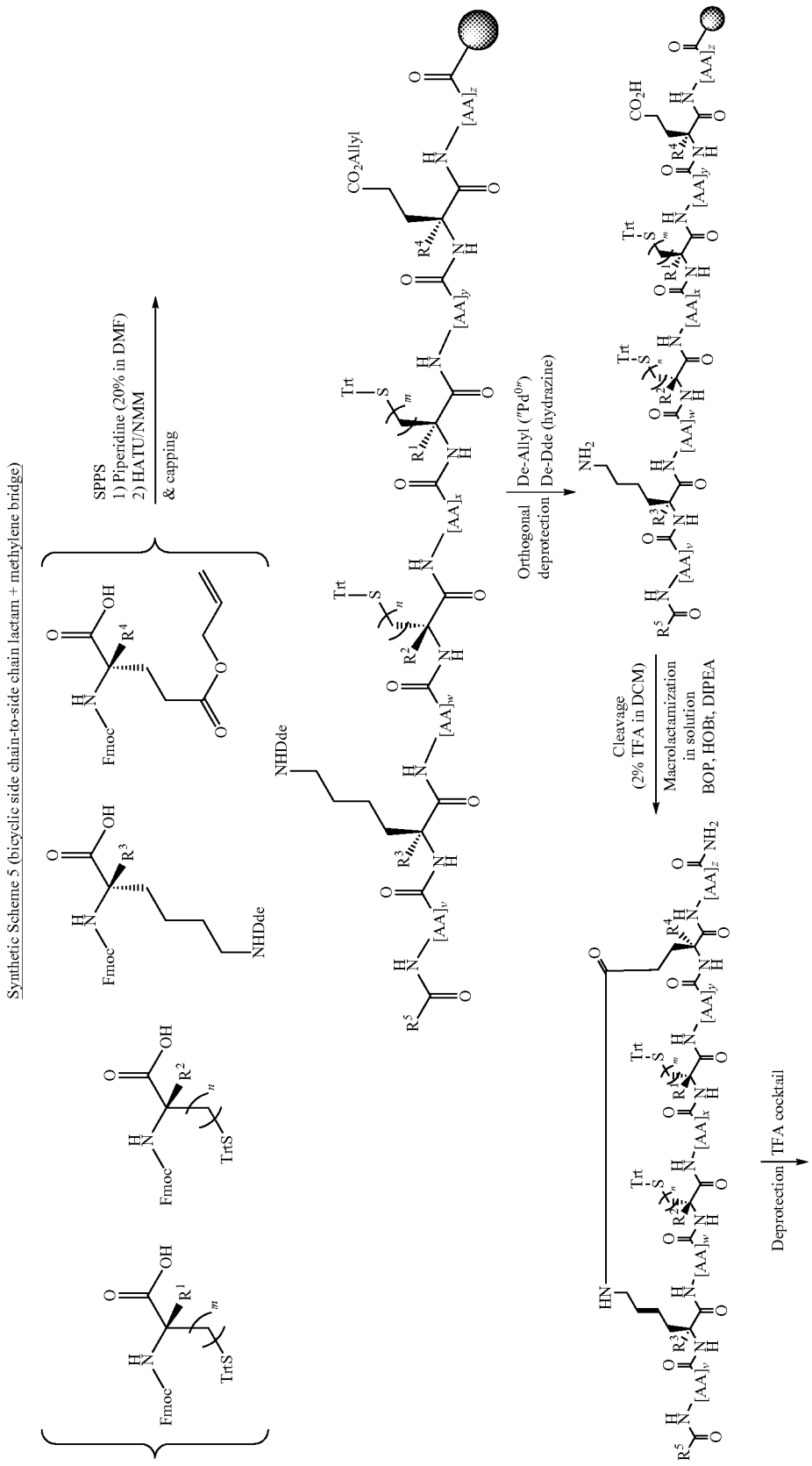

-continued
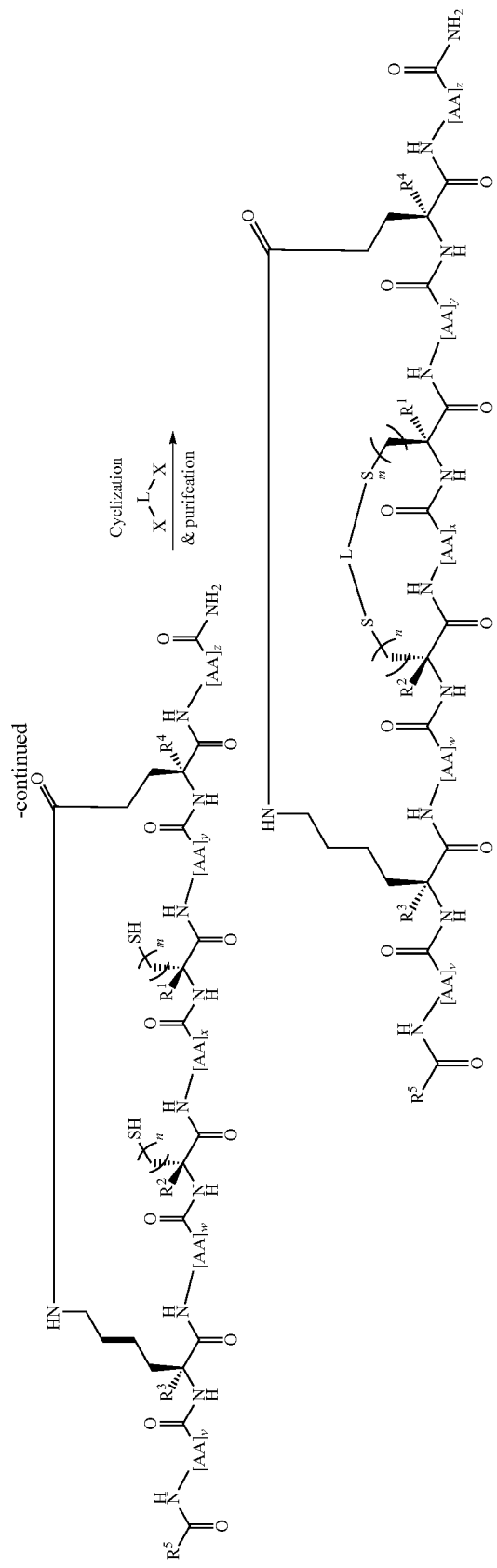

Solid Phase Synthesis of Peptides

Peptides were synthesized manually using standard solid phase synthesis using Fmoc/t-Bu chemistry as summarized above.

HATU with NMM were used as coupling agents to create the amide bond between the free amino terminus of the resin-bound protected peptide and the carboxylic acid of the Fmoc-protected amino acid.

The side chain protecting groups were: 2-Acetyl-5,5-dimethyl-1,3-cyclohexadion (Dde) for L-Lys; γ-Allylic (Allyl) for L-Glu and, 2,2,4,6,7-pentamethyldihydrobenzofuran-5-sulfonyl (Pbf) for L-Arg and D-Arg.

Fmoc-D-Arg(Pbf)-Sieber resin (0.30 mmol/g loading) was used for synthesis.

All the amino acids were dissolved at a 0.2 M concentration in anhydrous DMF.

Reactions were typically performed at the 0.3 mmol scale.

Every synthesis cycle included: (1) Fmoc amino acid deprotection: 20% Piperidine in DMF (20 mL) was added into the resin. The mixture was kept at room temperature for 30 min while a stream of nitrogen was bubbled through it. The mixture was filtered, and the peptidyl resin was washed with DMF (5×20 mL); (2) Coupling (potentially repeated twice for difficult couplings) with Fmoc protected amino acid/HATU/NMM (3, 2.85 and 6 equiv, respectively; room temperature; 1 h). Cycles of Fmoc deprotection and Fmoc-protected amino acid coupling were repeated with the desired monomers until the full linear peptide was formed. Final acylation (capping) step was performed using acetic anhydride capping solution [Capping Solution: Acetic anhydride (6 mL) and NMM (10 mL) in DMF (84 mL)].

Orthogonal Deprotections

Deprotection of the Glu Side Chain γ-Allyl Ester:

Tetrakis(triphenylphosphine)palladium(0) (1.5 equiv) and phenylsilane (15 equiv) were dissolved in DCM (6 mL). The solution was added to the peptidyl resin. The mixture was shaken for 1.5 h at room temperature and then washed with 2.5% sodium diethyldithiocarbamatre in DMF (6×15 mL).

Deprotection of the Lys side chain Dde: 3% hydrazine in DMF (20 mL) was added to the peptidyl resin. The mixture was kept at room temperature for 30 min while a stream of nitrogen was bubbled through it. The mixture was filtered, and the peptidyl resin was washed with DMF (5×20 mL). Then peptidyl resin was washed with MeOH (2×20 mL), DCM (2×20 mL) and MeOH (2×20 mL). The resin was dried under vacuum overnight.

Cleavage and Macrolactamization

The peptidyl resin (2.5 g) was cleaved with 2% TFA in DCM (40 mL) for 1 h at 40° C. pH was adjusted with DIPEA to ~9 and the solvent was removed under reduced pressure.

The residue was dissolved in DMF (150 mL). HOBt (18 equiv), DIPEA (6 equiv) and BOP (3 equiv) were added. The mixture was shaken for 3 h at room temperature. Upon completion (monitored by HLPC-MS), solvent was removed under reduced pressure.

Deprotection

TFA/$H_2O$ (95/5, v/v, 35 mL) and DTT (2 mmol) were added to the crude protected cyclic peptide. The mixture was shaken for 2.5 h at room temperature. Cold diethyl ether (270 mL) was added into the filtrate. The peptide was precipitated by centrifugation (4000 rpm). The precipitate was washed with diethyl ether (2×270 mL). The crude was dried under vacuum overnight to give the crude deprotected cyclic peptide as a solid.

Intermediate Purification

Purification was performed by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength λ=220 nm; gradient: 30% B over 60 min. UV absorbing fractions containing the target m/z ions were collected and the fractions containing product were confirmed by LC/MS.

Methylene Bridge Insertion

The intermediate peptide (0.04 mmol) was dissolved in a 1:1 mixture of water/ACN (19 mL). DODT (2 equiv) was added and the mixture was stirred at 30° C. for 30 min. pH was adjusted to ~8 by addition of 2.8 mL of aqueous 0.2 M ammonium carbonate solution. Diiodomethane (20 equiv) and DODT (2 equiv) were added. The mixture was shaken at 30° C. overnight.

Final HPLC Purification

The final crude peptide was purified by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength λ=220 nm; gradient: 30% B over 60 min. UV absorbing fractions containing the target m/z ions were collected and the fractions containing product were confirmed by LC/MS. Lyophilization of combined fractions containing pure peptide resulted in the final cyclized product as a powder.

6. Synthetic Procedure F

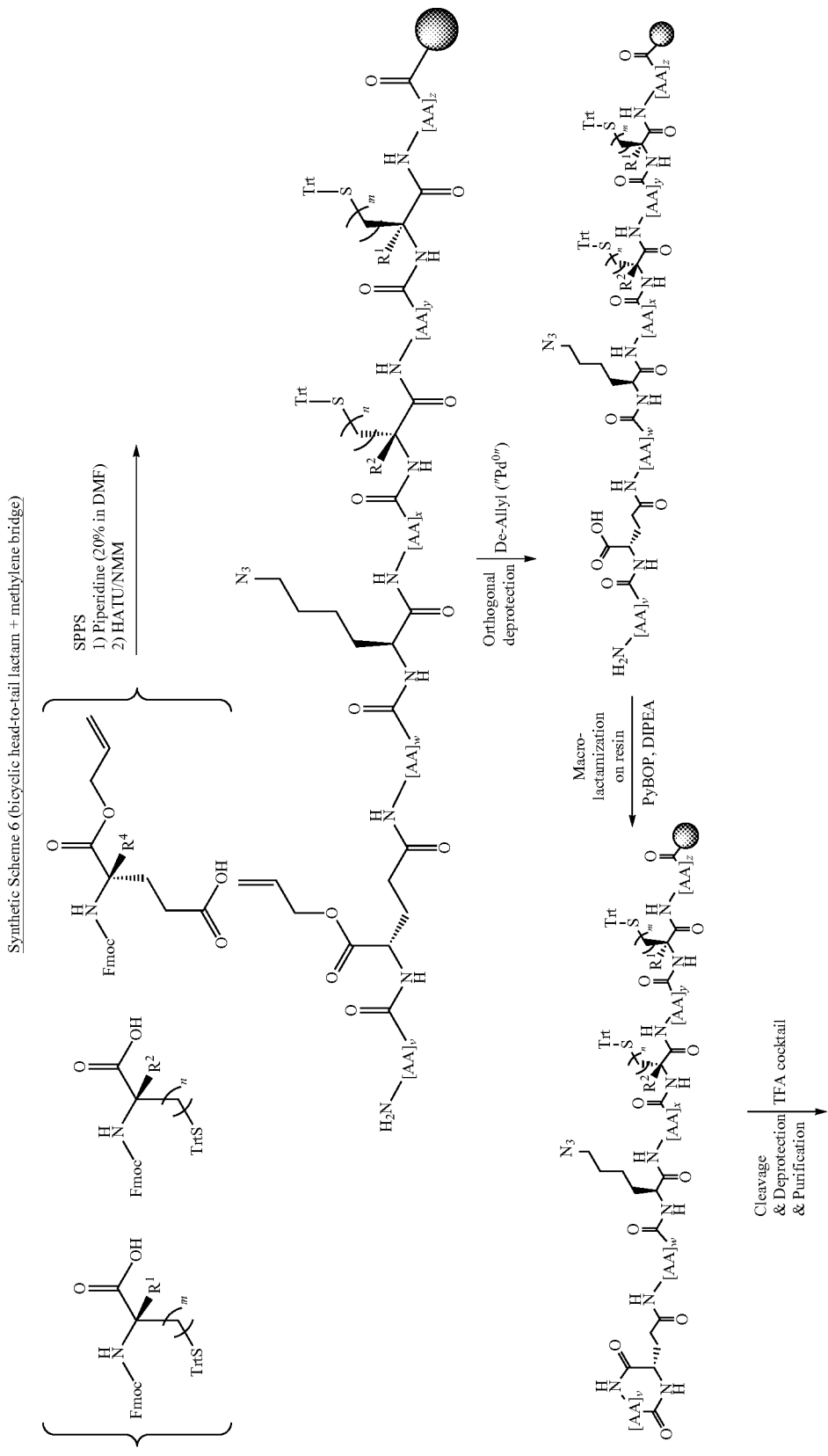

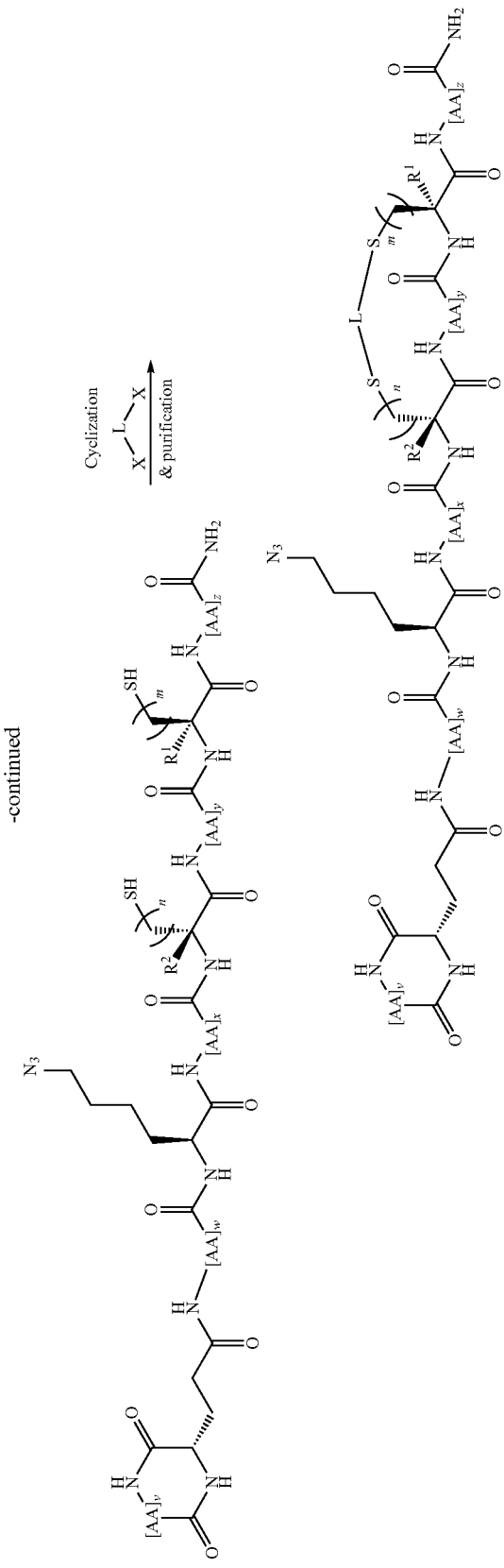

Solid Phase Synthesis of Peptides

Peptides were synthesized on a Symphony X Synthesizer using standard solid phase synthesis using Fmoc/t-Bu chemistry as summarized above.

HATU with NMM were used as coupling agents to create the amide bond between the free amino terminus of the resin-bound protected peptide and the carboxylic acid of the Fmoc-protected amino acid.

The side chain protecting groups were: α-Allylic (Allyl) for L-Glu and, 2,2,4,6,7-pentamethyldihydrobenzofuran-5-sulfonyl (Pbf) for L-Arg and D-Arg.

Unloaded Rink amide MBHA resin (100-200 mesh, 1% cross-linked polystyrene) was used for synthesis.

All the amino acids were dissolved at a 0.2 M concentration in anhydrous DMF.

Reactions were typically performed at the 0.3 mmol scale.

Every synthesis cycle included: (1) Fmoc amino acid deprotection: 20% piperidine in DMF (20 mL) was added into the resin. The mixture was kept at room temperature for 30 min while a stream of nitrogen was bubbled through it. The mixture was filtered, and the peptidyl resin was washed with DMF (5×20 mL); (2) Coupling (potentially repeated twice for difficult couplings) with Fmoc-protected amino acid/HATU/NMM (3, 2.85 and 6 equiv, respectively; room temperature; 1 h). Cycles of Fmoc deprotection and Fmoc-protected amino acid coupling were repeated with the desired monomers until the full linear peptide was formed. The final residue was Fmoc-deprotected and remained uncapped.

Orthogonal Deprotection (α-Allyl Ester)

Tetrakis(triphenylphosphine)palladium(0) (0.5 equiv) and 10% piperidine in THF (5 mL) were added to the peptidyl resin. The mixture was shaken for 4 h at room temperature. The solution was drained through the fit. The resin was washed with 5% (w/v) sodium diethyldithiocarbamate solution and then washed successively with DMF, MeOH, DCM and MeOH. The resin was dried under vacuum overnight.

Macrolactamization

The peptidyl resin was treated with PyBOP (6 equiv) and DIPEA (10 equiv) in DMF. The mixture was shaken for 16 h at room temperature. The solution was drained through the frit. The resin was washed successively with DMF, MeOH, DCM and MeOH.

Cleavage and Deprotection

The resin-bound peptide was deprotected and cleaved from the solid support by treatment with TFA/DTT/Thioanisole/Phenol/$H_2O$ (87.5/2.5/2.5/2.5/2.5, v/v) at room temperature for 3 h. After filtration of the resin, crude linear peptides were precipitated from the TFA cleavage solution using cold diethyl ether and collected by centrifugation (4000 rpm). The precipitate was washed with cold diethyl ether. The crude was dried under vacuum overnight to give the crude deprotected monocyclic peptide.

Intermediate Purification

The crude solids were redissolved in DMSO (1 mL) and was purified by Teledyne ISCO flash chromatography (15.5 g Redi Sep Rf Gold® Reversed-phase HP C18 Aq column) with gradient 20-60% ACN in water with 0.1% TFA as modifier (flowrate=30 mL/min). Fractions containing the desired product were collected and lyophilized to give the monocyclic product.

Methylene Bridge Insertion

The intermediate peptide was dissolved in a 1:1 mixture of water/ACN. Aqueous 0.2 M ammonium carbonate solution was added to adjust to pH~8. DODT (2 equiv) and diiodomethane (20 equiv) were added. Additional acetonitrile (2 mL) was added to make the reaction mixture homogeneous. The mixture was shaken at room temperature overnight.

Final HPLC Purification

Purification was performed by preparative reversed-phase high performance liquid chromatography (RP-HPLC) on Waters XSelect Peptide CSH C18 OBD Prep column (130 Å, 5 µm, column size 150×30 mm) using a Waters MS-Directed AutoPurification HPLC/MS system. Mobile phase: (A) 0.1% TFA in HPLC water and (B) 0.1% TFA in HPLC acetonitrile; flow rate: 50 mL/min; UV wavelength λ=214 nm; gradient: 26-31% B over 25 min. UV absorbing fractions containing the target m/z ions were collected and the fractions containing product were confirmed by LC/MS.

Purity of fractions was confirmed by UPLC, which was measured by a reverse phase Waters Acquity UPLC-MS system. Column: Waters XSelect CSH C18 XP Column (130 Å, 2.5 µm, column size 50×2.1 mm). Mobile phase: (A) 0.1% TFA in HPLC water and (B) 0.1% TFA in HPLC acetonitrile; gradient: 5-100% B in 14 min; injection volume: 0.5 µL; flow rate: 1 mL/min; UV wavelength λ=214 nm.

Lyophilization of combined fractions containing pure peptide resulted in the final cyclized product as a powder.

C. Synthesis of Specific Compounds

SEQ ID NO: 8

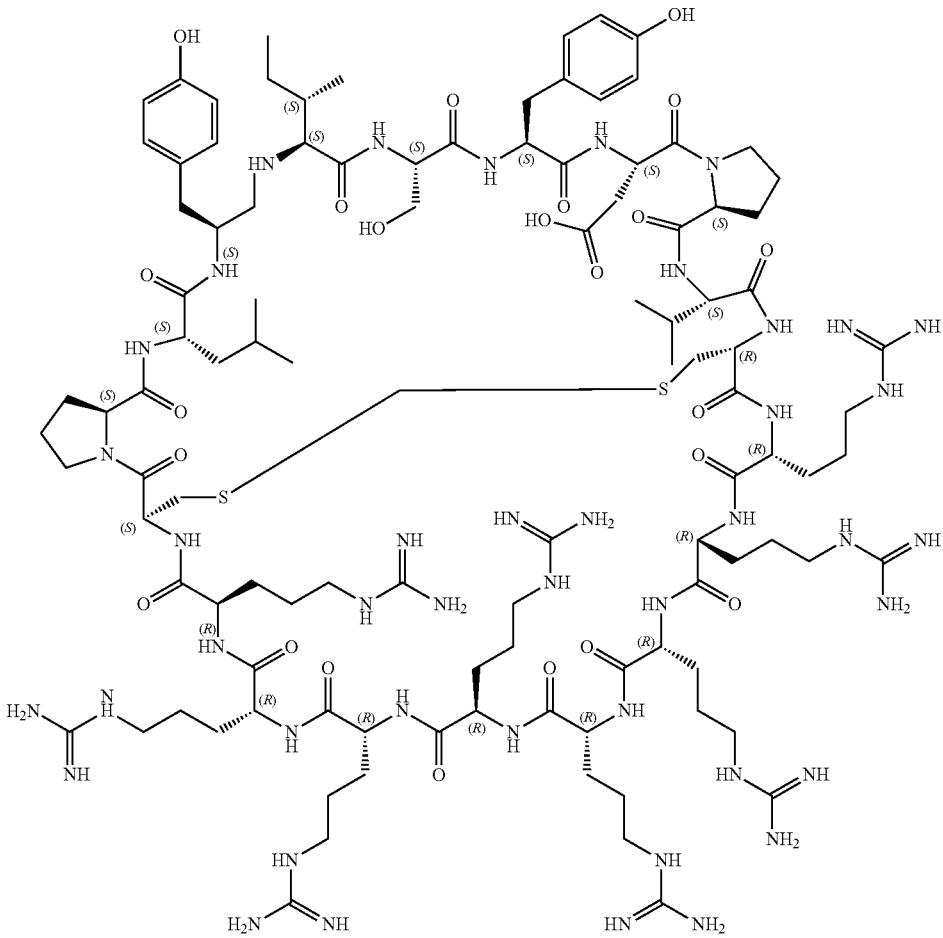

SEQ ID NO: 8 was synthesized using Synthetic Procedure D.

Intermediate Purification

Purification of the crude cyclic peptide (285 mg) was performed by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% H$_2$O; flow rate: 15 mL/min; UV wavelength λ=220 nm; gradient: 25-55% B over 60 min. UV absorbing fractions containing the target m/z ions were collected and the fractions containing product were confirmed by LC/MS.

Methylene Bridge Insertion

The intermediate cyclic peptide (65 mg, 0.026 mmol) was dissolved in a 1:1 mixture of water/ACN (13 mL). DODT (2 equiv) was added and the mixture was stirred at 30° C. for 30 min. pH was adjusted to ~8 by addition of aqueous 0.2 M ammonium carbonate solution. Diiodomethane (20 equiv) and DODT (2 equiv) were added. The mixture was shaken at 30° C. overnight.

Final HPLC Purification

The final crude peptide was purified by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% H$_2$O; flow rate: 15 mL/min; UV wavelength λ=220 nm; gradient: 22-52% B over 60 min. UV absorbing fractions containing the target m/z ions were collected and the fractions containing product were confirmed by LC/MS. Lyophilization of combined fractions containing pure peptide resulted in the final cyclized product (SEQ ID NO: 8) as a powder.

Purity of fractions was confirmed by UPLC, which was measured by a reverse phase Hewlett Packard 1100 UPLC-MS system. Column: Sepax GP-C18 Column (120 Å, 5 μm, column size 150×4.6 mm). Mobile phase: (A) 0.1% TFA in water and (B) 0.09% TFA in 80% ACN+20% H$_2$O; gradient: 27-37% B in 20 min; flow rate: 1 mL/min; UV wavelength λ=220 nm. The peptide was characterized by electrospray mass spectrometry on an Agilent 1260-6120 Quadrupole LC/MS (MW expected: 2516.0 Da; found MW: 839.4 ([M+3H]$^{3+}$).

SEQ ID NO: 57

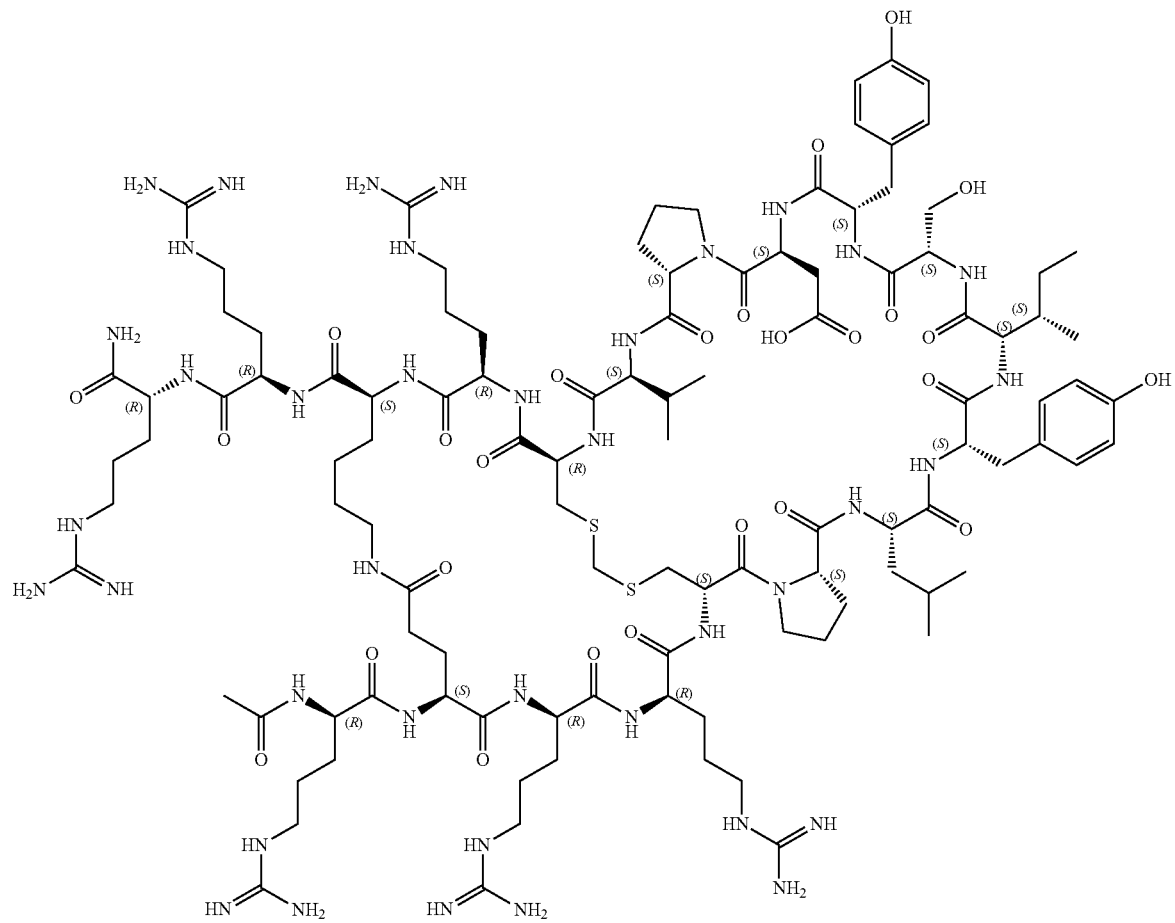

SEQ ID NO: 57 was synthesized using Synthetic Procedure E.

Macrolactamization

The peptidyl resin (2.5 g) was cleaved with 2% TFA in DCM (40 mL) for 1 h at 40° C. pH was adjusted with DIPEA to ~9 and the solvent was removed under reduced pressure. The residue was dissolved in DMF (150 mL). HOBt (18 equiv), DIPEA (6 equiv) and BOP (3 equiv) were added. The mixture was shaken for 3 h at room temperature. Upon completion (monitored by HLPC-MS), solvent was removed under reduced pressure.

Deprotection

TFA/H$_2$O (95/5, v/v, 35 mL) and DTT (2 mmol) were added to the crude protected cyclic peptide. The mixture was shaken for 2.5 h at room temperature. Cold diethyl ether (270 mL) was added into the filtrate. The peptide was precipitated by centrifugation (4000 rpm). The precipitate was washed with diethyl ether (2×270 mL). The crude was dried under vacuum overnight to give the crude deprotected cyclic peptide as a solid.

Intermediate Purification

Purification was performed by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% H$_2$O; flow rate: 15 mL/min; UV wavelength λ=220 nm; gradient: 22-52% B over 60 min. UV absorbing fractions containing the target m/z ions were collected and the fractions containing product were confirmed by LC/MS.

Methylene Bridge Insertion

The intermediate peptide (100 mg, 0.04 mmol) was dissolved in a 1:1 mixture of water/ACN (19 mL). DODT (2 equiv) was added and the mixture was stirred at 30° C. for 30 min. pH was adjusted to ~8 by addition of 2.8 mL of aqueous 0.2 M ammonium carbonate solution. Diiodomethane (20 equiv) and DODT (2 equiv) were added. The mixture was shaken at 30° C. overnight.

Final HPLC Purification

The final crude peptide was purified by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% H$_2$O; flow rate: 15 mL/min; UV wavelength λ=220 nm; gradient: 22 to 52% B over 60 min. UV absorbing fractions containing the target m/z ions were collected and the fractions containing product were confirmed by LC/MS. Lyophilization of combined fractions containing pure peptide resulted in the final cyclized product (SEQ ID NO: 57) as a white powder.

Purity of fractions was confirmed by UPLC, which was measured by a reverse phase Hewlett Packard 1100 UPLC-MS system. Column: Sepax GP-C18 Column (120 Å, 5 μm, column size 150×4.6 mm). Mobile phase: (A) 0.1% TFA in water and (B) 0.09% TFA in 80% ACN+20% H$_2$O; gradient: 27-37% B in 20 min; flow rate: 1 mL/min; UV wavelength λ=220 nm. The peptide was characterized by electrospray mass spectrometry on an Agilent 1260-6120 Quadrupole LC/MS (MW expected: 2501.9 Da; MW found: 834.7 ([M+3H]$^{3+}$).

g RediSep Rf Gold® Reversed-phase HP C18 Aq column) with gradient 20-60% ACN in water with 0.1% TFA as modifier (flowrate=30 mL/min). Fractions containing the desired product were collected and lyophilized to give the monocyclic product.

SEQ ID NO: 3

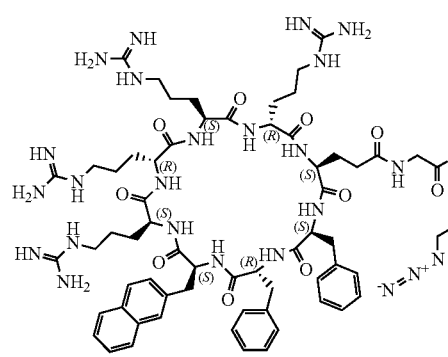
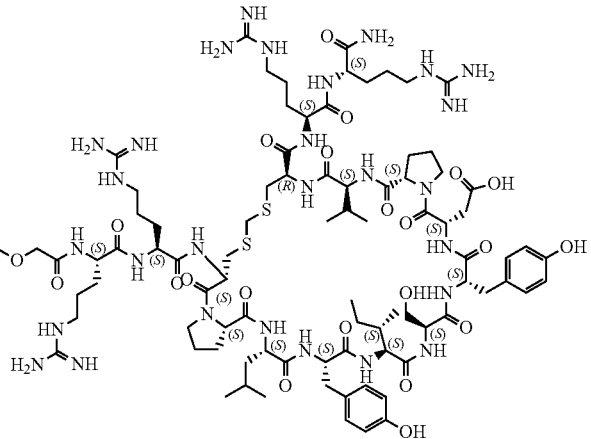

SEQ ID NO: 3 was synthesized using Synthetic Procedure F.

The protected linear peptide [H-Phe-DPhe-2Nal-Arg(Pbf)-DArg(Pbf)-Arg(Pbf)-DArg(Pbf)-γGlu(α-OAll)-Gly-Lys(N$_3$)-Aeea-Arg(Pbf)-Arg(Pbf)-DCys(Trt)-Pro-Leu-Tyr(OtBu)-Ile-Ser(OtBu)-Tyr(OtBu)-Asp(OtBu)-Pro-Val-Cys(Trt)-Arg(Pbf)-Arg(Pbf)-NH$_2$ (SEQ ID NO: 142) on Rink amide resin [where γGlu(α-OAll) is L-glutamic acid α-allyl ester and Aeea is 2-(2-(2-aminoethoxy)ethoxy)acetic acid)] was synthesized by solid phase peptide synthesis on a Rink Amide MBHA resin according to the general procedure F. There is no capping at N-terminus.

Orthogonal Deprotection (α-Allyl Ester)

To the reaction vessel containing the resin from the previous step was added Pd(PPh$_3$)$_4$ (30 mg, 0.25 equiv) and 10% piperidine in THF (5 mL). The mixture was shaken for 4 hours and the solution was drained through the frit. The resin was washed with 5% (w/v) sodium diethyldithiocarbamate solution and then washed successively with DMF (5×4 mL), DCM (5×4 mL) and DMF (2×4 mL).

Macrolactamization

To the reaction vessel containing the resin from the previous step was added PyBOP (312 mg, 6 equiv) and DIPEA (175 uL, 10 equiv) in DMF (6 mL). It was allowed to rotate for 16 h at room temperature, and then it was washed with DMF (5×4 mL) and DCM (5×4 mL).

Cleavage and Deprotection

The peptide was cleaved with a solution (TFA/DTT/Thioanisole/Phenol/H$_2$O=90/2.5/2.5/2.5/2.5, 8 mL) for 3 h at room temperature. After filtration of the resin, crude linear peptides were precipitated from the TFA cleavage solution using cold TBME (40 mL) and collected by centrifugation (4000 rpm). The crude peptide was washed with cold TBME (35 mL) and the residue was dissolved in acetonitrile/water (1:1, v/v, 15 mL) and lyophilized to dryness.

Intermediate Purification

The crude peptide was redissolved in DMSO (1 mL), and was purified by Teledyne ISCO flash chromatography (15.5

Methylene Bridge Insertion

The monocyclic peptide was dissolved in acetonitrile/water (1:1, v/v, 10 mL). NH$_4$HCO$_3$ (0.2 M solution in water) was added to adjust the pH to ~8. 3,6-Dioxa-1,8-octanedithiol (DODT, 2 equiv) and diiodomethane (20 equiv) were added. Additional acetonitrile (2 mL) was added to make the reaction mixture homogeneous. The resulting reaction mixture was stirred at room temperature overnight and monitored by LC-MS. After the reaction was complete, the reaction mixture was frozen and lyophilized.

Final HPLC Purification

Purification was performed by preparative reversed-phase high performance liquid chromatography (RP-HPLC) on Waters XSelect Peptide CSH C18 OBD Prep column (130 Å, 5 μm, column size 150×30 mm) using a Waters MS-Directed AutoPurification HPLC/MS system. Mobile phase: (A) 0.1% TFA in HPLC water and (B) 0.1% TFA in HPLC acetonitrile; flow rate: 50 mL/min; UV wavelength λ=214 nm; gradient: 26-31% B over 25 min. UV absorbing fractions containing the target m/z ions were collected and the fractions containing product were confirmed by LC/MS.

Purity of fractions was confirmed by UPLC, which was measured by a reverse phase Waters Acquity UPLC-MS system. Column: Waters XSelect CSH C18 XP Column (130 Å, 2.5 μm, column size 50×2.1 mm). Mobile phase: (A) 0.1% TFA in HPLC water and (B) 0.1% TFA in HPLC acetonitrile; gradient: 5-100% B in 14 min; injection volume: 0.5 μL; flow rate: 1 mL/min; UV wavelength λ=214 nm.

Lyophilization of combined fractions containing pure peptide resulted in the final bicyclized product (SEQ ID NO: 3) as a powder.

Reference Example—TR-FRET Tracer (SEQ ID NO: 68)

K-Ras(G12D) (GMPPNP) binding is measured by a TR-FRET competitive binding assay using a 5-FAM-labeled analog of KRpep-2d.

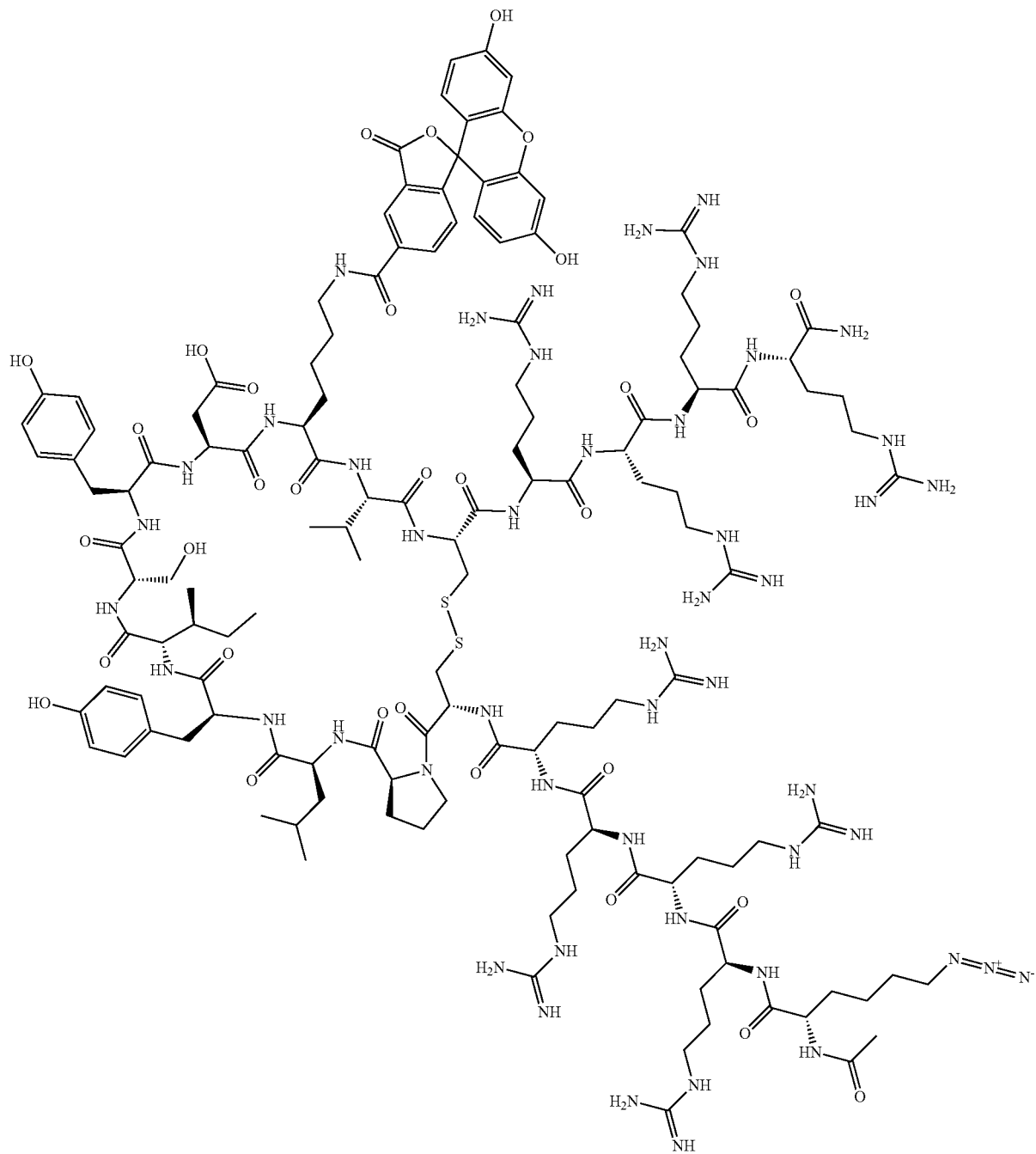 [SMILES: CC[C@H](C)[C@@H]1NC(=O)[C@H](Cc2ccc(O)cc2)NC(=O)[C@H](CC(C)C)NC(=O)[C@@H]2CCCN2C(=O)[C@@H](NC(=O)[C@H](CCCNC(=N)N)NC(=O)[C@H](CCCNC(=N)N)NC(=O)[C@H](CCCNC(=N)N)NC(=O)[C@H](CCCNC(=N)N)NC(=O)[C@H](CCCCN=[N+]=[N-])NC(C)=O)CSSC[C@@H](C(=O)N[C@@H](CCCNC(=N)N)C(=O)N[C@@H](CCCNC(=N)N)C(=O)N[C@@H](CCCNC(=N)N)C(=O)N[C@@H](CCCNC(=N)N)C(N)=O)NC(=O)[C@H](C(C)C)NC(=O)[C@H](CCCCNC(=O)c2ccc3c(c2)C(=O)OC32c3ccc(O)cc3Oc3cc(O)ccc32)NC(=O)[C@H](CC(=O)O)NC(=O)[C@H](Cc2ccc(O)cc2)NC(=O)[C@H](CO)NC1=O]

Solid Phase Synthesis of Peptides

The linear peptide was synthesized manually using standard solid phase synthesis using Fmoc/t-Bu chemistry as previously reported.

HATU with NMM were used as coupling agents to create the amide bond between the free amino terminus of the resin-bound protected peptide and the carboxylic acid of the Fmoc-protected amino acid.

The side chain protecting groups were: tert-butyl (tBu) for L-Asp, L-Ser and L-Tyr; trityl (Trt) for L-Cys; 4-Methyltrityl (Mtt) for L-Lys; 2,2,4,6,7-pentamethyldihydrobenzofuran-5-sulfonyl (Pbf) for L-Arg.

Knorr Amide MBHA Resin (0.27 mmol/g loading) was used for synthesis.

All the amino acids were dissolved at a 0.2 M concentration in anhydrous DMF.

The reaction was performed at the 0.2 mmol scale.

Every synthesis cycle includes: (1) Fmoc amino acid deprotection: 20% Piperidine in DMF (20 mL) was added into the resin. The mixture was kept at room temperature for 30 min while a stream of nitrogen was bubbled through it. The mixture was filtered, and the peptidyl resin was washed with DMF (5×20 mL); (2) Coupling (potentially repeated twice for difficult couplings) with Fmoc protected amino acid/HATU/NMM (3, 2.85 and 6 equiv, respectively; room temperature; 1 h). Cycles of Fmoc deprotection and Fmoc-protected amino acid coupling were repeated with the desired monomers until the full linear peptide was formed. Final acylation (capping) step was performed using acetic anhydride capping solution [Capping Solution: Acetic anhydride (6 mL) and NMM (10 mL) in DMF (84 mL)].

Cleavage

The linear resin-bound peptide (1.55 g of dry resin) was deprotected and cleaved from the solid support by treatment with TFA/EDT/Thioanisole/Phenol/$H_2O$ (87.5/2.5/5/2.5/2.5, v/v, 30 mL) at room temperature for 2.5 h. After filtration of the resin, the crude linear peptide was precipitated from the TFA cleavage solution using cold diethyl ether (150 mL) and collected by centrifugation (4000 rpm). The precipitate was washed with cold diethyl ether (2×150 mL). The crude material was dried under vacuum overnight to give the crude deprotected cyclic peptide as a solid (400 mg).

Linear Peptide Purification

Purification of the crude linear peptide was performed by preparative reversed-phase high performance liquid chromatography (RP-HPLC) on Phenomenex Luna C18(2) column (100 Å, 10 µm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength $\lambda$=220 nm; gradient: 20-50% B over 60 min. UV absorbing fractions containing the target m/z ions were collected and the fractions containing product were confirmed by LC/MS.

Disulfide Bond Formation

The linear peptide (0.05 mmol) was dissolved in a 1:1 mixture of water/ACN (20 mL). Acetic acid was added to the solution to adjust the pH to ~5. A solution of 0.1 M iodine in methanol was added dropwise at room temperature until color change (persistent yellow-orange color). After 5 min, an aqueous 0.1 M sodium thiosulfate solution was added dropwise to quench the excess of iodine.

Coupling of 5-Carboxyfluorescein ((5-FAM))

After oxidation, the crude cyclic peptide (22 mg, 0.008 mmol), 5-carboxyfluorescein (4 mg, 1.1 equiv) were dissolved in DMF (1 mL). HATU (16 mg, 5 equiv) and NMM (10 µL, 11 equiv) were added. The solution was shaken for 1 h at room temperature. Upon completion of the conjugation monitored by UPLC-MS, the 5-FAM-labeled peptide was purified by preparative reversed-phase high performance liquid chromatography (RP-HPLC) on Phenomenex Luna C18(2) column (100 Å, 10 µm, column size 200×21.2 mm using Waters 4000 system. Mobile phase: (A) 0.1% TFA in water and (B) 0.1% TFA in 80% ACN+20% $H_2O$; flow rate: 15 mL/min; UV wavelength $\lambda$=220 nm; gradient: 25-55% B over 60 min. UV absorbing fractions containing the target m/z ions were collected and the fractions containing product were confirmed by LC/MS. The solution was collected and lyophilized to give the final compound (SEQ ID NO: 68) as a solid 8.6 mg with the purity of 97.2%.

Purity of fractions was confirmed by UPLC, which was measured by a reverse phase Hewlett Packard 1100 UPLC-MS system. Column: Sepax GP-C18 Column (120 Å, 5 µm, column size 150×4.6 mm). Mobile phase: (A) 0.1% TFA in water and (B) 0.09% TFA in 80% ACN+20% $H_2O$; gradient: 32-42% B in 20 min; flow rate: 1 mL/min; UV wavelength $\lambda$=220 nm. The peptide was characterized by electrospray mass spectrometry on an Agilent 1260-6120 Quadrupole LC/MS (MW expected: 3104.5 Da; MW found: 622.0 ($[M+5H]^{5+}$).

Reference Example—TR-FRET Tracer (SEQ ID NO: 69)

K-Ras(G12D) (GDP) binding is measured by a TR-FRET competitive binding assay using a 5-FAM-labeled analog of thioacetal-bridged analog of KRpep-2d.

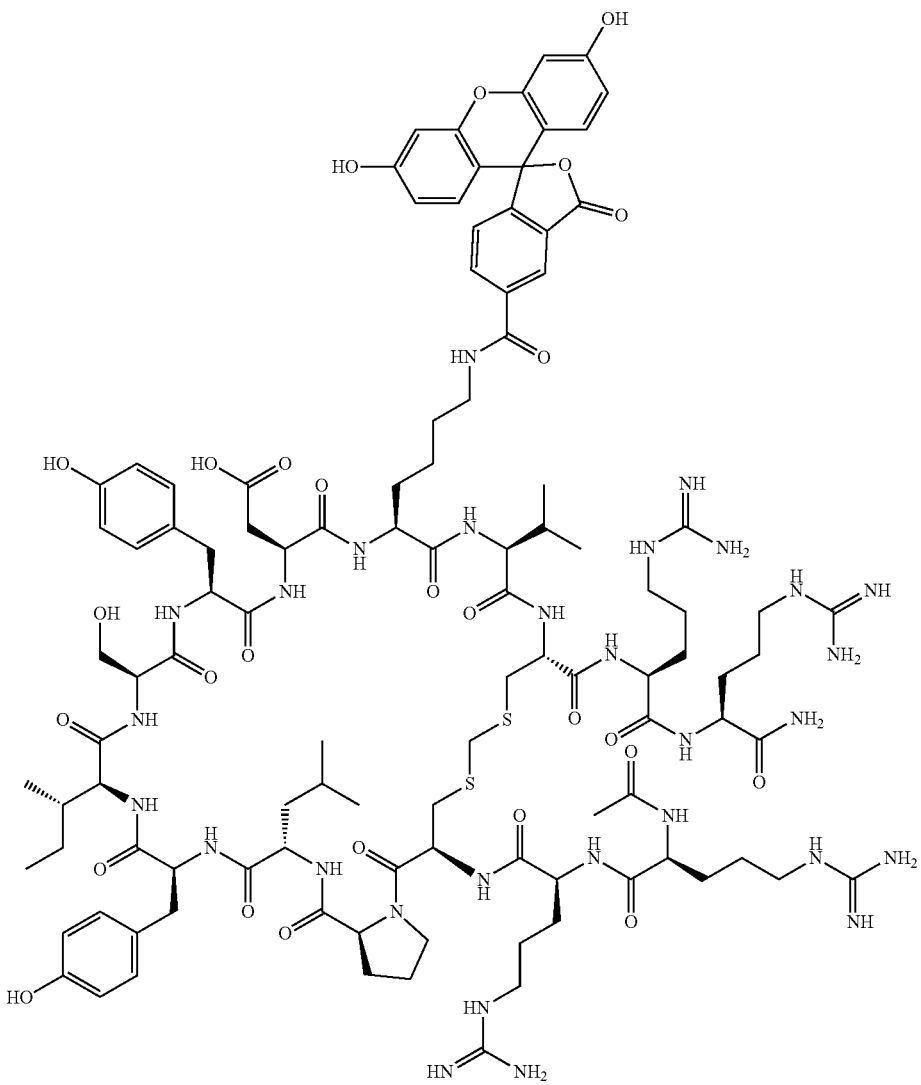 [SMILES: CC[C@H](C)[C@@H]1NC(=O)[C@H](Cc2ccc(O)cc2)NC(=O)[C@H](CC(C)C)NC(=O)[C@@H]2CCCN2C(=O)[C@H](NC(=O)[C@H](CCCNC(=N)N)NC(=O)[C@H](CCCNC(=N)N)NC(C)=O)CSCSC[C@@H](C(=O)N[C@@H](CCCNC(=N)N)C(=O)N[C@@H](CCCNC(=N)N)C(N)=O)NC(=O)[C@H](C(C)C)NC(=O)[C@H](CCCCNC(=O)c2ccc3c(c2)C(=O)OC32c3ccc(O)cc3Oc3cc(O)ccc32)NC(=O)[C@H](CC(=O)O)NC(=O)[C@H](Cc2ccc(O)cc2)NC(=O)[C@H](CO)NC1=O]

Solid Phase Synthesis of Peptides

Peptides were synthesized manually using standard solid phase synthesis using Fmoc/t-Bu chemistry as previously reported.

HATU with NMM were used as coupling agents to create the amide bond between the free amino terminus of the resin-bound protected peptide and the carboxylic acid of the Fmoc-protected amino acid.

The side chain protecting groups were: tert-butyl (tBu) for L-Asp, L-Ser and L-Tyr; trityl (Trt) for L-Cys and D-Cys; 1-(4,4-dimethyl-2,6-dioxocyclohex-1-ylidene)ethyl (Dde) for L-Lys; 2,2,4,6,7-pentamethyldihydrobenzofuran-5-sulfonyl (Pbf) for L-Arg.

Knorr Amide MBHA Resin (0.27 mmol/g loading) was used for synthesis.

All the amino acids were dissolved at a 0.2 M concentration in anhydrous DMF.

The reaction was performed at the 0.2 mmol scale.

Every synthesis cycle includes: (1) Fmoc amino acid deprotection: 20% piperidine in DMF (20 mL) was added into the resin. The mixture was kept at room temperature for 30 min while a stream of nitrogen was bubbled through it. The mixture was filtered, and the peptidyl resin was washed with DMF (5×20 mL); (2) Coupling (potentially repeated twice for difficult couplings) with Fmoc protected amino acid/HATU/NMM (3, 2.85 and 6 equiv, respectively; room temperature; 1 h). Cycles of Fmoc deprotection and Fmoc-protected amino acid coupling were repeated with the desired monomers until the full linear peptide was formed. Final acylation (capping) step was performed using acetic anhydride capping solution [Capping Solution: Acetic anhydride (6 mL) and NMM (10 mL) in DMF (84 mL)].

Orthogonal Deprotection

Deprotection of the Lys side chain Dde: 4% hydrazine hydrate in DMF (15 mL) was added to the peptidyl resin. The mixture was kept at room temperature for 30 min while a stream of nitrogen was bubbled through it. The mixture was filtered, and the peptidyl resin was washed with DMF (5×20 mL). Then peptidyl resin was washed with MeOH (2×20 mL), DCM (2×20 mL) and MeOH (2×20 mL). The resin was dried under vacuum.

Coupling of 5-Carboxyfluorescein ((5-FAM))

After selective deprotection of the Lys side chain, the peptidyl resin was treated with a mixture of 5-FAM (0.6 mmol, 3 equiv), HATU (0.57 mmol, 2.85 equiv) and NMM (1.2 mmol, 6 equiv) in DMF (2 mL). The suspension was shaken at room temperature for 1 h while a stream of nitrogen was bubbled through it. The peptidyl resin was washed with DMF (5×20 mL), MeOH (2×20 mL), DCM (2×20 mL) and MeOH (2×20 mL). The resin was dried under vacuum.

Cleavage

The resin-bound peptide was deprotected and cleaved from the solid support by treatment with TFA/EDT/Thioanisole/Phenol/H$_2$O (87.5/2.5/5/2.5, v/v, 34 mL) at room temperature for 2.5 h. After filtration of the resin, crude linear peptides were precipitated from the TFA cleavage solution using cold diethyl ether (150 mL) and collected by centrifugation (4000 rpm). The precipitate was washed with cold diethyl ether (2×170 mL). The crude was dried under vacuum overnight to give the crude deprotected cyclic peptide as a solid (475 mg).

Linear Peptide Purification

Purification of the crude linear SFAM-labeled peptide was performed by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% H$_2$O; flow rate: 15 mL/min; UV wavelength λ=220 nm; gradient: 27-57% B over 60 min. UV absorbing fractions containing the target m/z ions were collected and the fractions containing product were confirmed by LC/MS.

Methylene Bridge Insertion

The linear peptide (130 mg, 0.056 mmol) was dissolved in a 1:1 mixture of water/ACN (30 mL). DODT (0.112 mmol, 2 equiv) was added and the mixture was stirred at 30° C. for 30 min. pH was adjusted to ~8 by addition of 5.8 mL of aqueous 0.2 M ammonium carbonate solution. Diiodomethane (1.12 mmol, 20 equiv) and DODT (0.112 mmol, 2 equiv) were added. The mixture was shaken at 30° C. overnight.

Final Purification

The final crude 5-FAM-labeled peptide was purified by preparative reversed-phase high performance liquid chromatography (RP-HPLC) on Phenomenex Luna C18(2) column (100 Å, 10 μm, column size 200×21.2 mm using Waters 4000 system. Mobile phase: (A) 0.1% TFA in water and (B) 0.1% TFA in 80% ACN+20% H$_2$O; flow rate: 15 mL/min; UV wavelength λ=220 nm; gradient: 22-52% B over 60 min. UV absorbing fractions containing the target m/z ions were collected and the fractions containing product were confirmed by LC/MS. The solution was collected and lyophilized to give the final compound (SEQ ID NO: 69) as a solid 11.0 mg with the purity of 95.3%.

Purity of fractions was confirmed by UPLC, which was measured by a reverse phase Hewlett Packard 1100 UPLC-MS system. Column: Sepax GP-C18 Column (120 Å, 5 μm, column size 150×4.6 mm). Mobile phase: (A) 0.1% TFA in water and (B) 0.09% TFA in 80% ACN+20% H$_2$O; gradient: 32-42% B in 20 min; flow rate: 1 mL/min; UV wavelength λ=220 nm. The peptide was characterized by electrospray mass spectrometry on an Agilent 1260-6120 Quadrupole LC/MS (MW expected: 2339.7 Da; MW found: 585.8 ([M+4H]$^{4+}$).

Biological Assays:

Sequence for K-Ras Construct

For K-Ras, the construct was full-length and derived from UniProt reference P01116-2 (K-Ras4B isoform) RASK_HUMAN Isoform 2B of GTPase K-Ras, Homo sapiens having a G12D mutation (VAR_016026). It comprised the following sequence:

(SEQ ID NO: 143)
GGGGMTEYKLVVVGADGVGKSALTIQLIQNHFVDEYDPTIEDSYRKQVV

IDGETCLLDILDTAGQEEYSAMRDQYMRTGEGFLCVFAINNTKSFEDIH

HYREQIKRVKDSEDVPMVLVGNKCDLPSRTVDTKQAQDLARSYGIPFIE

TSAKTRQGVDDAFYTLVREIRKHKEK

Protein Production Protocol

Expression and purification of GDP and GMPPNP-loaded K-Ras(G12D) were carried out. His-SUMO-tagged human K-Ras resides 1-169 was expressed in E. coli Rosetta 2 (DE3). Protein expression was induced by 1 mM IPTG overnight at 18° C. Cells were lysed in 40 mM Tris pH 7.8, 150 mM NaCl, 0.5% Triton x-100, 5 mM BME, 10 mM imidazole, protease inhibitors EDTA-free tablets (⅕₀ mL). Clarified lysate was loaded on Ni-NTA FF prepacked columns (Qiagen) and washed with 10 column volumes (CV) of wash buffer (40 mM Tris pH 7.8, 150 mM NaCl, 5 mM BME, 10 mM imidazole). Protein was eluted by buffer containing 40 mM Tris pH 7.8, 150 mM NaCl, 5 mM BME, 300 mM imidazole. The resulting protein was tag removed by SUMO protease in dialysis buffer (40 mM Tris pH 7.8, 150 mM NaCl, 1 mM DTT, 10 mM Imidazole) overnight at 4° C., followed by subtractive Ni-NTA purification to remove the tagged protein. K-Ras protein was N-terminally biotinylated using SrtA and biotin-Sortag peptide [biotin-KGGGLPETGG-OH] (SEQ ID NO: 144). The reaction was carried out at room temperature for 5 h, followed by Ni subtraction to remove His-tagged SrtA and SoftLink™ Avidin Resin purification to isolate the biotin-labeled K-Ras.

Procedure for GDP Nucleotide Loading

K-Ras(G12D) protein was treated with 5 mM EDTA and 5 mM GDP for a minimum of 2 h on ice. The reaction was stopped by addition of 40 mM MgCl$_2$ and incubate on ice for 1 h. The reaction was stopped by addition of 40 mM MgCl$_2$ and incubate on ice for 1 h. The resulting proteins were further purified and buffer-exchanged on a Superdex 75 26/60 size exclusion column preequilibrated in 25 mM HEPES pH 7.5, 150 mM NaCl, 2 MgCl$_2$, 2 mM TCEP. The nucleotide loading efficiency was analyzed by HPLC. Specifically, 5 μL of the protein or nucleotide at 100 μM were injected on a RP-C18 analytical column. Nucleotides were separated through an isocratic elution in 100 mM potassium phosphate, pH 6.5, 10 mM tetrabutylammonium bromide, 0.2 mM NaN$_3$, and 3% acetonitrile. The runs are monitored at 254 nm and compared to GDP standard.

Procedure for GMPPNP Nucleotide Loading

K-Ras(G12D) protein was treated with 5 mM EDTA and 5 mM GMPPNP for 1 h on ice, followed by adding 25-50 U of CIAP agarose and incubating a minimum of 2 h at 4° C. on a wheel. CIAP agarose was removed by centrifuge. The reaction was stopped by addition of 40 mM MgCl$_2$ and incubated on ice for 1 h. The resulting proteins were further purified and buffer-exchanged on a Superdex 75 26/60 size exclusion column preequilibrated in 25 mM HEPES pH 7.5, 150 mM NaCl, 2 MgCl$_2$, 2 mM TCEP. The nucleotide loading efficiency was analyzed by HPLC. Specifically, 5 μL of the protein or nucleotide at 100 μM were injected on a RP-C18 analytical column. Nucleotides were separated through an isocratic elution in 100 mM potassium phosphate, pH 6.5, 10 mM tetrabutylammonium bromide, 0.2 mM NaN$_3$, and 3% acetonitrile. The runs are monitored at 254 nm and compared to GMPPNP standard.

Procedure for Time-Resolved Fluorescence/Forster Resonance Energy Transfer (TR-FRET) Assay Using K-Ras (G12D) Loaded with GMPPNP Macrocyclic peptide binding affinities to K-Ras(G12D) (GMPPNP) were characterized using a TR-FRET-based competitive binding assay. A master mixture of 30 nM K-Ras(G12D) (GMPPNP), 5 nM Terbium-Streptavidin (ThermoFisher Scientific PV3996) and 200 nM fluorescently-labeled tracer (SEQ ID NO: 68) was prepared. 10 µL of the master mixture was added to each well of the 384-well, flat bottom, non-binding, black microplate (Greiner 784900) for the respective assay. Compound dose-response titrations were prepared, and appropriate amounts of compounds were dispensed, using Echo 550 liquid handler, into the respective 384-well black microplate, containing the master mixture. The assay plate is sealed with an aluminum foil and placed on a shaker at ambient temperature for 5 min. The plate was then centrifuged at 1000 g for 3 min, then incubated in the dark for 1 h at ambient temperature. Assay plates were read at ambient temperature on the Tecan M1000, with excitation at 340 nm and emission at 495 nm. Dose response curves and $EC_{50}$ were analyzed using a 4-parameter logistic equation in GraphPad Prism software (GraphPad, San Diego, CA). The results are shown in FIG. 2A to FIG. 2D.

Procedure for Time-Resolved Fluorescence/Forster Resonance Energy Transfer (TR-FRET) Assay Using K-Ras (G12D) Loaded with GDP Macrocyclic peptide binding affinities to K-Ras(G12D) (GDP) were characterized using a TR-FRET-based competitive binding assay. A master mixture of 30 nM K-Ras(G12D) (GDP), 5 nM Terbium-Streptavidin and 500 nM fluorescently-labeled tracer (SEQ ID NO: 69) was prepared. 10 µL of the master mixture was added to each well of the 384-well, flat bottom, non-binding, black microplate (Greiner 784900) for the respective assay. Compound dose-response titrations were prepared, and appropriate amounts of compounds were dispensed, using Echo 550 liquid handler, into the respective 384-well black microplate, containing the master mixture. The assay plate is sealed with an aluminum foil and placed on a shaker at ambient temperature for 5 min. The plate was then centrifuged at 1000 g for 3 min, then incubated in the dark for 18 h at ambient temperature. Assay plates were read at ambient temperature on the Tecan M1000, with excitation at 340 nm and emission at 495 nm. Dose response curves and EC50 were analyzed using a 4-parameter logistic equation in GraphPad Prism software (GraphPad, San Diego, CA). The results are shown in FIG. 2A to FIG. 2D.

Procedure for Cellular Phospho-ERK Assay in AsPC-1 Cells (Primary Screen)

The cellular K-Ras inhibitory activity was evaluated by phosphorylation levels of ERK1/2 in AsPC-1 (homozygous K-Ras(G12D)) cells. AsPC-1 cells (ATCC® CRL-1682™) were cultured in T175 flask in growth medium (RPMI 1640 Medium, GlutaMAX™ Supplement, HEPES (Gibco 72400-047) supplemented with 10% fetal bovine serum (Hyclone SH30071.03) and 1× Penicillin/Streptomycin (Gibco 15140-122). The cells were harvested in seeding medium (RPMI 1640 Medium, no phenol red (Gibco 11835-030) supplemented with 10% fetal bovine serum (Hyclone SH30071.03), 25 mM HEPES (Gibco 15630-080) and 1× Penicillin/Streptomycin (Gibco 15140-122) after 5 min of 0.25% Trypsin-EDTA (Gibco 25200-056) digestion and were seeded in 384-well tissue culture treated plate (Greiner 781091) at a density of 15,000 cells/25 µL/well, and incubated at 37° C., 5% $CO_2$ overnight. Prior to dosing, seeding medium was removed using the BlueCatBio Bluewasher system and replaced with 20 µL of assay medium (RPMI 1640 Medium, no phenol red (Gibco 11835-030) supplemented with 25 mM HEPES (Gibco 15630-080) and 1× Penicillin/Streptomycin (Gibco 15140-122). The compound dose-response titrations were prepared, and appropriate amounts of compounds were dispensed into the 384-well cell culture assay plate using the Echo 550 liquid handler. 25 assay medium was added to achieve a final assay volume of 45 µL. Assay plate was incubated at 37° C., 5% $CO_2$ for 1 h and 18 h. At 1 h and 18 h post dose, 25 µL assay medium was removed and transferred to an empty 384-well tissue culture treated plate (Greiner 781091) for the LDH membrane integrity assay. Remaining assay medium was removed from the plate, and cells were washed once with 254, 1×DPBS (Gibco 14190-144). Cells were lysed in 20 µL 1×lysis buffer from Alpha SureFire® Ultra™ Multiplex pERK and total ERK assay kit (PerkinElmer MPSU-PIERK) containing EDTA-free Protease inhibitor cocktail (Roche 11836170001) at ambient temperature with constant shaking at 300 rpm for 10-15 min. The cell lysates were mixed for 10 cycles using the Agilent Bravo 384ST liquid handler system before 10 µL was transferred to OptiPlate-384 plate (PerkinElmer 6007680). Phosphorylated ERK and total ERK levels were detected by Alpha SureFire Ultra Multiplex pERK kit (PerkinElmer MPSU-PTERK) using 5 acceptor bead mix and 5 µL donor bead mix, both prepared following the manufacturer's protocol. Plates were sealed using aluminum sealing tape (Costar 07-200-683) during incubation at ambient temperature with constant shaking at 300 rpm for 1 h (both acceptor and donor). Assay plates were read on a Envision Xcite Multilabel Reader (PerkinElmer 1040900) at ambient temperature, with emission at 535 nm (Total ERK) and emission at 615 nm (Phospho ERK). Ratio of pERK vs total ERK in each well was used as the final readout. Dose response curves and $EC_{50}$ were analyzed using a 4-parameter logistic equation in GraphPad Prism software (GraphPad, San Diego, CA). The results are shown in FIG. 2A to FIG. 2D.

Procedure for CytoTox-ONE™ Homogeneous Membrane Integrity (LDH) Assay

Cellular damages were measured by LDH release assay. At 1 and 18 h post dose, 25 assay medium was removed from the primary cell culture assay plate and transferred to an empty 384-well tissue culture treated plate (Greiner 781091) using the Agilent Bravo 384ST liquid handler system. CytoTox-ONE reaction mix was prepared from the CytoTox-ONE™Homogeneous Membrane Integrity Assay Kit (Promega G7891) according to manufacturer's protocol. 25 µL of CytoTox-ONE reaction mix was added to the assay plate containing 25 assay medium, and plate was sealed using aluminum sealing tape (Costar 07-200-683). Assay plate was incubated at ambient temperature with constant shaking at 300 rpm for 45 min. Assay plates were read at ambient temperature on the Tecan M1000, with excitation at 560 nm and emission at 590 nm. Dose response curves and $EC_{50}$ were analyzed using a 4-parameter logistic equation in GraphPad Prism software (GraphPad, San Diego, CA). The results are shown in FIG. 2A to FIG. 2D.

Procedure for Peptide Permeability (NanoClick) Assay

The optimization of therapeutic peptides for intracellular targets requires a comprehensive assessment of affinity, metabolic stability, cell penetration and cytosolic delivery. This assessment benefits from a high-throughput and quantitative cell penetration assay. The Applicants developed a copper-free strain-promoted azide-alkyne cycloaddition (SPAAC)-based assay to directly quantify in cells uptake and cytosolic penetration of peptides and macrocycles.

The NanoClick assay relies on the addition of a small azido tag on the peptide or macrocycle of interest, typically at the N-terminus such that the tag (an L-azido-lysine) has a negligible effect on binding affinity or stability and minimal influence on permeability and cellular activity. The amount of azido-labeled permeable peptide is measured by its ability to compete with cell-permeable azido-labeled dye (NanoBret 618 Azide-$C_3$ from Promega). The output is measured using BRET (Bioluminescence Resonance Energy Transfer) with a *Renilla* luciferase-HaloTag construct modified with a DiBac-Chloroalkane handle as the donor and NanoBRET™ 618 as the acceptor.

The NanoClick measures the cell penetration of macrocyclic peptides and the inclusion of the azido-labeled amino acid residue has a minimal effect on the properties of the peptide under study.

Assay ready frozen Hela cells transient transfected with NanoLuc-HaloTag expressing construct were suspended in growth media consisting of MEM media (Gibco), 10% heat inactivated FBS (Gibco), 1×NEAA (Gibco), 1× Sodium Pyruvate (Gibco), 1× GlutaMax (Gibco), 1× PenStrep (Gibco). Cells were seeded in the growth media at 6000 cells/well and incubated in 37° C. 5% $CO_2$ overnight. DiBac-Chloroalkane (DiBac-CA) (Promega) was diluted in the assay buffer consisting of Opti-mem without phenol red (Gibco) and 1% FBS and added to the cell at a final concentration of 3 µM. The cells were incubated with Dibac-CA for 1 h at 37° C., then washed twice with HBSS with $Ca^{2+}$ $Mg^{2+}$ (Hyclone) and replaced with 30 µL of assay buffer. Peptides were dissolved in 100% DMSO and serially diluted to generate a 10-point titration and transferred into the 384-well assay plates (300 nl/well) containing the transfected Hela cells and incubated for 4 h and 18 h (overnight) in 37° C. NanoBret 618 Azide-C3 (Promega) was diluted into assay buffer and added to cells at a final concentration of 10 µM and µincubated at 37° C. for 1 h. NanoBRET™ Nano-Glo® Substrate (500×)/extracellular NanoLuc®

Inhibitor (30 mM) was diluted into assay buffer and added to cells at a final concentration of 1× substrate and 20 µM of Inhibitor. NanoBret signal with donor emission (e.g., 450 nm) and acceptor emission (e.g., 610 nm) was measured using an EnVision Multilabel plate reader (Perkin Elmer). A raw Bret ratio was generated by dividing the acceptor emission value (610 nm) by the donor emission value (450 nm) for each sample. EC50 values were calculated using a 4 parameter logistic fit. Stapled peptide ATSP-7041 (Chang, Y. S.; Graves, B.; Guerlavais, V.; Tovar, C.; Packman, K.; To, K.-H.; Olson, K. A.; Kesavan, K.; Gangurde, P.; Mukherjee, A.; Baker, T.; Darlak, K.; Elkin, C.; Filipovic, Z.; Qureshi, F. Z.; Cai, H.; Berry, P.; Feyfant, E.; Shi, X. E.; Horstick, J.; Annis, D. A.; Manning, A. M.; Fotouhi, N.; Nash, H.; Vassilev, L. T.; Sawyer, T. K. *Proc. Natl. Acad. Sci. USA* 2013, 110, E3445) modified with an azido-lysine at the N-terminus (Sequence=Ac-Lys($N_3$)-Bala-Leu-Thr-Phe-cyclo(R8-Glu-Tyr-Trp-Ala-Gln-Cba-55)-Ser-Ala-Ala-$NH_2$ (SEQ ID NO: 145)) was used as control for permeable peptide. Stapled peptide PM2/sMTide-02 (Brown, C. J.; Quah, S. T.; Jong, J.; Goh, A. M.; Chiam, P. C.; Khoo, K. H.; Choong, M. L.; Lee, M. A.; Yurlova, L.; Zolghadr, K.; Joseph, T. L.; Verma, C. S.; Lane, D. P. *ACS Chem. Biol.* 2013, 8, 506) modified at the N-terminus by addition of an azido-lysine and three glutamic acid residues and at the C-terminus by addition of two glutamic acid residues (Sequence=H-Glu-Glu-Glu-Lys($N_3$)-Ser-Gly-Ser-Thr-Ser-Phe-cyclo(R8-Glu-Tyr-Trp-Ala-Leu-Leu-S5)-Glu-Glu-Glu-$NH_2$ (SEQ ID NO: 146) was used as control for impermeable peptide.

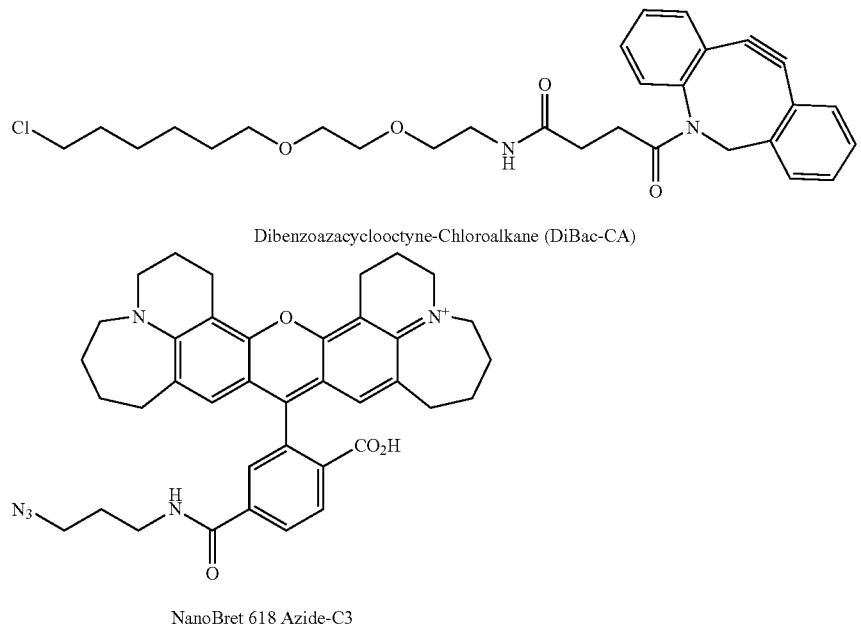

Dibenzoazacyclooctyne-Chloroalkane (DiBac-CA)

NanoBret 618 Azide-C3

The results are shown in FIG. 2A to FIG. 2D.

Procedure for Cell Homogenate Stability Assay

Stability of peptides towards intracellular proteases can be evaluated using HeLa cell homogenate. Suspended HeLa cells at 1 million cells/mL are sonicated in bursts with a probe sonicator on ice until uniformly homogenized. The homogenate thus prepared is frozen and stored at −20° C. until use. The peptides are incubated with the homogenate at 1 million cells/mL and loss of the peptide with increasing time is quantified using LC-MS/MS. Briefly, the test peptide is incubated with the homogenate at 1 µM in final volume of 50 µL at 37° C. At 0, 10, 30, 60 and 120 min, the reactions are quenched with 150 µL solution of 80% (v/v) Acetonitrile in Methanol containing a known internal standard peptide. The quenched samples are centrifuged at 4000 rpm for 5 min at 10° C. and supernatants are injected for bioanalysis by liquid chromatography combined with tandem-mass spectrometer. O-Neg (Cruz, J.; Mihailescu, M.; Wiedman, G.; Herman, K.; Searson, P. C.; Wimley, W. C.; Hristova, K. Biophysical J. 2013, 104, 2419) is used as a positive control and ATSP-7041 (Chang, Y. S.; Graves, B.; Guerlavais, V.; Tovar, C.; Packman, K.; To, K.-H.; Olson, K. A.; Kesavan, K.; Gangurde, P.; Mukherjee, A.; Baker, T.; Darlak, K.; Elkin, C.; Filipovic, Z.; Qureshi, F. Z.; Cai, H.; Berry, P.; Feyfant, E.; Shi, X. E.; Horstick, J.; Annis, D. A.; Manning, A. M.; Fotouhi, N.; Nash, H.; Vassilev, L. T.; Sawyer, T. K. Proc. Natl. Acad. Sci. USA 2013, 110, E3445) is used as a negative control. In addition, pre-boiled homogenate (prepared by incubating homogenate for 30 min in boiling water) is also used as a negative control for each test peptide. The $k_e$ is first-order rate constant describing the disappearance of parent drug in the incubation and may be obtained from regressing the initial slope (ke=−(slope)) of the natural log of the analyte area/internal standard area (designated as C at an appointed time t) in C versus time (min) profile. The half-life (t½) is calculated as:

$$t1/2 = \frac{0.693}{ke}$$

The results are shown in FIG. 2A to FIG. 2D.

The invention claimed is:
1. A compound of Formula (I)

[Chemical structure of Formula (I)]

wherein:
$R^{6a}$ and $R^{6b}$ are independently H, $C_1$-$C_3$ alkyl, fluoro, —$NH_2$, azido, hydroxy, $C_3$-$C_6$ cycloalkyl, phenyl, or —$OR^{6c}$, wherein $R^{6c}$ is allyl, propargyl, or benzyl;
or $R^{6a}$ and $R^{6b}$, together with the carbon atoms to which they are attached, form a 3- to 6-membered cycloalkyl ring which is unsubstituted or substituted by 1 to 3 $C_1$-$C_3$ alkyl;
$R^7$ is $C_1$-$C_7$ alkyl or —$C_3$-$C_6$ cycloalkyl;
$R^8$ is $C_6$-$C_{10}$ aryl or indolyl, wherein said $C_6$-$C_{10}$ aryl or indolyl of $R^8$ is optionally (i) substituted by one $C_1$-$C_6$ alkyl, $C_1$-$C_6$ fluoroalkyl, hydroxy, $C_1$-$C_6$ alkoxy, $C_1$-$C_6$ fluoroalkoxy, phenyl, or benzyloxy and (ii) optionally substituted by 1 to 5 halogens;
$R^{10a}$ is -$CH_2OH$, $C_1$-$C_8$ alkyl, $C_3$-$C_6$ cycloalkyl, or —$CH_2$—$R^{10c}$, wherein $R^{10c}$ is $C_6$-$C_{10}$ heteroaryl or $C_3$-$C_6$ cycloalkyl;
$R^{10b}$ is H or $C_1$-$C_4$ alkyl;
or $R^{10a}$ and $R^{10b}$ together with the carbon atom to which they are attached form a 3- to 6-membered cycloalkyl ring, wherein said 3- to 6-membered cycloalkyl is optionally fused to phenyl;
$R^{11a}$ and $R^{11b}$ are independently H, $C_3$-$C_6$ cycloalkyl, $C_6$-$C_{10}$ aryl, or 5- to 9-membered heteroaryl, wherein said $C_6$-$C_{10}$ aryl or 5- to 9-membered heteroaryl of $R^{11a}$ or $R^{11b}$ is optionally substituted by (i) 1 hydroxy, $C_1$-$C_6$ alkyl, $C_1$-$C_6$ fluoroalkyl, or $C_1$-$C_6$ fluoroalkoxy and (ii) 1 to 5 halogens;
$R^{14}$ is $C_1$-$C_6$ alkyl, —$CH_2CH_2CO_2H$, —$C_3$-$C_6$ cycloalkyl, or —$CH_2$—$R^{14a}$, wherein $R^{14a}$ is $C_3$-$C_6$ cycloalkyl;
$R^{15a}$ and $R^{15b}$ are independently H or $C_1$-$C_3$ alkyl;
X is methylene;
$R^0$ is:
  (i) H,
  (ii) Ac-Lys ($N_3$),
  (iii) $R^{0a}C(O)$— wherein $R^{0a}$ is $C_1$-$C_6$ alkyl or $C_3$-$C_6$ cycloalkyl;
  (iv) a Cell-Penetrating Peptide (CPP) moiety; or
  (v) a group of the formula:

[Chemical structure]

$R^{20}$ is:
  (i) —OH;
  (ii) $OR^{20a}$, wherein $R^{20a}$ is $C_1$-$C_6$ alkyl;
  (iii) -$NH_2$;
  (iv) —N(H) $R^{20a}$;
  (v) —N($R^{20a}$)($R^{20b}$), wherein $R^{20b}$ is $C_1$-$C_6$ alkyl, or alternatively, $R^{20a}$ and $R^{20b}$ together with the nitrogen atom to which they are attached form a 3- to 6-membered heterocycloalkyl ring or
  (vi) a CPP moiety;
or alternatively, $R^0$ and $R^{20}$ join to form a second ring via an amide linkage;
the moiety —$X_1$—$X_2$—$X_3$—$X_4$— is (D-Arg)$_4$; and
the moiety —$X_{16}$—$X_{17}$—$X_{18}$—$X_{19}$— is (D-Arg)$_4$;
or a pharmaceutically acceptable salt thereof.

2. The compound of claim 1 or a pharmaceutically acceptable salt thereof, wherein $R^0$ is acetyl.

3. The compound of claim 1 or a pharmaceutically acceptable salt thereof, wherein $R^{20}$ is —$NH_2$.

4. The compound of claim 1 or a pharmaceutically acceptable salt thereof, wherein $R^{6a}$ and $R^{6b}$ are both H.

5. The compound of claim 1 or a pharmaceutically acceptable salt thereof, wherein $R^7$ is —$C(H)(CH_3)_2$.

6. The compound of claim 1 or a pharmaceutically acceptable salt thereof, wherein $R^8$ is 4-hydroxyphenyl.

7. The compound of claim 1 or a pharmaceutically acceptable salt thereof, wherein $R^{10a}$ is —$CH_2OH$ and $R^{10b}$ is H.

8. The compound of claim 1 or a pharmaceutically acceptable salt thereof, wherein $R^{11a}$ is 4-hydroxyphenyl and $R^{11b}$ is H.

9. The compound of claim 1 or a pharmaceutically acceptable salt thereof, wherein $R^{14}$ is —$C(H)(CH_3)_2$.

10. The compound of claim 1 or a pharmaceutically acceptable salt thereof, wherein $R^{15a}$ and $R^{15b}$ are both H.

11. The compound of claim 1 selected from one of SEQ ID NOs: 10, 70, 71, 73-75, 77-79, 81, 82, and 86 or a pharmaceutically acceptable salt thereof.

12. A pharmaceutical composition comprising the compound of claim 1, or a pharmaceutically acceptable salt thereof and a pharmaceutically acceptable carrier.

13. A method of inhibiting K-Ras protein, comprising contacting the K-Ras protein with an amount of the compound of claim 1, or a pharmaceutically acceptable salt thereof, to inhibit the activity of the K-Ras protein.

14. A method of treating cancer, comprising administering a therapeutically effective amount of the compound of claim 1, or a pharmaceutically acceptable salt thereof, to a subject in need of such treatment.

\* \* \* \* \*

UNITED STATES PATENT AND TRADEMARK OFFICE
CERTIFICATE OF CORRECTION

PATENT NO. : 12,365,706 B2  
APPLICATION NO. : 17/783224  
DATED : July 22, 2025  
INVENTOR(S) : Nicolas C. Boyer et al.

Page 1 of 1

It is certified that error appears in the above-identified patent and that said Letters Patent is hereby corrected as shown below:

In the Claims

In Claim 1 Column 221, Lines 6-42, the chemical structure should appear as provided below (as one complete structure):

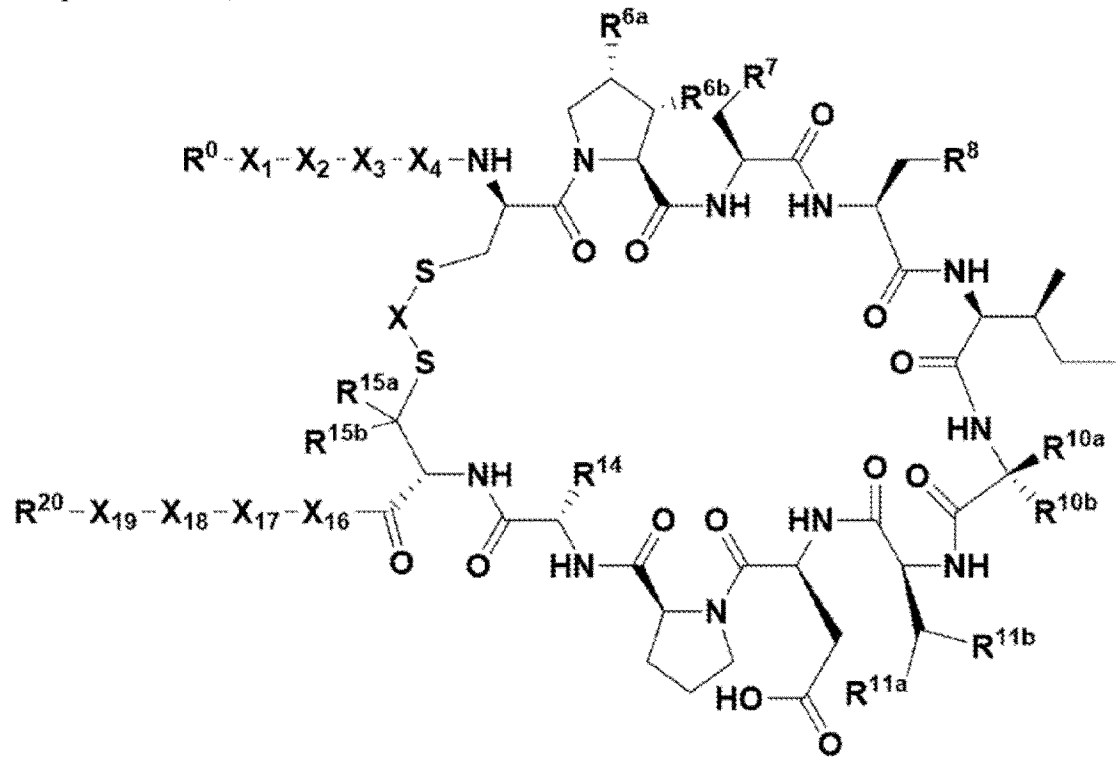

Signed and Sealed this  
Second Day of September, 2025

Coke Morgan Stewart  
*Acting Director of the United States Patent and Trademark Office*